US012775018B2

(12) United States Patent
Frankel et al.

(10) Patent No.: US 12,775,018 B2
(45) Date of Patent: Oct. 27, 2026

(54) SYSTEMS AND METHODS FOR POOLING SAMPLES FOR HIGH-THROUGHPUT ANALYSIS

(71) Applicant: ABBOTT LABORATORIES, Abbott Park, IL (US)

(72) Inventors: Matthew Frankel, Libertyville, IL (US); Patrick Fritchie, Southlake, TX (US); Gregg Williams, Villa Park, IL (US); Bradley Weston, Dallas, TX (US)

(73) Assignee: ABBOTT LABORATORIES, Abbott Park (IL)

( * ) Notice: Subject to any disclaimer, the term of this patent is extended or adjusted under 35 U.S.C. 154(b) by 469 days.

(21) Appl. No.: 18/557,610

(22) PCT Filed: Apr. 29, 2022

(86) PCT No.: PCT/US2022/026995
§ 371 (c)(1),
(2) Date: Oct. 27, 2023

(87) PCT Pub. No.: WO2022/232550
PCT Pub. Date: Nov. 3, 2022

(65) Prior Publication Data

US 2024/0210431 A1 Jun. 27, 2024

Related U.S. Application Data

(60) Provisional application No. 63/302,939, filed on Jan. 25, 2022, provisional application No. 63/302,959,
(Continued)

(51) Int. Cl.
*G01N 35/02* (2006.01)
*B01L 3/00* (2006.01)
(Continued)

(52) U.S. Cl.
CPC ............ *G01N 35/025* (2013.01); *B01L 3/502* (2013.01); *C12Q 1/6806* (2013.01);
(Continued)

(58) Field of Classification Search
None
See application file for complete search history.

(56) References Cited

U.S. PATENT DOCUMENTS 5,451,528 A * 9/1995 Raymoure .......... B01L 3/50853 422/67
7,855,077 B2 12/2010 Wilson
(Continued)

FOREIGN PATENT DOCUMENTS

DE 10 2005 054206 A1 7/2007
EP 2 339 353 B1 6/2011
(Continued)

OTHER PUBLICATIONS

U.S. Appl. No. 18/557,631, filed Oct. 27, 2023.
(Continued)

*Primary Examiner* — William H. Beisner
*Assistant Examiner* — Adrian Carreon
(74) *Attorney, Agent, or Firm* — Baker Botts L.L.P.

(57) ABSTRACT

Systems and methods for onboard pooling of samples for high-throughput analysis of the samples. Including a sample loading area for receiving a plurality of sample tubes, and a sample transport configured to continually transport individual vessels along a transport path from a sample dispense position to a sample capture and transfer position, with intermediate positions therebetween. At least one pipettor to transfer a first and second samples from the sample loading area to the sample transport and to pool the first sample and the second sample in a vessel on the sample transport to form a pooled sample. A sample transfer mechanism to
(Continued)

capture at least a fractionated portion of the pooled sample from the vessel at the sample capture and transfer position and to transfer the at least a fractionated portion of the pooled sample for high-throughput analysis.

38 Claims, 37 Drawing Sheets

Related U.S. Application Data filed on Jan. 25, 2022, provisional application No. 63/302,982, filed on Jan. 25, 2022, provisional application No. 63/302,957, filed on Jan. 25, 2022, provisional application No. 63/181,799, filed on Apr. 29, 2021, provisional application No. 63/181,874, filed on Apr. 29, 2021, provisional application No. 63/181,822, filed on Apr. 29, 2021, provisional application No. 63/181,880, filed on Apr. 29, 2021.

(51) Int. Cl.

| | |
|---|---|
| ***C12Q 1/6806*** | (2018.01) |
| ***C12Q 1/6848*** | (2018.01) |
| ***C12Q 1/70*** | (2006.01) |
| ***G01N 35/00*** | (2006.01) |
| ***G01N 35/10*** | (2006.01) |
| *G01N 35/04* | (2006.01) |

(52) U.S. Cl.

CPC ............ *C12Q 1/6848* (2013.01); *C12Q 1/70* (2013.01); *G01N 35/0099* (2013.01); *G01N 35/1081* (2013.01); *B01L 2200/0647* (2013.01); *B01L 2200/141* (2013.01); *B01L 2300/0829* (2013.01); *G01N 2035/0406* (2013.01); *G01N 2035/041* (2013.01); *G01N 2035/0444* (2013.01); *G01N 2035/0446* (2013.01); *G01N 2035/103* (2013.01)

(56) References Cited

U.S. PATENT DOCUMENTS

| | | | | |
|---|---|---|---|---|
| 8,669,112 | B2 | 3/2014 | Heinonen et al. | |
| 9,029,159 | B2 | 5/2015 | Furrer et al. | |
| 9,128,069 | B2 | 9/2015 | Oeltjen | |
| 9,140,713 | B2 | 9/2015 | Furrer et al. | |
| 9,335,338 | B2 | 5/2016 | Ochranek et al. | |
| 9,416,398 | B2 | 8/2016 | Leying et al. | |
| 9,446,418 | B2 | 9/2016 | Johns et al. | |
| 9,671,416 | B2 | 6/2017 | Giovanoli | |
| 9,725,754 | B2 | 8/2017 | Boyle et al. | |
| 9,952,238 | B2 | 4/2018 | Le Comte | |
| 10,013,526 | B2 | 7/2018 | Oeltjen | |
| 10,101,349 | B2 | 10/2018 | Antoni et al. | |
| 10,266,882 | B2 | 4/2019 | Ye et al. | |
| 10,274,505 | B2 | 4/2019 | Johns et al. | |
| 10,378,008 | B2 | 8/2019 | Roth et al. | |
| 10,466,261 | B2 | 11/2019 | Sano et al. | |
| 10,534,009 | B2 | 1/2020 | Holmes et al. | |
| 10,684,301 | B2 | 6/2020 | Giovanoli | |
| 11,175,301 | B2 | 11/2021 | Mori et al. | |
| 11,242,571 | B2 | 2/2022 | Gao et al. | |
| 11,796,572 | B2 | 10/2023 | Barbut et al. | |
| 2005/0227360 | A1* | 10/2005 | Devlin ............... | G01N 35/0092 436/45 |
| 2015/0168435 | A1 | 6/2015 | Yaginuma et al. | |
| 2017/0211058 | A1 | 7/2017 | Roth et al. | |
| 2017/0269114 | A1* | 9/2017 | Bryant ............... | G01N 35/0099 |
| 2018/0143115 | A1 | 5/2018 | Linnen et al. | |
| 2019/0072462 | A1 | 3/2019 | Pedrazzini | |
| 2019/0346469 | A1* | 11/2019 | Zhang ................ | G01N 33/5304 |
| 2020/0182862 | A1 | 6/2020 | Schmidt et al. | |
| 2020/0190560 | A1 | 6/2020 | Boyle et al. | |
| 2020/0347465 | A1 | 11/2020 | Schmidt et al. | |
| 2021/0181218 | A1 | 6/2021 | Gisler et al. | |
| 2021/0356481 | A1 | 11/2021 | Tran et al. | |
| 2022/0073975 | A1 | 3/2022 | Fang et al. | |
| 2022/0090186 | A1 | 3/2022 | Boeke et al. | |
| 2023/0352159 | A1 | 11/2023 | Jensen et al. | |
| 2023/0383338 | A1 | 11/2023 | Riester et al. | |
| 2024/0003940 | A1 | 1/2024 | Barbut et al. | |
| 2024/0150819 | A1 | 5/2024 | Weidmann et al. | |

FOREIGN PATENT DOCUMENTS

| | | | |
|---|---|---|---|
| EP | 1 902 294 | B1 | 11/2011 |
| EP | 2 465 947 | B1 | 6/2012 |
| EP | 2 598 654 | B1 | 6/2013 |
| EP | 2 598 656 | B1 | 6/2013 |
| EP | 2 518 514 | B1 | 6/2014 |
| EP | 2 776 845 | B1 | 9/2014 |
| EP | 2 990 491 | B1 | 3/2016 |
| EP | 2 156 195 | B1 | 8/2016 |
| EP | 3 139 222 | A1 | 3/2017 |
| EP | 3 182 133 | B1 | 6/2017 |
| EP | 3 294 912 | A1 | 3/2018 |
| EP | 2 076 780 | B1 | 12/2018 |
| EP | 3 513 163 | A1 | 7/2019 |
| EP | 2 979 089 | B1 | 8/2019 |
| EP | 2 778 235 | B1 | 9/2019 |
| EP | 3 538 650 | A1 | 9/2019 |
| EP | 3 589 959 | A1 | 1/2020 |
| EP | 3 639 025 | A1 | 4/2020 |
| EP | 3 670 669 | A1 | 6/2020 |
| EP | 3 879 274 | A1 | 9/2021 |
| EP | 2 856 176 | B1 | 3/2022 |
| EP | 3 985 128 | A1 | 4/2022 |
| EP | 3 995 592 | A1 | 5/2022 |
| EP | 4 053 293 | A1 | 9/2022 |
| EP | 3 899 020 | A4 | 10/2022 |
| EP | 4 229 218 | A1 | 8/2023 |
| EP | 4 301 871 | A1 | 1/2024 |
| EP | 4 308 724 | A1 | 1/2024 |
| EP | 4 165 645 | A4 | 6/2024 |
| EP | 3 992 653 | B1 | 10/2024 |
| EP | 4 443 182 | A2 | 10/2024 |
| JP | 2001-159635 | A | 6/2001 |
| JP | 2009-545747 | A | 12/2009 |
| JP | 2015-114148 | A | 6/2015 |
| JP | 2015-518968 | A | 7/2015 |
| WO | WO 2013/107005 | A1 | 7/2013 |
| WO | WO 2016/020455 | A1 | 2/2016 |
| WO | WO 2018/229270 | A1 | 12/2018 |
| WO | WO 2019/102282 | A1 | 5/2019 |
| WO | WO 2020/050852 | A1 | 3/2020 |
| WO | WO 2020/160502 | A1 | 8/2020 |
| WO | WO 2021/228342 | A2 | 11/2021 |
| WO | WO 2022/061161 | A1 | 3/2022 |
| WO | WO 2022/078775 | A1 | 4/2022 |
| WO | WO 2022/184784 | A1 | 9/2022 |
| WO | WO 2022/198086 | A1 | 9/2022 |

OTHER PUBLICATIONS

De Giorgi et al., "A microarray-based pathogen chip for simultaneous molecular detection of transfusion transmitted infectious agents," Journal of Translational Medicine, 17:156 (2019).

International Search Report mailed Aug. 18, 2022 in International Application No. PCT/US2022/026995.

International Search Report mailed Sep. 15, 2022 in International Application No. PCT/US2022/027067.

Roche Diagnostics: "cobas s 201 system, Operator's Manual," Jan. 31, 2019 XP055949246, Retrieved from the Internet: URL:http://setunari.com/uploads/2k0db79b4d8b.pdf [retrieved on Aug. 4, 2022] 14pgs.

Thayssa Neiva Da Fonseca et al., "Deceased tissue donor serology and molecular testing for HIV, hepatitis B and hepatitis C viruses: a lack of cadaveric validated tests," Cell and Tissue Banking, 17:543-553 (2016).

(56) References Cited

OTHER PUBLICATIONS

U.S. Appl. No. 18/557,631, Jul. 7, 2026 Non-Final Office Action.
Aretzweiler et al., "Generating timely molecular diagnostic test results: workflow comparison of the cobas® 6800/8800 to Panther," Expert Review of Molecular Diagnostics 19:10:951-957 (2019).
Chigurupati et al., "Automated nucleic acid amplification testing in blood banks: An additional layer of blood safety," Asian Journal of Transfusion Science 9(1):9-11 (2015).
Frankel et al., "Development of the Abbott RealTime ZIKA assay for the qualitative detection of Zika virus RNA from serum, plasma, urine, and whole blood specimens using the m2000 system," Journal of Virological Methods 246:117-124 (2017).
Roche Diagnostics. cobas(R) 6800/8800 Systems, User Guide. Publication Version 4.2. Software version 1.3, 45 pgs. (2018).

* cited by examiner

THEORETICAL MAX DECONSTRUCTION EFFICENCY

| Primary Pool Size | 2 | | 4 | | 6 | | 8 | | 12 | | 16 | | 18 | | 24 | | 36 | |
|---|---|---|---|---|---|---|---|---|---|---|---|---|---|---|---|---|---|---|
| | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size |
| Deconstruction Round 1 | 2 | IDT | 4 | IDT | 3 | PL 2 | 2 | PL 4 | 3 | PL 4 | 4 | PL 4 | 3 | PL 6 | 4 | PL 6 | 3 | PL 12 |
| Deconstruction Round 2 | | | | | 2 | IDT | 4 | IDT | 4 | IDT | 4 | IDT | 3 | PL 6 | 3 | PL 6 | 3 | PL 14 |
| Deconstruction Round 3 | | | | | | | | | | | | | 2 | IDT | 2 | IDT | 4 | IDT |
| Deconstruction Round 4 | | | | | | | | | | | | | | | | | | |
| Deconstruction Round 5 | | | | | | | | | | | | | | | | | | |
| Deconstruction Max efficiency (Tests): | 2 | total | 4 | total | 5 | total | 6 | total | 7 | total | 8 | total | 8 | total | 9 | total | 10 | total |
| Max Efficiency Achieved After: | 1 Round Deconstruction | | | | | | 2 Round Deconstruction | | | | | | 3 Round Deconstruction | | | | | |

FIG. 7A

THEORETICAL MAX DECONSTRUCTION EFFICENCY

| Primary Pool Size | 48 | | 64 | | 96 | | 128 | | 192 | |
|---|---|---|---|---|---|---|---|---|---|---|
| | # Tests Used | Int. Pool size | # Tests Used | Int. Pool size | # Tests Used | Int. Pool size | # Tests Used | Int. Pool size | # Tests Used | Int. Pool size |
| Deconstruction Round 1 | 4 | PL 12 | 4 | PL 16 | 4 | PL 24 | 4 | PL 32 | 4 | PL 48 |
| Deconstruction Round 2 | 3 | PL 4 | 4 | PL 4 | 4 | PL 6 | 4 | PL 8 | 4 | PL 12 |
| Deconstruction Round 3 | 4 | IDT | 4 | IDT | 3 | PL 2 | 4 | PL 2 | 3 | PL 4 |
| Deconstruction Round 4 | | | | | 2 | IDT | 2 | IDT | 4 | IDT |
| Deconstruction Round 5 | | | | | | | | | | |
| Deconstruction Max efficiency (Tests): | 11 | total | 12 | total | 13 | total | 14 | total | 15 | total |
| Max Efficiency Achieved After: | 3 Round Deconstruction | | | | 4 Round Deconstruction | | | | | |

| Primary Pool Size | 256 | | 384 | | 480 | | 512 | |
|---|---|---|---|---|---|---|---|---|
| | # Tests Used | Int. Pool size | # Tests Used | Int. Pool size | # Tests Used | Int. Pool size | # Tests Used | Int. Pool size |
| Deconstruction Round 1 | 4 | PL 64 | 4 | PL 96 | 5 | PL 96 | 4 | PL 128 |
| Deconstruction Round 2 | 4 | PL 16 | 4 | PL 24 | 4 | PL 24 | 4 | PL 32 |
| Deconstruction Round 3 | 4 | PL 4 | 4 | PL 6 | 4 | PL 6 | 4 | PL 8 |
| Deconstruction Round 4 | 4 | IDT | 3 | PL 2 | 3 | PL 2 | 4 | PL 2 |
| Deconstruction Round 5 | | | 2 | IDT | 2 | IDT | 2 | IDT |
| Deconstruction Max efficiency (Tests): | 16 | total | 17 | total | 18 | total | 18 | total |
| Max Efficiency Achieved After: | 4 Round Deconstruction | | 5 Round Deconstruction | | | | | |

FIG. 7A Continued

| Max Efficiency 0 Intermediate Pools | | | | | | | | | | | | | | | | | | |
|---|---|---|---|---|---|---|---|---|---|---|---|---|---|---|---|---|---|---|
| Primary Pool Size | 2 | | 4 | | 6 | | 8 | | 12 | | 16 | | 18 | | 24 | | 36 | |
| | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size |
| Final IDT Step | 2 | IDT | 4 | IDT | 6 | IDT | 8 | IDT | 12 | IDT | 16 | IDT | 18 | IDT | 24 | IDT | 36 | IDT |
| Deconstruction Max efficiency (Tests): | 2 | total | 4 | total | 6 | total | 8 | total | 12 | total | 16 | total | 18 | total | 24 | total | 36 | total |
| Max Efficiency Achieved? | Yes | | Yes | | No | | No | | No | | No | | No | | No | | No | |

FIG. 7B

| Max Efficiency 0 Intermediate Pools | | | | | | | | | | | | | | | | | | |
|---|---|---|---|---|---|---|---|---|---|---|---|---|---|---|---|---|---|---|
| Primary Pool Size | 48 | | 64 | | 96 | | 128 | | 192 | | 256 | | 384 | | 480 | | 512 | |
| | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size |
| Final IDT Step | 48 | IDT | 64 | IDT | 96 | IDT | 128 | IDT | 192 | IDT | 256 | IDT | 384 | IDT | 480 | IDT | 512 | PL 128 |
| Deconstruction Max efficiency (Tests): | 48 | total | 64 | total | 96 | total | 128 | total | 192 | total | 256 | total | 384 | total | 480 | total | 512 | total |
| Max Efficiency Achieved? | No | | No | | No | | No | | No | | No | | No | | No | | No | |

FIG. 7B Continued

| Primary Pool Size | 2 | | 4 | | 6 | | 8 | | 12 | | 16 | | 18 | | 24 | | 36 | |
|---|---|---|---|---|---|---|---|---|---|---|---|---|---|---|---|---|---|---|
| | Max Efficiency 1 Intermediate Pools | | | | | | | | | | | | | | | | | |
| | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size |
| Deconstruction Round 1 | 2 | IDT | 4 | IDT | 3 | PL 2 | 2 | PL 4 | 3 | PL 4 | 4 | PL 4 | 3 | PL 6 | 4 | PL 6 | 6 | PL 6 |
| Final IDT Step | | | | | 2 | IDT | 4 | IDT | 4 | IDT | 4 | IDT | 6 | IDT | 6 | IDT | 6 | IDT |
| Deconstruction Max efficiency (Tests): | 2 | total | 4 | total | 5 | total | 6 | total | 7 | total | 8 | total | 9 | total | 10 | total | 12 | total |
| Max Efficiency Achieved? | Yes | | Yes | | Yes | | Yes | | Yes | | Yes | | No | | No | | No | |

FIG. 7C

| Max Efficiency 1 Intermediate Pools | | | | | | | | | | | | | | | | | | |
|---|---|---|---|---|---|---|---|---|---|---|---|---|---|---|---|---|---|---|
| Primary Pool Size | 48 | | 64 | | 96 | | 128 | | 192 | | 256 | | 384 | | 480 | | 512 | |
| | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size |
| Deconstruction Round 1 | 8 | PL 6 | 8 | PL 8 | 16 | PL 6 | 16 | PL 8 | 16 | PL 12 | 16 | PL 16 | 24 | PL 16 | 20 | PL 24 | 32 | PL 16 |
| Final IDT Step | 6 | IDT | 8 | IDT | 6 | IDT | 8 | IDT | 12 | IDT | 16 | IDT | 16 | IDT | 24 | IDT | 16 | IDT |
| Deconstruction Max efficiency (Tests): | 14 | total | 16 | total | 22 | total | 24 | total | 28 | total | 32 | total | 40 | total | 44 | total | 48 | total |
| Max Efficiency Achieved? | No | | No | | No | | No | | No | | No | | No | | No | | No | |

FIG. 7C Continued

| Max Efficiency 2 Intermediate Pools | | | | | | | | | | | | | | | | | | |
|---|---|---|---|---|---|---|---|---|---|---|---|---|---|---|---|---|---|---|
| Primary Pool Size | 2 | | 4 | | 6 | | 8 | | 12 | | 16 | | 18 | | 24 | | 36 | |
| | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size |
| Deconstruction Round 1 | 2 | IDT | 4 | IDT | 3 | PL 2 | 2 | PL 4 | 3 | PL 4 | 4 | PL 4 | 3 | PL 6 | 4 | PL 6 | 3 | PL 12 |
| Deconstruction Round 2 | | | | | 2 | IDT | 4 | IDT | 4 | IDT | 4 | IDT | 3 | PL 2 | 3 | PL 2 | 3 | PL 4 |
| Final IDT Step | | | | | | | | | | | | | 2 | IDT | 2 | IDT | 4 | IDT |
| Deconstruction Max efficiency (Tests): | 2 | total | 4 | total | 5 | total | 6 | total | 7 | total | 8 | total | 8 | total | 9 | total | 10 | total |
| Max Efficiency Achieved? | Yes | | Yes | | Yes | | Yes | | Yes | | Yes | | Yes | | Yes | | Yes | |

FIG. 7D

| Max Efficiency 2 Intermediate Pools | | | | | | | | | | | | | | | | | | |
|---|---|---|---|---|---|---|---|---|---|---|---|---|---|---|---|---|---|---|
| Primary Pool Size | 48 | | 64 | | 96 | | 128 | | 192 | | 256 | | 384 | | 480 | | 512 | |
| | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size |
| Deconstruction Round 1 | 4 | PL 12 | 4 | PL 16 | 6 | PL 16 | 8 | PL 16 | 6 | PL 32 | 8 | PL 32 | 8 | PL 48 | 10 | PL 48 | 16 | PL 32 |
| Deconstruction Round 2 | 3 | PL 4 | 4 | PL 4 | 4 | PL 4 | 4 | PL 4 | 8 | PL 4 | 8 | PL 4 | 8 | PL 6 | 8 | PL 6 | 8 | PL 4 |
| Final IDT Step | 4 | IDT | 4 | IDT | 4 | IDT | 4 | IDT | 4 | IDT | 4 | IDT | 6 | IDT | 6 | IDT | 4 | IDT |
| Deconstruction Max efficiency (Tests): | 11 | total | 12 | total | 13 | total | 14 | total | 15 | total | 16 | total | 17 | total | 18 | total | 18 | total |
| Max Efficiency Achieved? | Yes | | Yes | | No | | No | | No | | No | | No | | No | | No | |

FIG. 7D Continued

| Max Efficiency 4 Intermediate Pools | | | | | | | | | | | | | | | | | | |
|---|---|---|---|---|---|---|---|---|---|---|---|---|---|---|---|---|---|---|
| Primary Pool Size | 2 | | 4 | | 6 | | 8 | | 12 | | 16 | | 18 | | 24 | | 36 | |
| | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size |
| Deconstruction Round 1 | 2 | IDT | 4 | IDT | 3 | PL 2 | 2 | PL 4 | 3 | PL 4 | 4 | PL 4 | 3 | PL 6 | 4 | PL 6 | 3 | PL 12 |
| Deconstruction Round 2 | | | | | 2 | IDT | 4 | IDT | 4 | IDT | 4 | IDT | 3 | PL 2 | 3 | PL 2 | 3 | PL 4 |
| Deconstruction Round 3 | | | | | | | | | | | | | 2 | IDT | 2 | IDT | 4 | IDT |
| Deconstruction Round 4 | | | | | | | | | | | | | | | | | | |
| Final IDT Step | | | | | | | | | | | | | | | | | | |
| Deconstruction Max efficiency (Tests): | 2 | total | 4 | total | 5 | total | 6 | total | 7 | total | 8 | total | 8 | total | 9 | total | 10 | total |
| Max Efficiency Achieved? | Yes | | Yes | | Yes | | Yes | | Yes | | Yes | | Yes | | Yes | | Yes | |

FIG. 7E

| Max Efficiency 4 Intermediate Pools | | | | | | | | | | | | | | | | | | |
|---|---|---|---|---|---|---|---|---|---|---|---|---|---|---|---|---|---|---|
| Primary Pool Size | 48 | | 64 | | 96 | | 128 | | 192 | | 256 | | 384 | | 480 | | 512 | |
| | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size |
| Deconstruction Round 1 | 4 | PL 12 | 4 | PL 16 | 4 | PL 24 | 4 | PL 32 | 4 | PL 48 | 4 | PL 64 | 4 | PL 96 | 5 | PL 96 | 4 | PL 128 |
| Deconstruction Round 2 | 3 | PL 4 | 4 | PL 4 | 4 | PL 6 | 4 | PL 8 | 8 | PL 12 | 4 | PL 16 | 4 | PL 24 | 4 | PL 24 | 4 | PL 32 |
| Deconstruction Round 3 | 4 | IDT | 4 | IDT | 3 | PL 2 | 4 | PL 2 | 3 | PL 4 | 4 | PL 4 | 4 | PL 6 | 4 | PL 6 | 4 | PL 8 |
| Deconstruction Round 4 | | | | | 2 | IDT | 2 | IDT | 4 | IDT | 4 | IDT | 3 | PL 2 | 3 | PL 2 | 4 | PL 2 |
| Final IDT Step | | | | | | | | | | | | | 2 | IDT | 2 | IDT | 2 | IDT |
| Deconstruction Max efficiency (Tests): | 11 | total | 12 | total | 13 | total | 14 | total | 15 | total | 16 | total | 17 | total | 18 | total | 18 | total |
| Max Efficiency Achieved? | Yes | | Yes | | Yes | | Yes | | Yes | | Yes | | Yes | | Yes | | Yes | |

FIG. 7E Continued

| Max Efficiency 4 Intermediate Pools | | | | | | | | | | | | | | | | | | |
|---|---|---|---|---|---|---|---|---|---|---|---|---|---|---|---|---|---|---|
| Primary Pool Size | 2 | | 4 | | 6 | | 8 | | 12 | | 16 | | 18 | | 24 | | 36 | |
| | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size |
| Deconstruction Round 1 | 2 | IDT | 4 | IDT | 3 | PL 2 | 2 | PL 4 | 3 | PL 4 | 4 | PL 4 | 3 | PL 6 | 4 | PL 6 | 3 | PL 12 |
| Deconstruction Round 2 | | | | | 2 | IDT | 4 | IDT | 4 | IDT | 4 | IDT | 3 | PL 2 | 3 | PL 2 | 3 | PL 4 |
| Deconstruction Round 3 | | | | | | | | | | | | | 2 | IDT | 2 | IDT | 4 | IDT |
| Deconstruction Round 4 | | | | | | | | | | | | | | | | | | |
| Final IDT Step | | | | | | | | | | | | | | | | | | |
| Deconstruction Max efficiency (Tests): | 2 | total | 4 | total | 5 | total | 6 | total | 7 | total | 8 | total | 8 | total | 9 | total | 10 | total |
| Max Efficiency Achieved?: | Yes | | Yes | | Yes | | Yes | | Yes | | Yes | | Yes | | Yes | | Yes | |

FIG. 7F

| Max Efficiency 4 Intermediate Pools | | | | | | | | | | | | | | | | | | |
|---|---|---|---|---|---|---|---|---|---|---|---|---|---|---|---|---|---|---|
| Primary Pool Size | 48 | | 64 | | 96 | | 128 | | 192 | | 256 | | 384 | | 480 | | 512 | |
| | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size | # Tests Used | Int. Pool size |
| Deconstruction Round 1 | 4 | PL 12 | 4 | PL 16 | 4 | PL 24 | 4 | PL 32 | 4 | PL 48 | 4 | PL 64 | 4 | PL 96 | 5 | PL 96 | 4 | PL 128 |
| Deconstruction Round 2 | 3 | PL 4 | 4 | PL 4 | 4 | PL 6 | 4 | PL 6 | 4 | PL 12 | 4 | PL 16 | 4 | PL 24 | 4 | PL 24 | 4 | PL 32 |
| Deconstruction Round 3 | 4 | IDT | 4 | IDT | 3 | PL 2 | 4 | PL 2 | 3 | PL 4 | 4 | PL 4 | 4 | PL 6 | 4 | PL 6 | 4 | PL 8 |
| Deconstruction Round 4 | | | | | 2 | IDT | 2 | IDT | 4 | IDT | 4 | IDT | 3 | PL 2 | 3 | PL 2 | 4 | PL 2 |
| Final IDT Step | | | | | | | | | | | | | 2 | IDT | 2 | IDT | 2 | IDT |
| Deconstruction Max efficiency (Tests): | 11 | total | 12 | total | 13 | total | 14 | total | 15 | total | 16 | total | 17 | total | 18 | total | 18 | total |
| Max Efficiency Achieved?: | Yes | | Yes | | Yes | | Yes | | Yes | | Yes | | Yes | | Yes | | Yes | |

FIG. 7F Continued

| Serum / Plasma / Lysed Whole Blood | | | | | | | |
|---|---|---|---|---|---|---|---|
| | Individual Samples | Pool of 2 | Pool of 4 | Pool of 6 | Pool of 12 | Pool of 18 | Pool of 24 |
| Time To Result | 35 minutes | 35 minutes | 35.5 min | 36 min | 38 min | 39 min | 40 min |
| Throughput | 150 samples / hour | 150 pools / hour | 75 pools/hour | 50 pools/hour | 25 pools/hour | 16.7 pools/hour | 12.5 pools/hour |

FIG. 9A

| Whole Blood with Pre-Treatment Process | | |
|---|---|---|
| | Individual Samples | Pool of 6 |
| Time To Result | 42 minutes | 42 minutes |
| Throughput | 75 samples / hour | 21 pools/hour |

FIG. 9B

| Assay Configurations | |
|---|---|
| Non Split Eluate | Split Eluate |
| HAV/Parvo | HIV/HBV/HCV |
| WNV/ChikV/Dengue/Zika | |
| Malaria | |
| Babesia | |

SYSTEMS AND METHODS FOR POOLING SAMPLES FOR HIGH-THROUGHPUT ANALYSIS

CROSS-REFERENCE TO RELATED APPLICATIONS

This application is a U.S. National Stage Patent Application under 35 U.S.C. § 371 of International Patent Application No. PCT/US2022/026995, filed Apr. 29, 2022, which claims priority to U.S. provisional application No. 63/302,957, filed Jan. 25, 2022, and U.S. provisional application No. 63/302,959, filed Jan. 25, 2022, and U.S. provisional application No. 63/302,982, filed Jan. 25, 2022, and U.S. provisional application No. 63/302,939, filed Jan. 25, 2022, and U.S. provisional application No. 63/181,799, filed Apr. 29, 2021, and U.S. provisional application No. 63/181,822, filed Apr. 29, 2021, and U.S. provisional application No. 63/181,874, filed Apr. 29, 2021, and U.S. provisional application No. 63/181,880, filed Apr. 29, 2021, the entire contents of each of which are hereby incorporated by reference.

BACKGROUND

Field of the Disclosed Subject Matter

The presently disclosed subject matter relates to systems and methods for pooling biological samples, e.g., blood, serum, or plasma samples, from donors and/or patients, for high-throughput analysis of the samples, e.g., for high-throughput nucleic acid testing of the samples.

Description of Related Art

Pooling, or pooled testing, is a form of group testing where multiple liquid samples are mixed together to form a pool, which can then be analyzed. Pooling can, for example, reduce the amount of time and/or the number of tests required to analyze a group of samples and can increase testing capacity. For example, in one pooling strategy, known as Dorfman Pooling, a pool of samples is tested for a qualitative response (i.e., positive/negative or reactive/non-reactive), and all samples in a negative pool are declared negative. Accordingly, for a negative pool, a single test can be used to assess all constituent samples of the pool.

Pooled testing has been used in the detection of pathogens and infectious agents in the donated blood supply. For example, pooled testing has been used in combination with nucleic acid testing (NAT) to screen donated blood for, e.g., HIV, HCV, HBV, *Babesia*, Zika and West Nile Virus. In an exemplary workflow for screening donated blood, blood can be collected from a donor into a blood bag and into multiple sample collection tubes at a collection site. The blood bag can then be transported to a blood collection facility for further processing and storage, and the collection tubes can be transported to a blood screening laboratory to subject the samples to testing for pathogens or infectious diseases and for blood grouping and typing. For example, one or more of the samples may be pooled with samples from other donors and subjected to NAT for, e.g., HIV, HCV, HBV, *Babesia*, Zika and West Nile Virus. If all tests are negative for the pooled sample, then each of the individual donor samples that were mixed together to form the pool can be considered to have tested negative for the pathogens and/or infectious agents the pool was tested for.

Although pooled testing can facilitate higher testing throughout, additional time and laboratory equipment can be required to prepare sample pools. For example, conventionally, pooled samples are prepared on dedicated pieces of equipment within a testing facility, such as a dedicated liquid handler or pooler, which is a type of laboratory equipment that can automate and monitor the transfer of liquids between containers, such as to create a sample pool. For example, one pooling strategy that can be used for NAT testing includes forming sample pools of 96 samples on a liquid handler and then transferring the pools of 96 samples to a separate instrument for NAT testing. To maximize the utilization of NAT testing instruments, NAT testing centers can include up to eight poolers to support a single NAT testing instrument. The large number of poolers used to support each NAT testing instrument can occupy valuable laboratory floor space and can increase testing cost.

Further, conventional pool deconstruction strategies can be time consuming and error prone. Pool deconstruction can be used to identify which constituent sample of a sample pool contains a pathogen and/or infectious agent after the pooled sample tests positive for the pathogen and/or infectious agent. Conventional pool deconstruction can involve multiple manual steps over a period of many hours. For example, typical pool deconstruction can require an operator to manually retrieve and transfer individual samples to a liquid handler to form smaller intermediate sample pools, or sub-pools, which can then be manually transferred to an instrument for further testing. Additionally or alternatively, deconstruction may require an operator to manually retrieve individual donor samples from a positive pool or intermediate pool and transfer the individual samples to an instrument for further testing. The numerous manual steps involved in conventional deconstruction can create opportunities for error in the deconstruction process. Further, some samples can have a limited suitability range (e.g., limited room temperature suitability range), and the time requirements of conventional deconstruction can result in samples being discarded. Additionally, deconstruction can create a laboratory bottleneck, as liquid handlers that would otherwise be used to create new sample pools can be diverted for pool deconstruction.

Thus, there is a need for pooling systems and methods that can increase testing throughput, reduce the laboratory floor space required for testing, and reduce testing error and cost. The disclosed subject matter fulfills these and other needs.

SUMMARY

The purpose and advantages of the disclosed subject matter will be set forth in and apparent from the description that follows, as well as will be learned by practice of the disclosed subject matter. For purpose of illustration and not limitation, the various embodiments described herein relate to automated systems and methods for pooling biological samples for high-throughput analysis of the samples. Additional advantages of the disclosed subject matter will be realized and attained by the automated systems and methods particularly pointed out in the written description and claims hereof, as well as from the appended drawings.

To achieve these and other advantages, and in accordance with the purpose of the disclosed subject matter, as embodied and broadly described, the disclosed subject matter includes automated systems for onboard pooling of samples for high-throughput analysis of the samples. Automated systems in accordance with the disclosed subject matter include a sample loading area for receiving a plurality of sample tubes, and a sample transport configured to continually transport individual vessels along a transport path from a sample dispense position to a sample capture and transfer position, with intermediate positions therebetween. Automated systems in accordance with the disclosed subject matter further include at least one pipettor to transfer a first sample from a first sample tube at the sample loading area and a second sample from a second sample tube at the sample loading area to the sample transport and to pool the first sample and the second sample in a vessel on the sample transport to form a pooled sample. Automated systems in accordance with the disclosed subject matter further include a sample transfer mechanism to capture at least a fractionated portion of the pooled sample from the vessel at the sample capture and transfer position and to transfer the at least a fractionated portion of the pooled sample for high-throughput analysis.

The disclosed subject matter further includes methods for onboard pooling of samples for high-throughput analysis of the samples. Methods in accordance with the disclosed subject matter include receiving a plurality of sample tubes at a sample loading area and transferring a first sample from a first sample tube at the sample loading area and a second sample from a second sample tube at the sample loading area to a sample dispense position on a sample transport. Methods in accordance with the disclosed subject matter further include continually transporting individual vessels on the sample transport along a transport path from the sample dispense position to a sample capture and transfer position, with intermediate positions therebetween, and pooling the first sample and the second sample in a vessel on the sample transport to form a pooled sample. Methods in accordance with the disclosed subject matter further include capturing at least a fractionated portion of the pooled sample from the vessel at the sample capture and transfer position for high-throughput analysis.

In certain embodiments, the high-throughput analysis can include a qualitative assay on the pooled sample to detect a plurality of pathogens or infectious agents. For example, in certain embodiments the high-throughput analysis can include a nucleic acid analysis on the pooled sample. For example and not imitation, the plurality of pathogens or infectious agents to be detected can include one or more of SARS-COV-2 (COVID-19), HIV-1, HIV-2, HBV, HCV, CMV, Parvo B19 Virus, HAV, *Chlamydia*, Gonorrhea, WNV, Zika Virus, Dengue Virus, Chikungunya Virus, Influenza, *Babesia*, Malaria, and HEV.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the systems and methods of the disclosed subject matter. Together with the description, the drawings serve to explain the principles of the disclosed subject matter.

BRIEF DESCRIPTION OF THE DRAWINGS

The details of the disclosed subject matter, both as to its structure and operation, may be apparent by study of the accompanying figures, in which like reference numerals refer to like parts. The components in the figures are not necessarily to scale, emphasis instead being placed upon illustrating the principles of the disclosed subject matter. Moreover, all illustrations are intended to convey concepts, where relative sizes, shapes and other detailed attributes may be illustrated schematically rather than literally or precisely.

FIGS. 7A-7F illustrate exemplary pool deconstruction strategies in accordance with an aspect of the disclosed subject matter.

FIGS. 9A and 9B depict exemplary throughput for identified sample types and processes for the exemplary system depicted in FIGS. 2A-2C.

FIG. 13A depicts the scenarios of not splitting (top process path), splitting with an odd number of assays (middle process path), and splitting with an even number of assays (bottom process path). In FIG. 13B, various scenarios of assays combinations and eluate splitting illustrates the benefit and utility of eluate splitting.

DETAILED DESCRIPTION

Figure 1A:
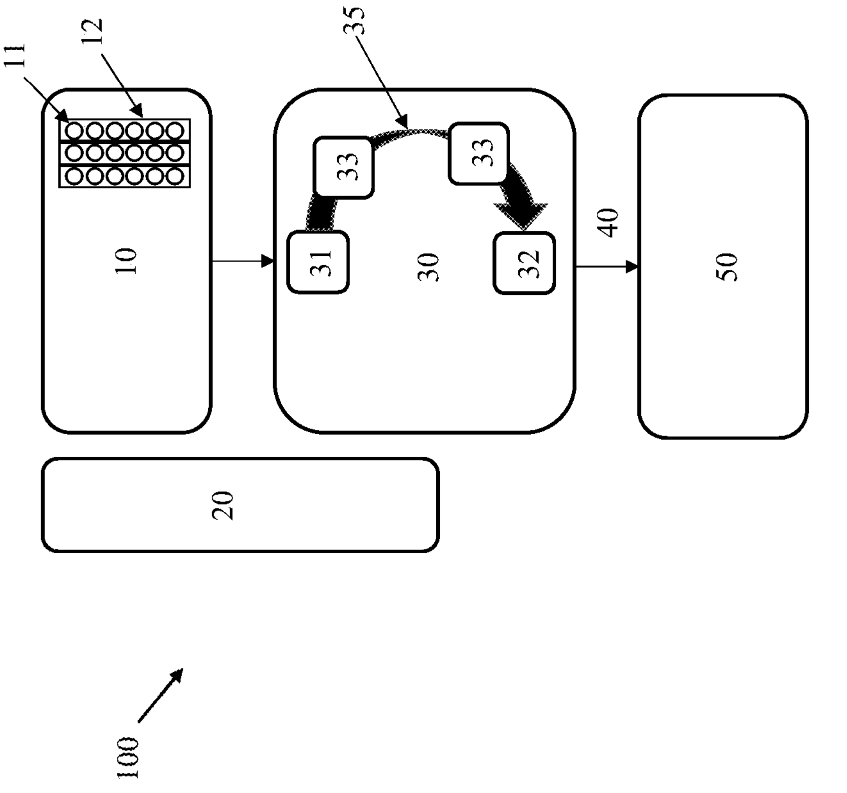
FIG. 1A is a schematic diagram illustrating an exemplary system in accordance with the disclosed subject matter.

Reference will now be made in detail to the various exemplary embodiments of the disclosed subject matter, which are illustrated in the accompanying drawings. The structure and corresponding method of operation of the disclosed subject matter will be described in conjunction with the detailed description of the system. The accompanying drawings, where like reference numerals refer to identical or functionally similar elements throughout the separate views, serve to further illustrate various embodiments and to explain various principles and advantages all in accordance with the disclosed subject matter.

The terms used in this specification generally have their ordinary meanings in the art, within the context of this disclosure and in the specific context where each term is used. Certain terms are discussed below, or elsewhere in the specification, to provide additional guidance to the practitioner in describing the systems and methods of the present disclosure and how to make and use them.

The disclosed subject matter is generally directed to automated systems and methods for onboard pooling of samples for high-throughput analysis of the samples.

The term "throughput" as used herein is a broad term, and is to be given its ordinary and customary meaning to a person of skill in the art (and it is not to be limited to a special or customized meaning), and can refer without limitation to the number of analysis results obtained per unit time, e.g., per hour. For purpose of example and not limitation throughput can refer to the number of test results per unit time, e.g., per hour. For example and not limitation, throughput can refer to the number of nucleic analysis results per unit time, e.g., per hour. Additionally or alternatively, throughput can refer without limitation to the number of samples analyzed per unit time, e.g., hour.

The term "about" or "approximately" as used herein means within an acceptable error range for the particular value as determined by one of ordinary skill in the art, which depends in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

In certain embodiments, the samples can be biological samples, e.g., biological fluid samples. In certain embodiments, the biological fluid sample can be a bodily secretion. Non-limiting examples of biological fluid and bodily secretion samples include blood (e.g., whole blood, lysed whole blood, serum, or plasma), saliva, sweat, tears, mucus, urine, lymphatic fluid, cerebrospinal fluid, interstitial fluid, bronchoalveolar lavage fluid or any other sample suitable for analysis using the methods and techniques described herein. In certain embodiments, the biological fluid sample is intended for clinical use, e.g., donor blood for use in transfusion. Additionally or alternatively, in certain embodiments samples can include whole blood, plasma, serum, cellular blood components, and/or other blood products.

1. Onboard Pooling Systems

Automated systems for onboard pooling of samples in accordance with the disclosed subject matter generally include a sample loading area for receiving a plurality of sample tubes, and a sample transport configured to continually transport individual vessels along a transport path from a sample dispense position to a sample capture and transfer position, with intermediate positions therebetween. Automated systems in accordance with the disclosed subject matter further include at least one pipettor to transfer a first sample from a first sample tube at the sample loading area and a second sample from a second sample tube at the sample loading area to the sample transport and to pool the first sample and the second sample in a vessel on the sample transport to form a pooled sample. Automated systems in accordance with the disclosed subject matter further include a sample transfer mechanism to capture at least a fractionated portion of the pooled sample from the vessel at the sample capture and transfer position and to transfer the at least a fractionated portion of the pooled sample for high-throughput analysis.

The term "onboard" as used herein is a broad term, and is to be given its ordinary and customary meaning to a person of skill in the art (and it is not to be limited to a special or customized meaning), and refers without limitation to the inclusion of components and/or the performance of method steps on a single system (e.g., a single piece of laboratory equipment). For example and not limitation, onboard pooling can include pooling samples and performing analysis of the pooled sample, such as to detect the presence of one or more pathogens or infectious agents, on the same piece of laboratory equipment. For example and not limitation, onboard pooling can include pooling samples and performing analysis of the pooled sample on the same piece of equipment without manual intervention between pooling and analysis.

For purpose of illustration and not limitation, reference is made to the schematic representation of an exemplary automated system 100 depicted in FIG. 1A. The automated system 100 includes a sample loading area 10 for receiving a plurality of sample tubes 11. The term "sample loading area" as used herein is a broad term, and is to be given its ordinary and customary meaning to a person of skill in the art (and it is not to be limited to a special or customized meaning), and refers without limitation to a location in the system where a pipettor can access sample tubes to transfer samples from the tubes for sample preparation, onboard pooling, and/or high-throughput analysis. The sample loading area can have any suitable configuration. For purpose of example and not limitation, the sample loading area can be connected with a laboratory automation system, such as systems for automatically transporting samples within a laboratory. Exemplary laboratory automation systems are described in U.S. Pat. No. 9,182,419 9,309,062, which are hereby incorporated by reference in their entirety. Additionally or alternatively, and as embodied herein, sample tubes 11 can be stored in sample tube racks 12, which can be positioned within the sample loading area by an operator and/or by automated sample handling systems, such as one or more robotic sample handlers. In certain embodiments, samples, e.g., in sample tubes, can be stored at the sample loading area 10 while onboard pooling and high-throughput analysis is performed on portions of the samples. Additionally or alternatively, samples can be stored at the sample loading area during onboard deconstruction, as described further herein.

Automated systems in accordance with the disclosed subject matter further include a sample transport 30 configured to continually transport individual vessels 11 along a transport path 35 from a sample dispense position 31 to a sample capture and transfer position 32, with intermediate positions 33 therebetween. The term "sample transport" as used herein is a broad term, and is to be given its ordinary and customary meaning to a person of skill in the art (and it is not to be limited to a special or customized meaning), and refers without limitation to a component configured for transporting, transferring, and/or carrying samples from one position to another. For purpose of example and not limitation, sample transports can include conveyors, such as a belt conveyor or a chain conveyor, or a vehicle system, such as an electronic vehicle system. Additionally or alternatively, sample transports can include a serpentine path.

Additionally or alternatively, the sample transport can include one or more robotic handlers. Additionally or alternatively, sample transports can include an extrusion. Additionally or alternatively, sample transports can include a carousel. For purpose of example, and as embodied herein, the sample transport can transport vessels continually along the transport path in a stepwise or lockstep fashion. For example, the sample transport can pause at each position along the transport path. The configuration of the lockstep can be selected as desired.

The automated system 100 further includes at least one pipettor 200 to transfer a first sample from a first sample tube at the sample loading area 10 and a second sample from a second sample tube at the sample loading area 10 to the sample transport 30 and to pool the first sample and the second sample in a vessel on the sample transport 30 to form a pooled sample. For purpose of example and not limitation, the at least one pipettor 200 can include a robotic pipettor, such as a gantry pipettor. The pipettor can access sample tubes 11 at the sample loading area 10 and the sample transport 30 and can transfer samples between the sample loading area 10 and the sample transport 30. For example, the at least one pipettor 20 can transfer samples using known "Sip & Spit" techniques. Additionally or alternatively, the at least one pipettor 20 can include disposable pipette tips for transferring samples, as further described herein.

The automated system 100 further include a sample transfer mechanism 40 to capture at least a fractionated portion of the pooled sample from the vessel at the sample capture and transfer position 32 and to transfer the at least a fractionated portion of the pooled sample for high-throughput analysis. The term "sample transfer mechanism" as used herein is a broad term, and is to be given its ordinary and customary meaning to a person of skill in the art (and it is not to be limited to a special or customized meaning), and refers without limitation to a component configured to move at least a fractionated portion of a pooled sample, such as one or more analytes of interest, from a vessel to another position within the system. For purpose of example and not limitation, the sample transfer mechanism can include a pipettor, such as a robotic pipettor. Additionally or alternatively, the sample transfer mechanism can include a magnetic tip, which can capture magnetic microparticles from the pooled sample having nucleic acids or antigens bound thereto, as described further herein.

Systems for onboard pooling in accordance with the disclosed subject matter are configured to perform high-throughput analysis of pooled samples. For example and not limitation and as embodied herein, the system 100 can include a detection area 50, which can be used to detect the presence of one or more analytes, such as for example and not limitation, one or more of a plurality of pathogens or infectious agents. For example and not limitation and as described further herein, the detection area 50 can include components for additional sample preparation of pooled samples, such as washing systems. Additionally or alternatively and as described further herein, the detection area 50 can include components for performing known sample analysis techniques, such as for example, immunoassay analysis, clinical chemistry, spectrophotometry, and/or nucleic acid analysis.

Figure 1B:
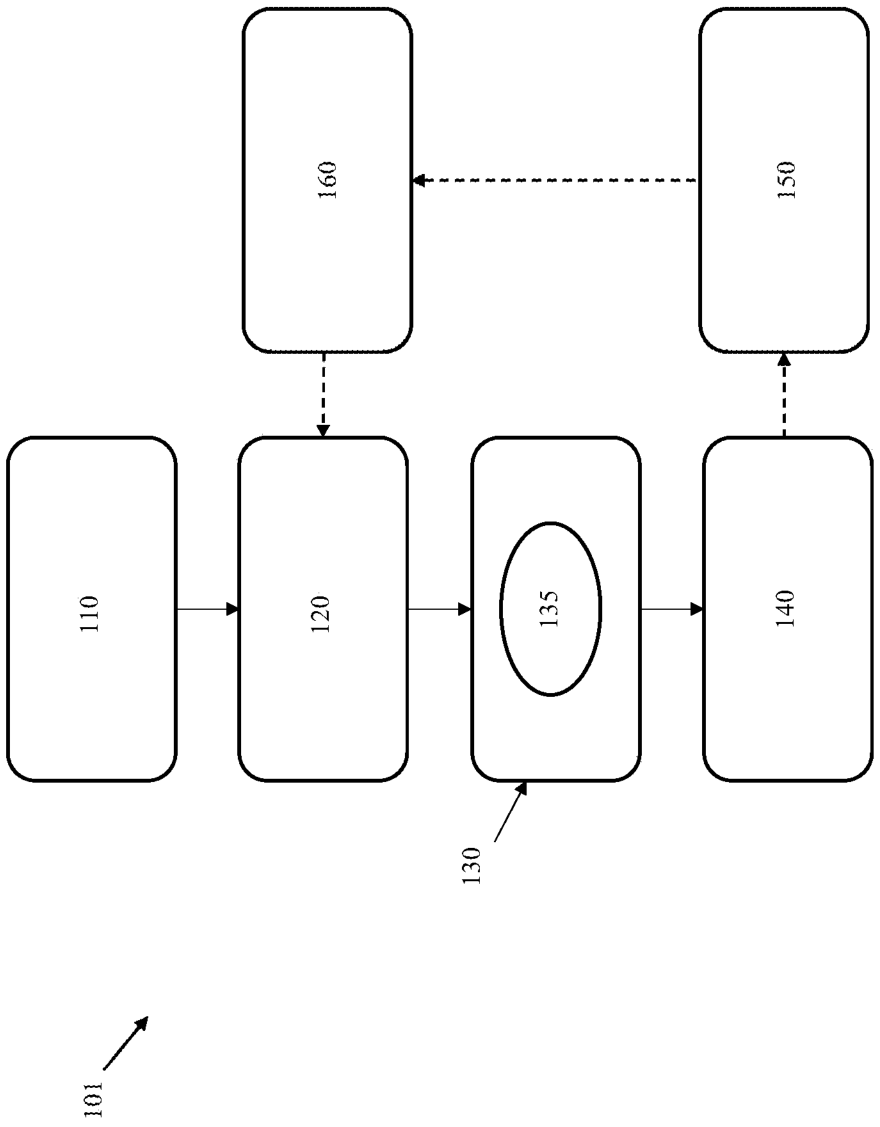
FIG. 1B is flow chart illustrating an exemplary method in accordance with the disclosed subject matter.

The disclosed subject matter further includes methods for onboard pooling of samples for high-throughput analysis of the samples. For example and illustration and not limitation, reference is made to the exemplary method depicted in FIG. 1B. Methods in accordance with the disclosed subject matter include receiving a plurality of sample tubes at a sample loading area 10 as represented by reference number 110. For purpose of example and not limitation, samples can be received at the sample loading area by a laboratory automation system delivering the samples to the sample loading area 10. For example and not limitation, sample loading areas can include one or more interfaces to a laboratory automation system (LAS), such as for example a LAS that transports sample tubes around the laboratory to different analyzers. As embodied herein, the at least one pipettor can aspirate samples from sample tubes at the LAS for onboard pooling and high-throughput analysis. Additionally or alternatively, an operator may place samples at the sample loading area 10.

Methods in accordance with the disclosed subject matter further include transferring, as represented by reference number 120, a first sample from a first sample tube at the sample loading area 10 and a second sample from a second sample tube at the sample loading area 10 to a sample dispense position 31 on a sample transport 30. For purpose of example and as embodied herein, transferring samples from the sample loading area 10 to the sample transport 30 can be performed using at least one pipettor 20.

Methods in accordance with the disclosed subject matter further include continually transporting, as represented by reference number 130, individual vessels 11 on the sample transport 30 along a transport path 35 from the sample dispense position 31 to a sample capture and transfer position 32, with intermediate positions 33 therebetween. The term "continually transporting" as used herein is a broad term, and is to be given its ordinary and customary meaning to a person of skill in the art (and it is not to be limited to a special or customized meaning), and refers without limitation to transporting, transferring, and/or carrying samples from one position to another automatically, and one after the other in a stream-like fashion, wherein at least during steady-state operation, addition of a first vessel to the sample transport at a first position can coincide with removal of another vessel from the sample transport at a second downstream position. For purpose of example and not limitation, individual vessels can be continually transported using conveyors, such as a belt conveyor or a chain conveyor, extrusion, and/or one or more robotic handlers. Additionally or alternatively, the transport path can include a serpentine path and individual vessels can be continually transported along the serpentine path. Additionally or alternatively, and as embodied herein, samples can be continually transported using a carousel.

Methods in accordance with the disclosed subject matter further include pooling the first sample and the second sample in a vessel on the sample transport 30 to form a pooled sample, as represented by reference number 135. For example and not limitation, the first sample and the second sample can be pooled in a vessel on the sample transport 30 using the at least one pipettor 20. For example, and not limitation, the first and second samples can be dispensed into the vessel by the at least one pipettor 20 to combine and pool the first and second samples. For example a first sample can be aspirated from the sample loading area 10 and dispensed into a first vessel at the sample dispense position 31 of the sample transport 30. A second sample can also be aspirated from the sample loading area 10 and dispensed into the first vessel at the sample dispense position 31 of the sample transport 30 to combine and pool the first and second samples. In certain embodiments, the first and second samples can be dispensed into the first vessel at the sample dispense position 31 prior to the sample transport transporting the first vessel and the pooled sample to a first intermediate position 33. In certain embodiments, the pooled first and second samples can then be transported along the transport path 35 to the sample capture and transfer position 32, where at least a fractionated portion of the pooled sample can be transferred for high-throughput analysis.

In certain embodiments onboard pooling can include combining and pooling additional samples in the first vessel. For purpose of example and as embodied herein, a third sample and a fourth sample can be combined with the first sample and second sample in the first vessel to add the third and fourth samples to the pooled sample. As embodied herein, pooling the samples can include transferring the third sample from a third sample tube at the sample loading area 10 and a fourth sample from a fourth sample tube at the sample loading area 10 to the first vessel at the first intermediate position 33. The pooled first, second, third, and fourth samples in the first vessel can then be transported along the transport path to the sample capture and transfer position 1240, where at least a fractionated portion of the pooled sample can be transferred for high-throughput analysis. For purpose of example and as embodied herein, two samples can be transferred to and combined in the first vessel at each position on the sample transport until the desired pool size is achieved (e.g., two samples can be dispensed at the sample dispense position, two samples can be dispensed at the first intermediate position, and two samples can be dispensed at the second intermediate position). Additionally or alternatively, one sample can be dispensed at each position until the desired pool size is achieved. Additionally or alternatively, three samples can be dispensed at each position. For purpose of example and not limitation, between 2 and 100 samples can be pooled in the first vessel on the sample transport as the first vessel is transported along the transport path. In certain embodiments between 2 and 50 samples can be pooled in the first vessel on the sample transport as the first vessel is transported along the transport path. In certain embodiments between 2 and 24 samples can be pooled in the first vessel on the sample transport as the first vessel is transported along the transport path.

In certain embodiments, samples can be transferred between vessels on the sample transport 30. For example and as described further herein, pooled samples can be aspirated from a vessel on the sample transport (e.g., at an intermediate position) and dispensed into a new vessel on the sample transport (e.g., at the sample dispense position) to initiate additional sample preparation processes. For example, a pooled sample can be aspirated from a vessel at an intermediate position and dispensed into a vessel (e.g., at the sample dispense position) to initiate a lysis process.

In accordance with another aspect of the disclosed subject matter, a sample pre-treatment process can be performed before onboard pooling and pre-treated samples can be pooled on the sample transport. For example a first sample can be dispensed into a first vessel at the sample dispense position, prior to the sample transport transporting the first vessel to a first intermediate position. A second sample can then be dispensed into a second vessel at the sample transport prior to the sample transport transporting the first and second vessels further along the transport path. The first and second samples, and any other samples to be pooled, can be transported along the transport path to allow time for the pre-treatment process to be performed. In certain embodiments the pre-treatment process can be a pre-treatment lysis process (e.g., a whole blood pre-treatment lysis process). The first and second samples and any other samples to be pooled can then be aspirated from their respective vessels and dispensed into a new vessel (e.g., at the sample dispense position) to combine and pool the samples.

Methods in accordance with the disclosed subject matter further include capturing at least a fractionated portion of the pooled sample from the vessel at the sample capture and transfer position for high-throughput analysis, as represented by reference number 140. For purpose of example and not limitation, capturing at least a fractionated portion of the pooled sample can include aspirating at least a fractionated portion of the pooled sample from the vessel using a pipettor. Additionally or alternatively, capturing the at least a fractionated portion of the pooled sample can include capturing microparticles having analytes of interest bound thereto. For example, capturing the at least a fractionated portion of the pooled sample can include using one or more magnets to capture microparticles having analytes of interest from the pooled sample bound thereto.

For purpose of example and not limitation, the high-throughput analysis can include one or more analysis techniques for performing a qualitative assay on the pooled sample. For example, the high-throughput analysis can include an immunoassay analysis. Additionally or alternatively, the high-throughput analysis can include a nucleic acid analysis. Additionally or alternatively, and as embodied herein, the high-throughput analysis can include detecting the presence of one or more of a plurality of pathogens or infectious agents in the pooled sample as represented by reference number 150.

In accordance with an aspect of the disclosed subject matter, upon detection of a pathogen or infectious agent in the pooled sample methods can further include onboard deconstruction of a pooled sample, as represented by reference number 160, to determine which of the first sample, the second sample, or any additional sample in the pooled sample, includes the pathogen or infectious agent. For example and as embodied herein, onboard deconstruction can include transferring a subset of the samples used to form the pooled sample to the sample transport 30 for onboard pooling to form sub-pools for further high-throughput analysis to determine which of the samples used to form the pooled sample includes the pathogen or infectious agent.

Figure 2A:
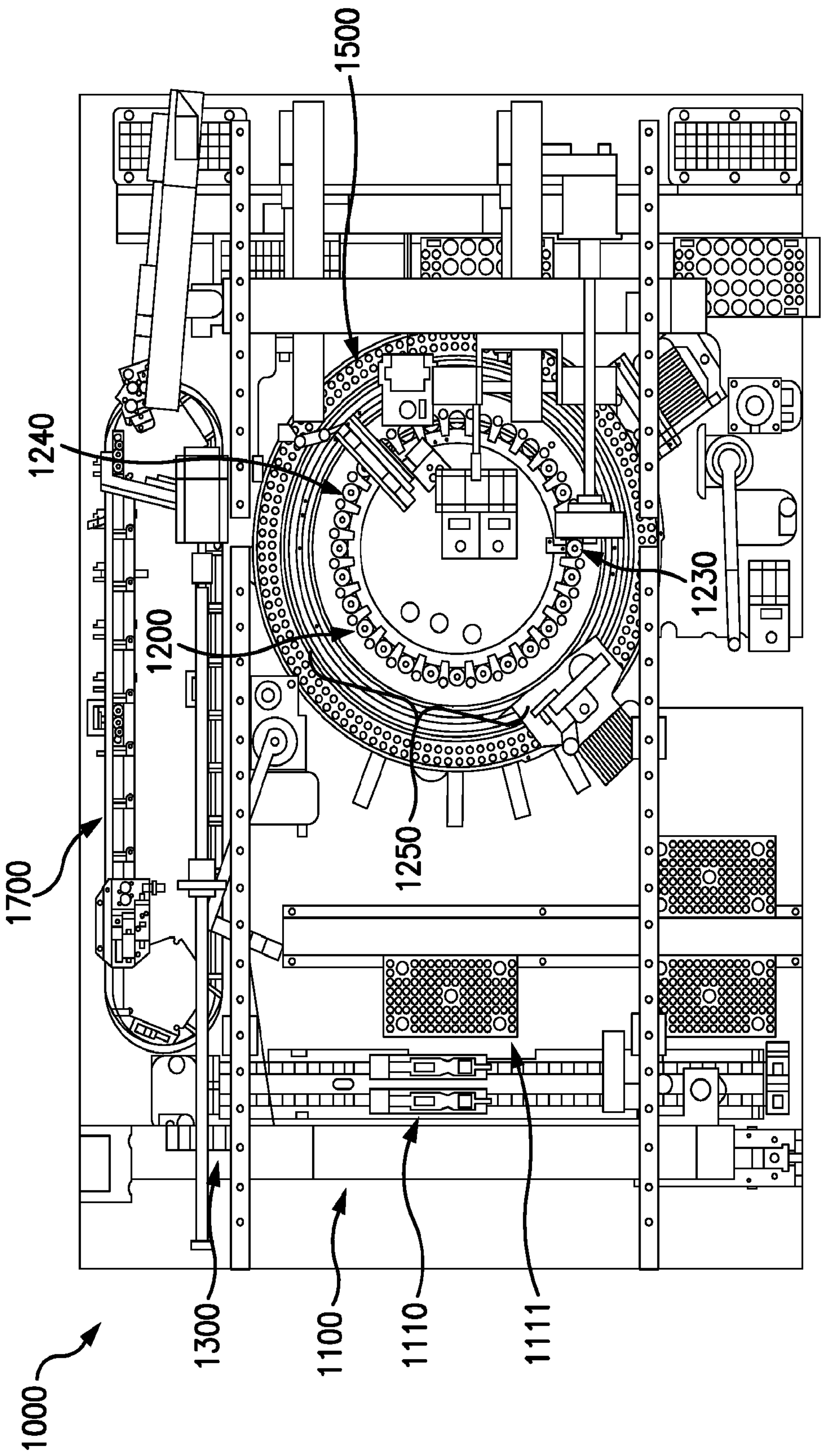
FIG. 2A is a partial top view of an exemplary system in accordance with the disclosed subject matter.
Figure 2B:
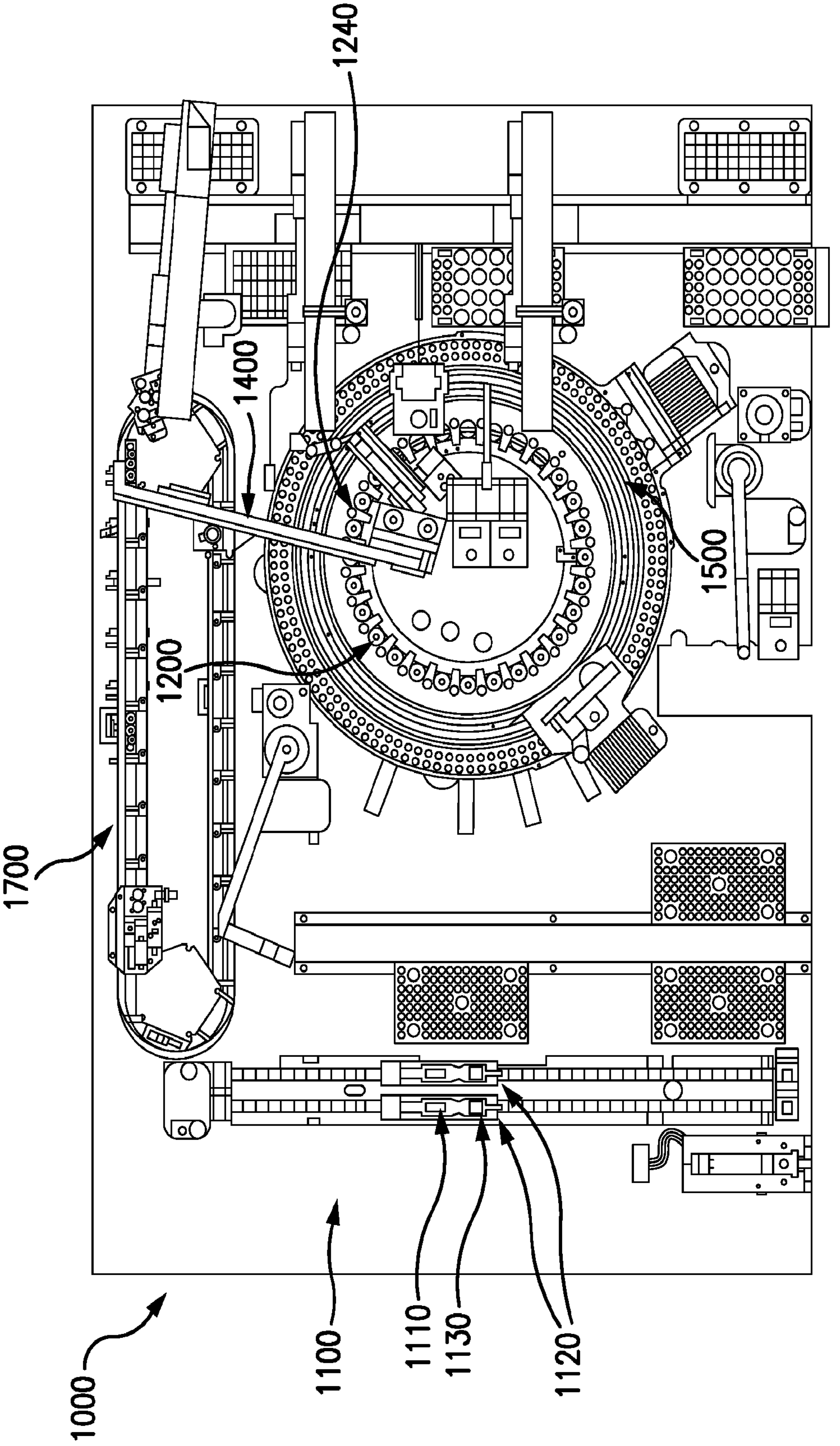
FIG. 2B is a partial top view of the exemplary system of FIG. 1A with additional components omitted for purpose of illustration.
Figure 2C:
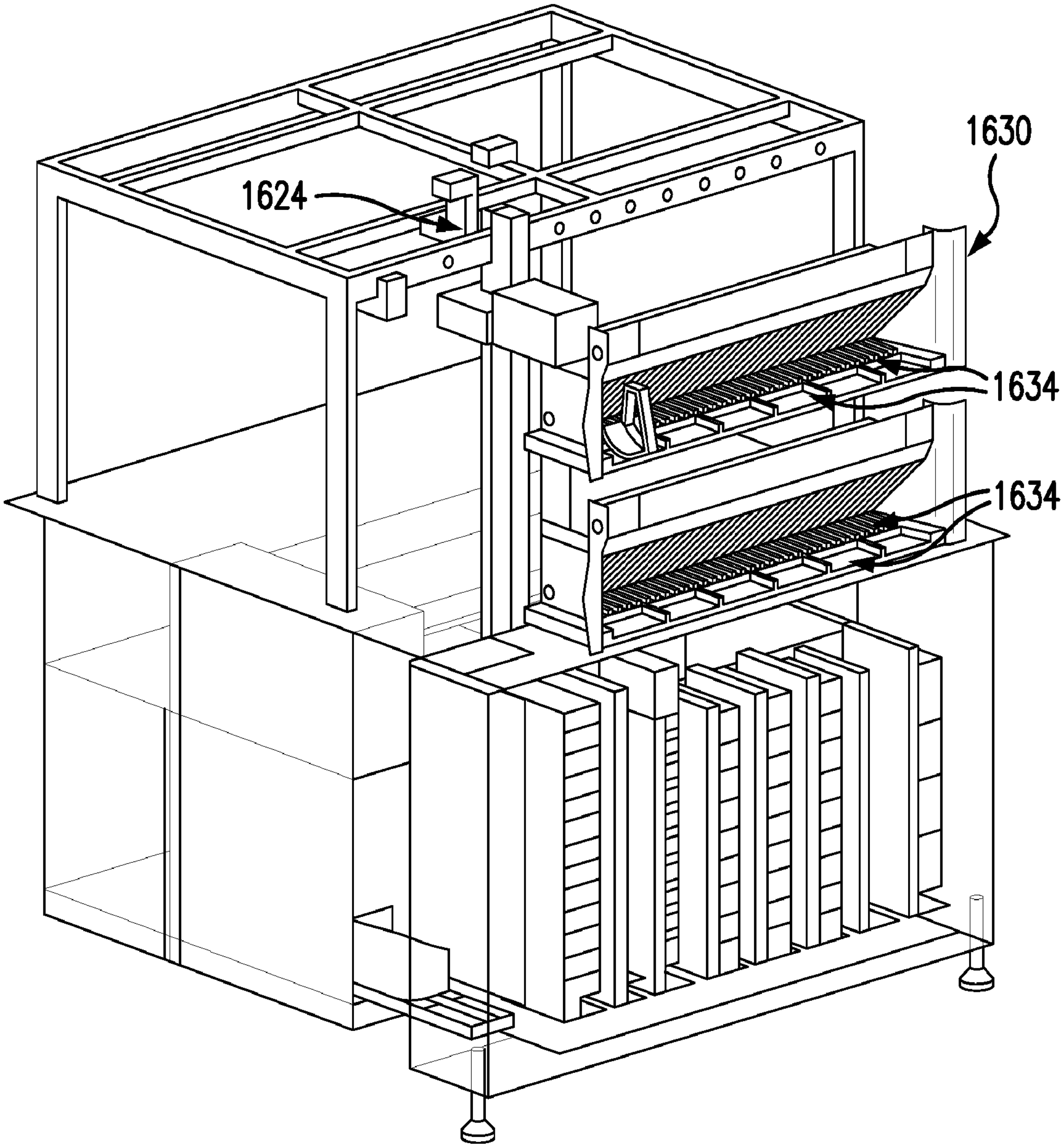
FIG. 2C is a front isometric view of a portion of a sample loading area for use with the exemplary system of FIG. 1A.

For purpose of illustration and not limitation, reference is made to the exemplary automated system 1000 depicted in FIGS. 2A-2C. The automated system 1000 includes a sample loading area 1100 for receiving a plurality of sample tubes 1110. For purpose of example and as embodied herein, tubes 1110 can be stored in sample tube racks 1130 and the sample loading area 1100 can include shuttles 1120, which can transport sample tube racks 1130 having sample tubes 1110 therein to an area for access by the at least one pipettor 1300. Additionally or alternatively, the sample loading area 1100 can include additional component for loading and storing tubes and samples. For example and with reference to FIG. 2C, sample tubes in a sample tube rack can be loaded onto the system at a loading bay 1630. For purpose of example and as embodied herein, each sample tube rack can hold five sample tubes. The loading bay 1630 can include a plurality of locations 1634 for receiving sample tube racks. Operators can load multiple sample tube racks onto the system for further processing. As embodied herein, the loading bay 1630 comprises two levels for receiving sample racks with each having thirty positions for receiving sample tube racks. As embodied herein, where there are five sample tubes per sample tube rack, the loading bay can receive up to 60 sample tube racks and up to 300 sample tubes. The loading bay 1630 can have different configurations including having one or three or more levels to receive additional sample tube racks.

For example and as embodied herein, the sample loading area 1100 can include a robotic sample handler 1624, which can transport sample tube racks from the loading bay 1630 for further processing. For example, and as embodied herein, the robotic sample handler 1624 can pick up a sample tube rack from a position on the loading bay 1630 and place it onto a shuttle 1120 where a sample tube rack 1130 can be moved between the handoff position from the robotic sample handler 1624 to an aspiration position for access by the at least one pipettor 1300.

Additionally or alternatively, sample loading areas can include one or more interfaces to a laboratory automation system (LAS), such as for example a LAS that transports sample tubes around the laboratory to different analyzers. As embodied herein, the at least one pipettor can aspirate samples from sample tubes at the LAS for onboard pooling and high-throughput analysis.

Additionally or alternatively, systems can be configured to allow for continuous operator access to the loading bay 1630. An exemplary continuous operator access system to allow for continuous access and not requiring stopping the system to add samples and reagents to the system is disclosed in U.S. Pat. No. 9,335,338 and is herein incorporated by reference in its entirety.

The automated system 1000 further includes a sample transport 1200 configured to continually transport individual vessels 1210 along a transport path from a sample dispense position 1250 to a sample capture and transfer position 1240, with intermediate positions 1270 therebetween. For purpose of example and not limitation, sample transports can include conveyors, such as a belt conveyor or a chain conveyor, or a vehicle system, such as an electronic vehicle system. Additionally or alternatively, sample transports can include a serpentine path. Additionally or alternatively, the sample transport can include one or more robotic handlers. Additionally or alternatively, sample transports can include an extrusion. Additionally or alternatively, and as embodied herein, the sample transport 1200 can comprise a carousel. As embodied herein, the carousel can be a sample preparation carousel. For purpose of illustration and not limitation, reference is made to the exemplary sample transport 1200 depicted in FIG. 3. For purpose of example and as embodied herein, the sample transport 1200 can have a generally circular shape when viewed in top view. As embodied herein, the sample transport 1200 can include a plurality of positions 1210 around an outer circumference of the sample transport 1200 capable of holding vessels 1220. For purpose of example and not limitation, the sample transport can include between 5 and 40 positions 1210 for holding vessels 1220. Additionally or alternatively, the sample transport can include between 15 and 30 positions for holding vessels. Additionally or alternatively, and as embodied herein, the sample transport can include 28 positions for holding vessels. The sample transport 1200 can have any suitable dimensions. For purpose of example and not limitation, the sample transport 1200 can be generally circular when viewed in top view. As described further herein, the configuration of the sample transport, including its shape, dimensions, and the number of positions for holding vessels can be selected based on desired system performance.

In accordance with the disclosed subject matter, the sample transport 1200 is configured to continually transport individual vessels along a transport path from a sample dispense position to a sample capture and transfer position, with intermediate positions therebetween. For purpose of example and as embodied herein, the sample transport 1200 can include a sample dispense position 1230, a sample capture and transfer position 1240, and a transport path can be defined along the perimeter of the sample transport 1200 between the sample dispense position 1230 and the sample capture and transfer position 1240. As further embodied herein, the sample transport 1200 can include a plurality of intermediate positions 1250, and the intermediate positions can be located along the transport path between the sample dispense position 1230 and the sample capture and transfer position 1240. The position of the sample dispense position 1230, such as the position of the sample dispense position 1230 relative to other system components, can be selected based on desired system performance. For example and as described further herein, the position of the sample dispense position 1230 can be selected based on desired proximity to other system components, such as pipettors, reagents, and consumables. The position of the sample capture and transfer position 1240 can also be selected based on desired system performance. For example and as embodied herein, the position of the sample capture and transfer position 1240 can be selected based on proximity to additional components in the system 100 for performing high-throughput analysis on the pooled sample. Additionally or alternatively, the position of the sample dispense position 1230 and/or the position of the sample dispense position 1240 can be selected to provide the desired transport path and/or the desired number of intermediate positions.

For purpose of example, and as embodied herein, the sample transport can be configured to transport vessels continually along the transport path in a stepwise or lockstep fashion, and the sample transport can pause at each position along the transport path. The configuration of the lockstep can be selected as desired. As embodied herein, the sample transport can rotate by one position with each lockstep. For purpose of example and as embodied herein, the duration of the lockstep, or the time the sample transport 1200 pauses at each position along the transport path, can be between about 5 and about 40 seconds. Additionally or alternatively, the duration of each lockstep can be between about 15 and about 30 seconds. Additionally or alternatively and as embodied herein, the duration of each lockstep can be about 24 seconds. The duration of the lockstep can be selected based on desired system performance, as described further herein. For example, the duration of the lockstep can be selected based on the number of pipettor operations performed during the lockstep, as described further herein.

Motion of the sample transport 1200 can be controlled using techniques known in the art. For example, an electric motor can be used to rotate the sample transport. Additionally or alternatively, one or more controllers can be used to regulate and/or control movement of the sample transport 1200.

Automated systems in accordance with the disclosed subject matter include at least one pipettor 1300 to transfer a first sample from a first sample tube at the sample loading area 1100 and a second sample from a second sample tube at the sample loading area 1100 to the sample transport 1200 and to pool the first sample and the second sample in a vessel on the sample transport to form a pooled sample. For example and as embodied herein, the at least one pipettor 1300 can include a robotic pipettor, as described further herein. The at least one pipettor can be selected based on desired system performance. For example and illustration and as embodied herein, the at least one pipettor 1300 can have at least three degrees of freedom (e.g., x, y, and z). Additionally or alternatively, the at least one pipettor can include a first robotic pipettor to transfer samples from the sample loading area to the sample transport, and a second robotic pipettor to pool samples on the sample transport. For example and not limitation, the first and second robotic pipettors can each have two degrees of freedom (e.g., theta and z).

Automated systems in accordance with the disclosed subject matter further include a sample transfer mechanism 1400 to capture at least a fractionated portion of the pooled sample from the vessel 1220 at the sample capture and transfer position 1240 and to transfer the at least a fractionated portion of the pooled sample for high-throughput analysis. For purpose of example and not limitation, the sample transfer mechanism can include a pipettor, such as a robotic pipettor. Additionally or alternatively, and as embodied herein, the sample transfer mechanism can include a magnetic tip, which can capture magnetic microparticles from the pooled sample having nucleic acids or antigens bound to, as described further herein.

2. Exemplary Methods for Onboard Pooling on a Sample Transport

Figure 4B:
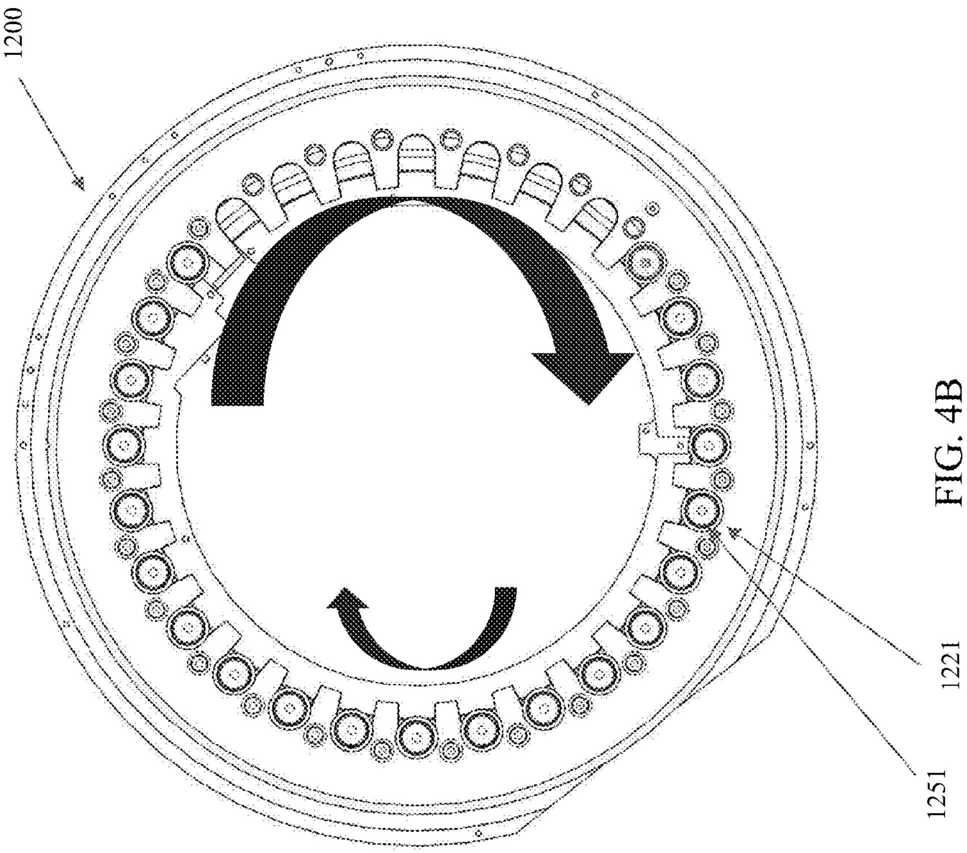
FIG. 4A-4B are schematic top views of the sample transport from the exemplary system of FIG. 2A illustrating pooling of a first sample and a second sample in a vessel on the sample transport in accordance with an aspect of the disclosed subject matter.
Figure 4A:
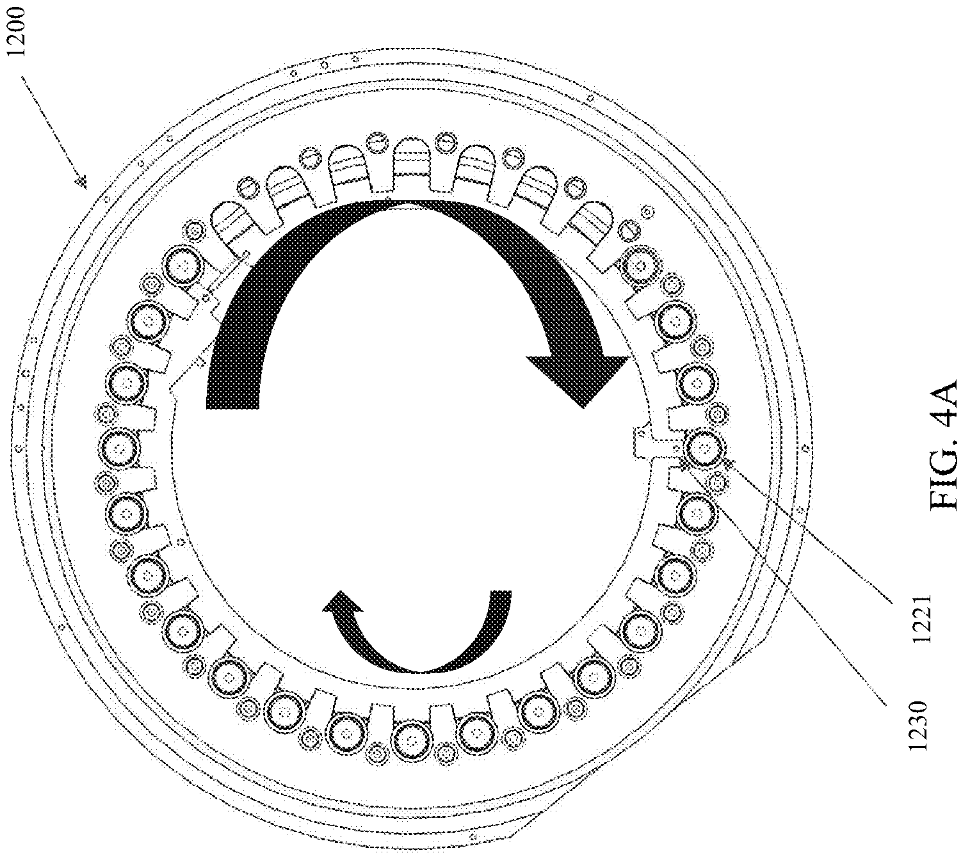

Systems and methods for onboard pooling in accordance with the disclosed subject matter include pooling at least first and second samples in a vessel on the sample transport. For purpose of example and not limitation, and with reference to the exemplary sample transport 1200 depicted in FIGS. 4A-4B, pooling the first sample and the second sample on the sample transport 1200 can include transferring the first sample from a first sample tube at the sample loading area 1100 and the second sample from a second sample tube at the sample loading area to a first vessel 1221 at the sample dispense position 1230 to combine the first and second samples in the first vessel 1221 prior to the sample transport transporting the first vessel 1221 and the pooled sample to a first intermediate position 1251. For purpose of example and as embodied herein, the sample transport 1200 can move in a lockstep fashion as described above, and with reference to FIGS. 4A and 4B, the at least one pipettor 1300 can transfer a first sample from a first sample tube at the sample loading area 1100 to a first vessel 1221 at sample dispense position 1230. As further embodied herein, the at least one pipettor 1300 can transfer a second sample from a second sample tube at the sample loading area 1100 to the first vessel 1221 at sample dispense position 1230 prior to the sample transport 1200 transporting the first vessel 1221 to a first intermediate position 1251. The pooled first and second samples in the first vessel 1221 can then be transported along the transport path to the sample capture and transfer position 1240, where at least a fractionated portion of the pooled sample can be transferred for high-throughput analysis.

For purpose of example and not limitation, the first and second samples transferred to the first vessel 1221 at sample dispense position 1230 can be pooled samples. For example and not limitation, the first and second samples can each include a pool of up to 48 samples. For example and as embodied herein, the first and second samples can each include a pool of 48 samples. As described further herein, the first and second samples can each be a pooled sample, such as a pooled sample that was prepared on a liquid handler or pooler prior to introduction to the sample loading area 1100. Additionally or alternatively, the first and second samples can each be an individual donor sample.

In accordance with an aspect of the disclosed subject matter, the disclosed automated systems and methods for onboard pooling can include combining and pooling additional samples in the first vessel 1221. For purpose of example and illustration, reference is made to FIG. 5A, which depicts the exemplary sample transport 1200 with a first vessel 1221 containing a first sample and a second sample therein. For purpose of example and as embodied herein, a third sample and a fourth sample can be combined with the first sample and second sample in the first vessel 1221 to add the third and fourth samples to the pooled sample. As embodied herein, pooling the samples can include transferring the third sample from a third sample tube at the sample loading area 1100 and a fourth sample from a fourth sample tube at the sample loading area 1100 to the first vessel 1221 at the first intermediate position 1251. The pooled first, second, third, and fourth samples in the first vessel 1221 can then be transported along the transport path to the unload position 1240, where at least a fractionated portion of the pooled sample can be transferred for high-throughput analysis.

Figure 5A:
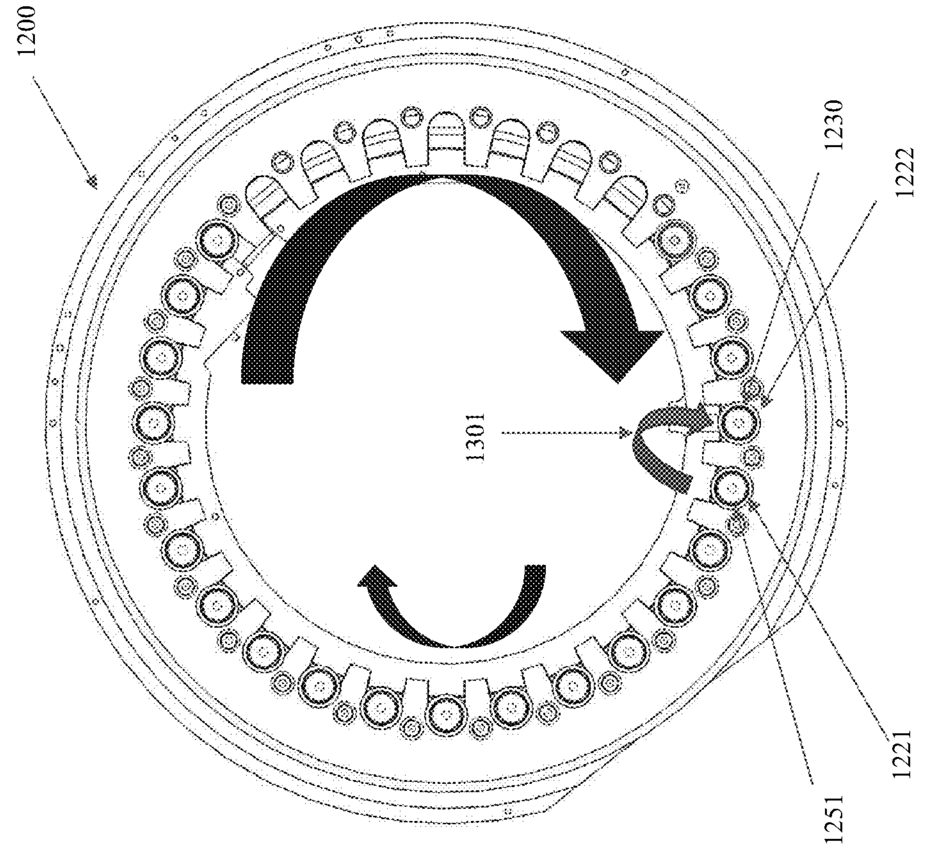
FIG. 5A is a schematic top view of the sample transport from the exemplary system of FIG. 2A illustrating pooling of a third sample and a fourth sample in accordance with an aspect of the disclosed subject matter.
Figure 5B:
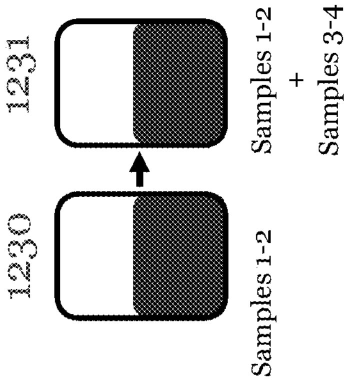
FIG. 5B is a schematic side cross-sectional view of a first vessel at a sample dispense position and a first intermediate position, respectively, on the sample transport of the exemplary system of FIG. 2A in accordance with an aspect of the disclosed subject matter.
Figure 6B:
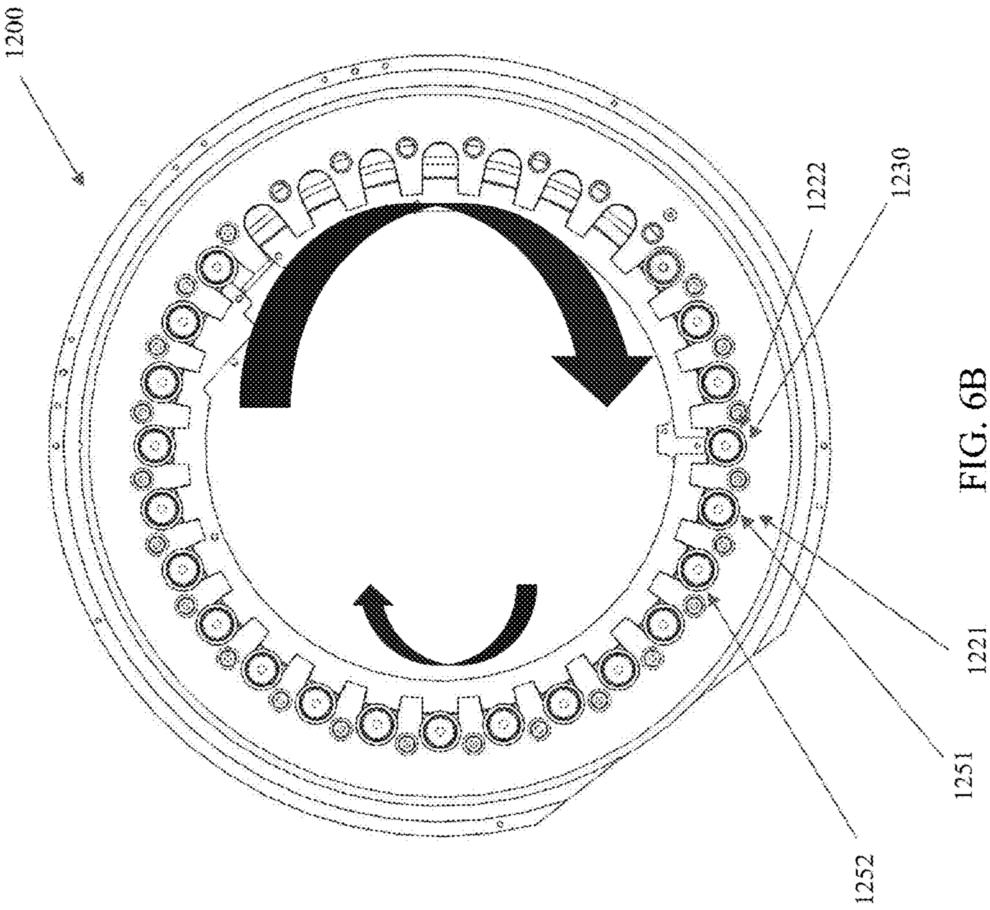
FIGS. 6A-6C are schematic top views of the sample transport from the exemplary system of FIG. 2A illustrating a pre-treatment process and pooling of pre-treated samples in accordance with another aspect of the disclosed subject matter.
Figure 6A:
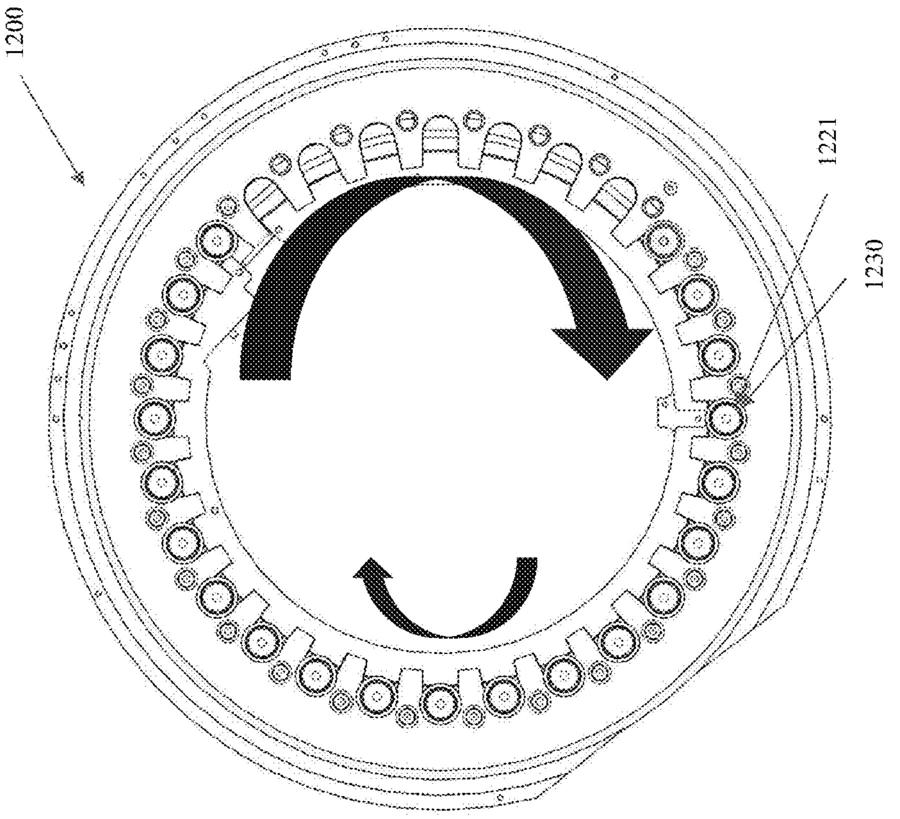
Figure 6C:
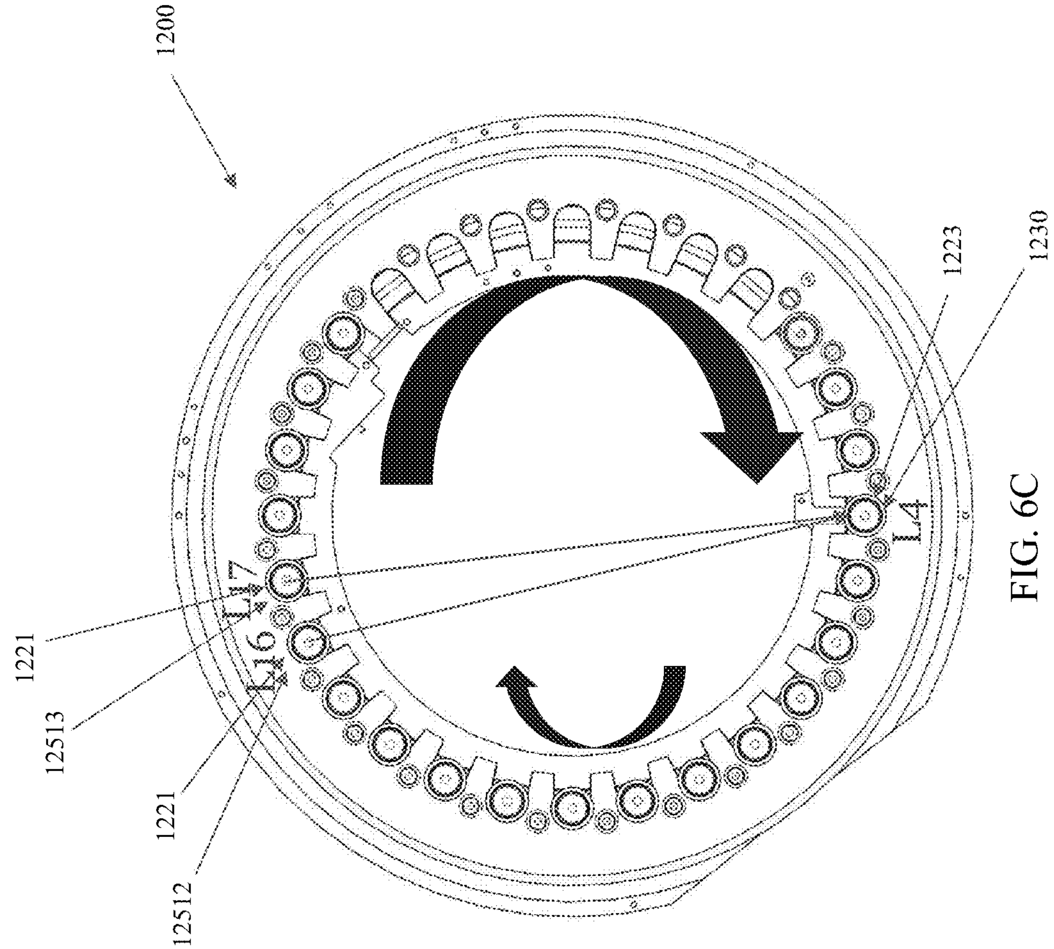

Additionally or alternatively, and as embodied herein, the pooled first, second, third, and fourth samples in the first vessel 1221 can be transferred from the first vessel 1221 to a second vessel 1222 at the sample dispense position 1230 as represented in FIG. 5A by arrow 1301. For purpose of example and as embodied herein, the pooled sample can be transferred from the first vessel 1221 to a second vessel 1222 at the sample dispense position 1230 to initiate an additional sample preparation process for the pooled sample. The additional sample preparation process can include, for example, a lysis process as described further herein. As embodied herein, additional sample preparation processes, such as lysis processes, can be performed on the sample transport 1200.

For example and as embodied herein, samples can be pooled in the first vessel 1221 as the first vessel is transported along the transport path and the first vessel 1221 can have only the pooled samples therein. Additionally or alternatively, and as further embodied herein, the at least one pipettor 1300 can transfer the pooled samples from the first vessel 1221 at the first intermediate position 1251 to the second vessel 1222 at the sample dispense position 1230. For purpose of example, and as described further herein, the first, second, third, and fourth samples can be combined in the first vessel 1221, and the pooled sample can then be transferred to a second vessel 1222 with one or more reagents at the sample dispense position 1230 to initiate a further sample preparation process for the pooled sample. As embodied herein, the pooled sample and reagents can then be transported along the transport path to the unload position

1240, where at least a fractionated portion of the pooled sample can be transferred for high-throughput analysis.

Samples can be transferred between vessels on the sample transport 1200 using pipettor 1300. For example and as embodied herein, the pipettor can use disposable tips to aspirate and dispense samples. For purpose of example and illustration, pipettor 1300 can aspirate the pooled first, second, third, and fourth samples from the first vessel 1221 at the first intermediate position 1251 and dispense the pooled sample into the second vessel 1222 at the sample dispense position 1230 using one disposable pipette tip. Additionally or alternatively, the first, second, third, and fourth samples can be pooled in the second vessel 1222 at the sample dispense position. For example, with the first vessel 1221 having the pooled first and second samples at the first intermediate position 1251, the pipettor 1300 can aspirate the third sample from its sample container at the sample loading area and transfer the third sample to the second vessel 1222 at the sample dispense position 1230 using a first tip. The pipettor can then dispose of the first tip, pick up a second disposable tip and aspirate the fourth sample from its sample container at the sample loading area. The pipettor can then use the same disposable tip to further aspirate the first and second samples from the first vessel 1221 at the first intermediate position 1251. The pipettor can then dispense the first, second, and fourth samples into the second vessel 1222 at the sample dispense position to pool the first, second, third, and fourth samples in the second vessel 1222. Additionally or alternatively, other pipettor movement patterns can be used to pool samples on the sample transport 1200, as further described herein.

Additionally or alternatively, and as further embodied herein, additional samples can be pooled. For example and not limitation, additional samples can be transferred from respective sample tubes at the sample loading area 1100 to the sample transport 1200 and pooled in the first vessel 1221. For example, additional samples can be transferred from respective sample tubes at the sample loading area 1100 to the first vessel 1221 at the sample dispense position 1230 prior to the sample transport transporting the first vessel 1221 to the first intermediate position 1251. Additionally or alternatively, additional samples can be transferred from respective sample tubes at the sample loading area 1100 to the first vessel 1221 at the first intermediate position 1251 prior to the sample transport transporting the first vessel 1221 from the first intermediate position 1251 to a second intermediate position 1252. Additionally or alternatively, additional samples can be transferred from respective sample tubes at the sample loading area 1100 to the first vessel 1221 at other intermediate positions along the transport path. For example and not limitation, one sample can be transferred from a sample tube at the sample loading area 1100 to the first vessel 1221 at each intermediate position. Additionally or alternatively, two samples can be transferred from respective sample tubes at the sample loading area 1100 to the first vessel 1221 at each intermediate position. Additionally or alternatively, three samples can be transferred from respective sample tubes at the sample loading area 1100 to the first vessel 1221 at each intermediate position. Additionally or alternatively, four samples can be transferred from respective sample tubes at the sample loading area 1100 to the first vessel 1221 at each intermediate position. The number of samples added to the pooled sample at each position of the sample transport can be selected based on desired system performance.

For purpose of example and not limitation, between 2 and 100 samples can be pooled in the first vessel 1221 on the sample transport as the first vessel is transported along the transport path. Additionally or alternatively, between 2 and 50 samples can be pooled in the first vessel 1221 on the sample transport as the first vessel 1221 is transported along the transport path. Additionally or alternatively, between 2 and 30 samples can be pooled in the first vessel 1221 on the sample transport as the first vessel 1221 is transported along the transport path. Additionally or alternatively, and as embodied herein, between 2 and 24 samples can be pooled in the first vessel 1221 on the sample transport as the first vessel 1221 is transported along the transport path.

Additionally or alternatively, a pooled sample can include samples from two donors. In certain embodiments, the pooled sample comprises samples from three donors. In certain embodiments, the pooled sample comprises samples from four donors. In certain embodiments, the pooled sample comprises samples from five donors. In certain embodiments, the pooled sample comprises samples from six donors. In certain embodiments, the pooled sample comprises samples from seven donors. In certain embodiments, the pooled sample comprises samples from eight donors. In certain embodiments, the pooled sample comprises samples from nine donors. In certain embodiments, the pooled sample comprises samples from 10 donors. In certain embodiments, the pooled sample comprises samples from 11 donors. In certain embodiments, the pooled sample comprises samples from 12 donors. In certain embodiments, the pooled sample comprises samples from 13 donors. In certain embodiments, the pooled sample comprises samples from 14 donors. In certain embodiments, the pooled sample comprises samples from 15 donors. In certain embodiments, the pooled sample comprises samples from 16 donors. In certain embodiments, the pooled sample comprises samples from 17 donors. In certain embodiments, the pooled sample comprises samples from 18 donors. In certain embodiments, the pooled sample comprises samples from 19 donors. In certain embodiments, the pooled sample comprises samples from 20 donors. In certain embodiments, the pooled sample comprises samples from 21 donors. In certain embodiments, the pooled sample comprises samples from 22 donors. In certain embodiments, the pooled sample comprises samples from 23 donors. In certain embodiments, the pooled sample comprises samples from 24 donors. In certain embodiments, the pooled sample comprises samples from 25 donors. In certain embodiments, the pooled sample comprises samples from 26 donors. In certain embodiments, the pooled sample comprises samples from 27 donors. In certain embodiments, the pooled sample comprises samples from 28 donors. In certain embodiments, the pooled sample comprises samples from 29 donors. In certain embodiments, the pooled sample comprises samples from 30 donors. In certain embodiments, the pooled sample comprises samples from 31 donors. In certain embodiments, the pooled sample comprises samples from 32 donors. In certain embodiments, the pooled sample comprises samples from 33 donors. In certain embodiments, the pooled sample comprises samples from 34 donors. In certain embodiments, the pooled sample comprises samples from 35 donors. In certain embodiments, the pooled sample comprises samples from 36 donors. In certain embodiments, the pooled sample comprises samples from 37 donors. In certain embodiments, the pooled sample comprises samples from 38 donors. In certain embodiments, the pooled sample comprises samples from 39 donors. In certain embodiments, the pooled sample comprises samples from 40 donors. In certain embodiments, the pooled sample comprises samples from 41 donors. In certain embodiments, the pooled sample comprises samples from 42 donors. In certain embodiments, the pooled sample comprises samples from 43 donors. In certain embodiments, the pooled sample comprises samples from 44 donors. In certain embodiments, the pooled sample comprises samples from 45 donors. In certain embodiments, the pooled sample comprises samples from 46 donors. In certain embodiments, the pooled sample comprises samples from 47 donors. In certain embodiments, the pooled sample comprises samples from 48 donors. In certain embodiments, the pooled sample comprises samples from 49 donors. In certain embodiments, the pooled sample comprises samples from 50 donors. In certain embodiments, the pooled sample comprises samples from 51 donors. In certain embodiments, the pooled sample comprises samples from 52 donors. In certain embodiments, the pooled sample comprises samples from 53 donors. In certain embodiments, the pooled sample comprises samples from 54 donors. In certain embodiments, the pooled sample comprises samples from 55 donors. In certain embodiments, the pooled sample comprises samples from 56 donors. In certain embodiments, the pooled sample comprises samples from 57 donors. In certain embodiments, the pooled sample comprises samples from 58 donors. In certain embodiments, the pooled sample comprises samples from 59 donors. In certain embodiments, the pooled sample comprises samples from 60 donors. In certain embodiments, the pooled sample comprises samples from 61 donors. In certain embodiments, the pooled sample comprises samples from 62 donors. In certain embodiments, the pooled sample comprises samples from 63 donors. In certain embodiments, the pooled sample comprises samples from 64 donors. In certain embodiments, the pooled sample comprises samples from 65 donors. In certain embodiments, the pooled sample comprises samples from 66 donors. In certain embodiments, the pooled sample comprises samples from 67 donors. In certain embodiments, the pooled sample comprises samples from 68 donors. In certain embodiments, the pooled sample comprises samples from 69 donors. In certain embodiments, the pooled sample comprises samples from 70 donors. In certain embodiments, the pooled sample comprises samples from 71 donors. In certain embodiments, the pooled sample comprises samples from 72 donors. In certain embodiments, the pooled sample comprises samples from 73 donors. In certain embodiments, the pooled sample comprises samples from 74 donors. In certain embodiments, the pooled sample comprises samples from 75 donors. In certain embodiments, the pooled sample comprises samples from 76 donors. In certain embodiments, the pooled sample comprises samples from 77 donors. In certain embodiments, the pooled sample comprises samples from 78 donors. In certain embodiments, the pooled sample comprises samples from 79 donors. In certain embodiments, the pooled sample comprises samples from 80 donors. In certain embodiments, the pooled sample comprises samples from 81 donors. In certain embodiments, the pooled sample comprises samples from 82 donors. In certain embodiments, the pooled sample comprises samples from 83 donors. In certain embodiments, the pooled sample comprises samples from 84 donors. In certain embodiments, the pooled sample comprises samples from 85 donors. In certain embodiments, the pooled sample comprises samples from 86 donors. In certain embodiments, the pooled sample comprises samples from 87 donors. In certain embodiments, the pooled sample comprises samples from 88 donors. In certain embodiments, the pooled sample comprises samples from 89 donors. In certain embodiments, the pooled sample comprises samples from 90 donors. In certain embodiments, the pooled sample comprises samples from 91 donors. In certain embodiments, the pooled sample comprises samples from 92 donors. In certain embodiments, the pooled sample comprises samples from 93 donors. In certain embodiments, the pooled sample comprises samples from 94 donors. In certain embodiments, the pooled sample comprises samples from 95 donors. In certain embodiments, the pooled sample comprises samples from 96 donors. In certain embodiments, the pooled sample comprises samples from 97 donors. In certain embodiments, the pooled sample comprises samples from 98 donors. In certain embodiments, the pooled sample comprises samples from 99 donors. In certain embodiments, the pooled sample comprises samples from 100 donors. In certain embodiments, the pooled sample comprises samples from 2-1,000 donors. In certain embodiments, the pooled sample comprises samples from 2-500 donors. In certain embodiments, the pooled sample comprises samples from 2-250 donors. In certain embodiments, the pooled sample comprises samples from 2-150 donors. In certain embodiments, the pooled sample comprises samples from 2-100 donors. In certain embodiments, the pooled sample comprises samples from 25-100 donors. In certain embodiments, the pooled sample comprises samples from 50-100 donors. In certain embodiments, the pooled sample comprises samples from 75-100 donors. In certain embodiments, the pooled sample comprises samples from more than 100 donors.

Pool size can be selected as desired. For purpose of example and not limitation, pool size can be selected based on the prevalence in a population being tested of a disease, pathogen, or infectious agent being tested for. Additionally or alternatively, pool size can be selected based on local regulations. Additionally or alternatively, pool size can be selected based on desired deconstruction times. Additionally or alternatively, pool size can be selected according to the sensitivity of the analytical technique to be used for high-throughput analysis. For purpose of example, as the number of samples within a pool increases for a given pooled sample volume, the volume of liquid from each constituent sample of the pool is reduced. The reduced volume of each constituent sample in the pooled sample can be relevant, for example, when performing analysis on the pooled sample to identify one or more pathogens or infectious agents. For example, if a single sample in the pool includes the pathogen or infectious agent, the amount of the pathogen or infectious agent in the pool can be reduced as the number of samples in the pool is increased. Different analysis techniques can have different sensitivities and can detect pathogens or infectious agents at different amounts in a pooled sample. Accordingly, pool size can be selected according to the sensitivity of the analysis to be performed.

Additional considerations for selecting pool size can include but are not limited to, the volume of the pooled sample to be analyzed. For example, the volume of the pooled sample can be increased to accommodate larger pool sizes. For example, with pooled samples of a larger volume, a larger volume of each constituent sample can be included in the pooled sample. For purpose of example and as embodied herein, the size of pipette tips, lysis tubes, and/or amplification and detection vessels can be selected according to the desired pooled sample volume and pool size for high-throughput analysis. Additionally or alternatively, additional system parameters can be adjusted to achieve a desired pool size. For example, the duration of a lockstep can be increased to allow additional time for movement of the at least one pipettor between movements of the sample transport, which can provide additional time for the at least one pipettor to pool additional samples. Additionally or alternatively, the speed of the at least one pipettor can be increased. Additionally or alternatively, the at least one pipettor can include two or more pipette channels For purpose of example and not limitation, systems and methods in accordance with the disclosed subject matter can be used to form pools having a wide range of pool sizes. For purpose of example and not limitation, systems and methods in accordance with the disclosed subject matter can be used to provide different pool sizes for different samples and/or different analyses. For example and not limitation, systems and methods in accordance with the disclosed subject matter can be used to form larger pool sizes, such as for analysis with higher sensitivity, such as nucleic acid analysis, and to form smaller pool sizes, such as for analysis with lower sensitivity, such as immunoassay analysis.

2.1. Pre-Treatment Process

In accordance with another aspect of the disclosed subject matter, a sample pre-treatment process can be performed before onboard pooling and pre-treated samples can be pooled on the sample transport. For purpose of example and not limitation, samples on the sample transport can be transported along the transport path to pre-treat the samples prior to pooling the samples on the sample transport. Onboard pooling can be used with a range of sample pre-treatments to pool pre-treated samples. For example, a sample pre-treatment can include dilution of a sample and/or combination of a sample with one or more reagents. For purpose of example and as embodied herein, the sample pre-treatment process can include a pre-treatment lysis process. As embodied herein, after the pre-treatment process, the sample lysates can be pooled on the sample transport. As embodied herein, the sample pre-treatment process, onboard pooling, and additionally or alternatively additional sample preparation processes can be performed on the sample transport.

For purpose of example and as embodied herein, a pre-treatment step can be performed on samples (e.g., whole blood) prior to the pooling the samples. Exemplary operations regarding the pre-treatment process are provided in Table 1 below.

TABLE 1

| Pos. | Function |
|---|---|
| L1 | Load Lysis Tube in Carousel<br>Load Transfer Tip in Carousel |
| L2 | Dispense Lysis Buffer |
| L3 | |
| L4 | Dispense Sample<br>Dispose of Tip |
| L5-L16 | Incubation and Mixing |
| L17 | Aspirate Sample 1 from L17<br>Aspirate Sample 2 from L16<br>Dispense Samples 1 and 2 to L4<br>Dispose of Tip |

In the present embodiment, exemplary position L1 corresponds to the loading of a new vessel onto the sample transport 1200. As embodied herein the vessel can be a lysis tube. In certain embodiments, loading is accomplished by known "Pick & Place" strategies from a loadable stack. L2 corresponds to a lysis buffer dispensing position where lysis buffer and/or other reagents can be dispensed into the vessel. L4 corresponds to a sample dispensing position 1230.

For purpose of example and illustration reference is made to FIGS. 6A-6D. As embodied herein, a sample pre-treatment process can include transferring a first sample to a first vessel 1221 at the sample dispense position 1230 prior to the sample transport 1200 transporting the first vessel 1221 to a first intermediate position 1251. As embodied herein a second sample can then be transferred to a second vessel 1222 at the sample dispense position 1230. As embodied herein, the first vessel 1221 and the second vessel 1222 can each include a reagent. The pre-treatment process can further include continually transporting the first vessel 1221 and the second vessel 1222 along the transport path. As described further herein, samples can be transported along the transport path for a period of time sufficient to achieve the desired pre-treatment. For purpose of example and as embodied herein, the first and second samples can include whole blood samples and the reagent can include a lysis buffer. As embodied herein, the pre-treatment process can include lysing the first and second samples. For purpose of example and as embodied herein, the pre-treatment process can include lysing samples on the sample transport for between about 3 minutes and about 6 minutes. For example and not limitation and as embodied herein, the pre-treatment process can include mixing the first vessel and the second vessel at each intermediate position. Exemplary mixing systems for mixing the contents of vessels on the sample transport 1200 are described further herein.

As further embodied herein, pre-treated samples can be pooled on the sample transport 1200. For example and as embodied herein, the first and second samples can be transferred from the first vessel 1221 and second vessel 1222 at respective intermediate positions to a third vessel 1223 at the sample dispense position to pool the first sample and the second sample in the third vessel 1223. For example and as embodied herein, the pipettor 1300 can transfer the first sample from the first vessel 1221 at a thirteenth intermediate position 12513 to the third vessel 1223 at the sample dispense position 1230 and the second sample from the second vessel 1222 at a twelfth intermediate position 12512 to the third vessel 1223 at the sample dispense position 1230. The first and second samples can be transferred individually or together. For example, the pipettor 1300 can transfer the first sample from the first vessel 1221 to the third vessel 1223 using a first disposable pipette tip and the second sample from the second vessel 1222 to the third vessel 1223 using a second disposable pipette tip. Additionally or alternatively, the first sample can be aspirated from the first vessel 1221 in a first disposable pipette tip and the second sample can be aspirated from the second vessel 1222 in the same disposable pipette tip. The first and second samples can then be dispensed together into the third vessel 1223.

Pre-treatment and onboard pooling of pre-treated samples can be used with a wide range of pool sizes. For example and not limitation, between 2 and 20 pre-treated samples can be pooled. Additionally or alternatively, between 2 and 10 pre-treated samples can be pooled. Additionally or alternatively, between 2 and 6 pre-treated samples can be pooled.

Although reference has been made herein to a lysis pre-treatment, additional or alternative sample pre-treatment process can be incorporated. For example and not limitation, a sample pre-treatment can include dilution of a sample and/or combination of a sample with one or more reagents.

3. Onboard Deconstruction

As described further herein, automated systems and methods in accordance with the disclosed subject matter can be used, for example and not limitation, to detect the presence of one or more pathogens or infectious agents in pooled samples. According to an aspect of the disclosed subject matter, the disclosed automated systems and methods can further be used for onboard deconstruction of pooled samples, such as to identify which of the samples used to form a pooled sample includes a pathogen or infectious agent detected in the pooled sample. The term "deconstruction" as used herein is a broad term, and is to be given its ordinary and customary meaning to a person of skill in the art (and it is not to be limited to a special or customized meaning), and refers without limitation to a process of identifying the reactive constituent sample(s) of a reactive pooled sample, either by individual testing (IDT) or in multiple steps using sub-pools. Automated systems and methods in accordance with the disclosed subject matter can deconstruct pooled samples quickly and efficiently. In certain embodiments, the systems and methods disclosed herein can deconstruct pooled samples without manual intervention.

For example and as embodied herein, the samples used to form a pooled sample can be stored onboard, such as in the sample loading area, during high-throughput analysis of the pooled sample. For example and not limitation samples used to form a pooled sample can be stored onboard in sample loading area 1100 of the exemplary system 1000, The samples used to form a pooled sample can then be automatically transferred from the loading area to the sample transport for further high-throughput analysis if deconstruction of the pooled sample is required. Additionally or alternatively, the onboard pooling systems and methods described herein can be used to form custom pool sizes, which can facilitate more efficient pool deconstruction as described further herein.

For purpose of example and as embodied herein, high-throughput analysis of a pooled sample can include a qualitative assay on the at least a fractionated portion of the pooled sample to detect a plurality of pathogens or infectious agents in the pooled sample. As embodied herein, upon detection of a pathogen or infectious agent in the pooled sample, onboard deconstruction of the pooled sample can be performed to determine which of the first sample, the second sample, or any additional sample in the pooled sample, includes the pathogen or infectious agent.

For example and not limitation, the qualitative assay can include a nucleic acid analysis of the pooled sample. As embodied herein, upon a determination of the presence of a nucleic acid derived from at least one of a plurality of pathogens or infectious agents in the pooled sample, nucleic acid analysis can be performed on individual samples or sub-pools thereof that were used to form the pooled sample. As further embodied herein, based at least in part on the nucleic acid analysis of the individual samples or sub-pools thereof, a determination can be made as to whether donor material associated with each individual sample or sub-pool thereof is acceptable for clinical use.

As embodied herein, onboard deconstruction of a pooled sample can include forming sub-pools, with each sub-pool being formed of a subset of the samples used to form the pooled sample. Onboard deconstruction can include further include performing a qualitative assay on each sub-pool to determine which sub-pool includes the pathogen or infectious agent. The size and number of sub-pools used for onboard deconstruction can be chosen to maximize deconstruction efficiency. For example and as embodied herein, the high-throughput analysis of the pooled sample can include identification of a positive or reactive pooled sample and can further include onboard pooling of a subset of the plurality of samples included in the pooled sample on the sample transport to form a sub-pool high-throughput analysis of the sub-pool. In certain embodiments, the high-throughput analysis can include nucleic acid analysis.

For purpose of example and illustration, exemplary pool deconstruction techniques are shown in FIGS. 7A-7F. With reference to FIG. 7A, as pool size increases, pool deconstruction efficiency can be improved by using one or more rounds of sub-pool testing to deconstruct the pooled sample. For example, and as shown in FIG. 7A, using one or more rounds of sub-pool testing can reduce the number of tests needed to deconstruct a sample. For example, a pooled sample of 24 can be deconstructed using three rounds of deconstruction testing and 9 total tests. Alternatively, a pooled sample of 24 can be deconstructed using two rounds of deconstruction testing (i.e., one round of sub-pool testing followed by IDT testing) and 10 total tests. Additionally or alternatively, a pooled sample of 24 can be deconstructed using only individual, i.e., IDT testing and 24 total tests.

Although using one or more rounds of sub-pool testing can improve deconstruction efficiency, conventional deconstruction methods often incorporate only a single round of sub-pool testing, or no sub-pool testing. For example, pooling samples to form a pooled sample or a sub-pool of the pooled sample conventionally can be performed on a dedicated liquid handler. Forming sub-pools for deconstruction of a pooled sample can include manually retrieving and transferring the constituent samples used to form the pooled sample to a liquid handler to be pooled into sub-pools and then manually transferring the sub-pools to an instrument for analysis. In conventional deconstruction, the process of manually transferring constituent samples to and from a liquid handler can then be repeated to form additional sub-pools for additional rounds of deconstruction testing. The additional time and complexity associated with using a dedicated liquid handler to form sub-pools for deconstruction can outweigh the benefits of using additional rounds of deconstruction testing, and as such, conventional deconstruction methods can be limited to a single round of sub-pool testing. Additionally or alternatively, conventional deconstruction testing can include only IDT testing for deconstruction.

Automated systems and methods for onboard pooling in accordance with the disclosed subject matter can increase deconstruction efficiency. For purpose of example and as embodied herein, the constituent samples used to form a pooled sample can be stored at the sample loading area during high-throughput analysis of the pooled sample, and upon a determination that the pooled sample is reactive, the system can automatically initiate further onboard pooling and/or high-throughput analysis of the constituent samples to deconstruct the pooled sample. Additionally or alternatively, sub-pool size and the number of rounds of sub-pool testing can be selected to maximize deconstruction efficiency.

In addition to providing advantages for deconstruction, the automated systems and methods for onboard pooling in accordance with the disclosed subject matter can support multiple rounds of high-throughput analysis, including high-throughput analyses with different pool size requirements. For example and as described above, different pool sizes can be used for different analysis techniques. For purpose of example and illustration, a first analysis can be performed using a first pool of 24 samples, and the samples used to form the first pool can remain onboard during the first analysis. When the first analysis has been completed, a second analysis can be performed on the 24 samples used to form the first pool. For example and illustration, 12 pools of 2 can be formed and the second analysis can be performed on the 12 pools of 2. For purpose of example and illustration and not limitation, the first analysis can be a nucleic acid analysis and the second analysis can be an immunoassay analysis.

4. High-Throughput Analysis

In accordance with the disclosed subject matter, automated systems and methods for onboard pooling and high-throughput analysis include high-throughput analysis of at least a fractionated portion of a pooled sample. The high-throughput analysis can include one or more analyses as known in the art for analyzing biological samples. For purpose of example and not limitation, the high-throughput analysis can include a qualitative assay on the at least a fractionated portion of the pooled sample to detect one or more pathogen or infectious agent. For purpose of example and not limitation, the one or more pathogen or infectious agent can be selected from the group consisting of: SARS-COV-2 (COVID-19), HIV-1, HIV-2, HBV, HCV, CMV, Parvo B19 Virus, HAV, *Chlamydia*, Gonorrhea, WNV, Zika Virus, Dengue Virus, Chikungunya Virus, Influenza, *Babesia*, Malaria, and HEV.

Additionally or alternatively, the high-throughput analysis can include an immunoassay analysis on the at least a fractionated portion of the pooled sample. For purpose of example and not limitation, the immunoassay analysis can include a digital immunoassay analysis. Additionally or alternatively, and as embodied herein, the high-throughput analysis can include a nucleic acid analysis on the at least a fractionated portion of the pooled sample. Additionally or alternatively, the high-throughput analysis can include one or more analyses known in the art for analyzing biological samples, such as for example, clinical chemistry, and/or spectrophotometry. As described herein, the volume of the pooled sample for analysis, the number of samples included in the pooled sample, and other aspects of the systems and method described herein can be selected to provide a sample suitable for the desired analysis technique.

In certain embodiments, the high-throughput analysis can further include determining a result. As discussed herein the term "result" is a broad term, and is to be given its ordinary and customary meaning to a person of skill in the art (and it is not to be limited to a special or customized meaning), and can refer without limitation to a determination of the presence or absence of an analyte of interest in the pooled sample. For example and not limitation, and as embodied herein, a result can include the detection of the presence of one or more target nucleic acids. In certain embodiments, a result can include determining the absence of one or more target nucleic acids.

The onboard pooling and high-throughput analysis methods and systems described herein find use in a wide variety of indications and operational arrangements. For example, but not by way of limitation, the methods and systems described herein find use in the screening of donor samples, such as donor blood, for the release of donor material associated with the donor sample for clinical use. For example, donor material can be held, often for extended periods of time, while samples related to the donor material are screened for the presence of one or more pathogens or infectious agents. Generally, such donor material, such as donor blood, is released for clinical use only upon the completion of such screening, which can also include additional screening aspects, e.g., HLA typing and blood group identification, among other potential screening steps. Thus, the onboard pooling and high-throughput analysis methods and systems of the present disclosure can be particularly adapted, via specific performance attributes, e.g., time to result and throughput per unit size of the systems, to accelerate the release of such samples. In addition, the methods and systems of the present disclosure also provide process options for screening of the samples, e.g., prioritizing specific samples and/or the screening of specific pathogens or infectious agents, that can operationally enhance donor and patient safety and access. Additionally or alternatively, the methods and systems described herein can find use in diagnostic applications, such as for example COVID-19 testing and pooling of COVID-19 samples for high-throughput analysis, medical demographics, epidemiology, and/or in population health studies. For example and not limitation, the methods and systems for onboard pooling described herein can find use in applications involving large numbers of samples for testing and a low prevalence of detection.

As used herein the phrase "donor material" refers to biological products, including, for example, blood products, tissues, organs, vaccines, cells, gene therapy, and recombinant therapeutic proteins. Donor material can include more than one donor material. For example, donor material can include more than one blood product and/or other biological product from a single donor. Additionally or alternatively, donor material can include blood products from multiple donors, biological products from multiple donors, or blood products from one donor and other biological products from one or more other donors. As used herein the phrase time to result ("TTR") refers to the time from initiation of a sample for onboard pooling and high-throughput analysis comprising, for example, pooling, sample preparation, amplification, and detection, to the completion of the detection step of the high-throughput analysis.

As used herein, the phrase "clinical use" refers to "in vivo clinical uses" and "in vitro clinical uses." As used herein, "in vivo clinical use" refers to transfusions of whole blood as well as the transfusion of components of whole blood, e.g., packed red blood cells, plasma (e.g., fresh frozen plasma or thawed plasma), platelets, or cryoprecipitate (which is prepared by thawing fresh frozen plasma and collecting the precipitate), collectively referred herein as "blood products." "In vivo clinical use" also encompasses the incorporation of donor blood, or materials derived therefrom, in the production of therapeutics and the donation and/or transplantation of one or more materials, e.g., organs, tissues, etc., from a donor. For example, but not limitation, donor blood can be processed into plasma, either after collection as whole blood or directly as a plasma donation via automated apheresis methods where blood is removed from a donor, the plasma is collected, and the remaining blood is returned to the donor, and that plasma can either be used directly, as fresh frozen plasma or it can be further processed to produce a variety of therapeutic biologics known as plasma-derived products. For example, but not limitation, plasma can be pooled, typically to a significant degree, e.g., pools of 10,000 to 50,000 donations are combined for industrial processing, and the pooled plasma can be fractionated to produce a variety of plasma-derived products including, but not limited to: (1) coagulation factors, e.g., factor VIII, von Willebrand factor, and fibrinogen; (2) protease inhibitors, e.g., alpha1-antitrypsin and C1-esterase inhibitor; (3) albumin; and (4) immunoglobulin G (IgG). As used herein, "in vitro clinical use" refers to the use of biological materials outside of the direct transfusion or transplantation of blood products, plasma-derived products or donor materials into patients, e.g., in research and development of new medical devices, therapeutic processes, or disease diagnostics, as well as in connection with quality assurance/laboratory diagnostics.

4.1. Nucleic Acid Testing

For purpose of example and as embodied herein, systems and methods for onboard pooling and high-throughput analysis can include nucleic acid analysis. For purpose of example and illustration, an exemplary method and automated system for onboard pooling and high-throughput nucleic acid analysis is disclosed herein with reference to FIGS. 2A-2C, 8A, and 8B. As embodied herein, the automated system 1000 can include sample loading area 1100, a sample preparation area, a nucleic acid amplification area and a nucleic acid detection area. As embodied herein, the sample preparation area can include a sample transport 1200. For example and as embodied herein, the sample transport can include a sample preparation carousel 1200. For example and as embodied herein, the nucleic acid amplification area and the nucleic acid detection area can include an amplification and detection subsystem which can include an amplification and detection carousel 1500.

In certain embodiments, the nucleic acid analysis includes a sample preparation process and an amplification process. In certain embodiments, the sample preparation process can include pooling at least first and second samples on the sample transport 1200 as described herein. Additionally or alternatively, sample preparation process can include a lysis process. Additionally or alternatively, the sample preparation process can include a pre-treatment process. As embodied herein, the lysis process, pre-treatment process, and pooling process can each be performed on the sample transport, e.g., sample preparation carousel 1200.

In certain embodiments, the lysing process can include combining the sample with a lysis buffer, microparticles, e.g., CuTi-coated microparticles, and optionally Proteinase K to generate a mixture. In certain embodiments, lysis of the sample does not require a separate Proteinase K treatment step. In certain embodiments, lysing the sample can further include combining the mixture with internal control nucleic acids. In certain embodiments, the exemplary method can further include incubating the mixture to promote binding of nucleic acids within the mixture to the microparticles. CuTi microparticles can bind both RNA and DNA in the sample including target nucleic acids (e.g., pathogenic nucleic acids) and non-target nucleic acids (e.g., host nucleic acids).

Figure 8A:
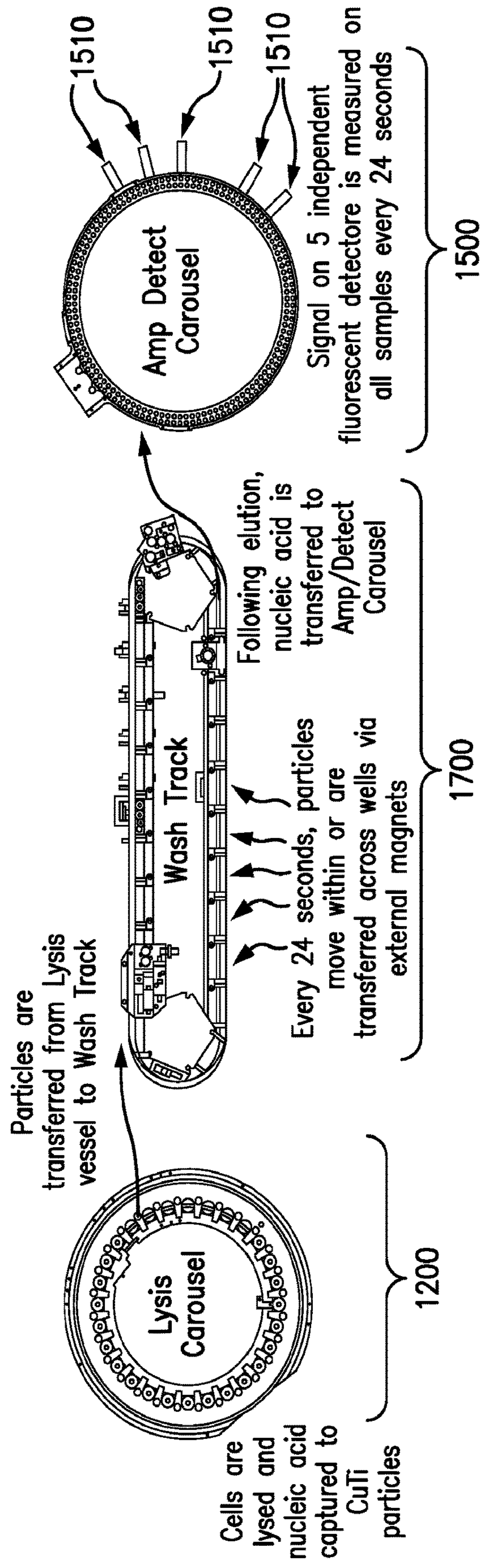
FIGS. 8A and 8B illustrate exemplary process flows for high-throughput nucleic acid analysis on the exemplary system of FIG. 2A.
Figure 8B:
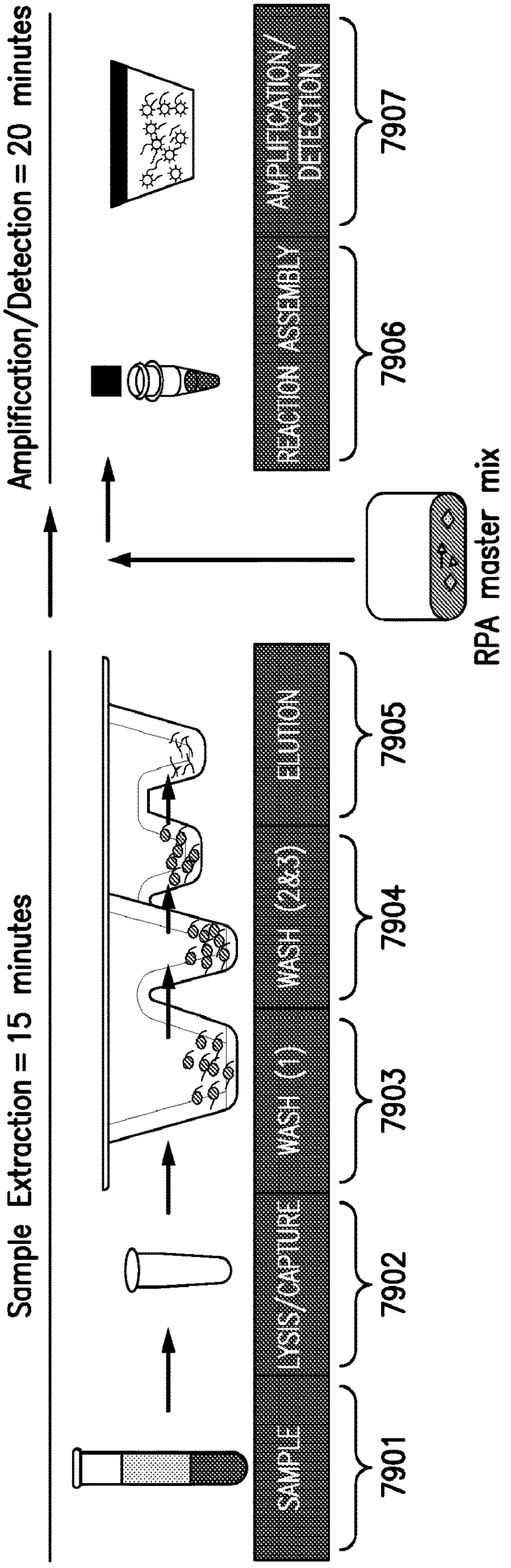

Nucleic acid analysis can further include washing the microparticles bound with nucleic acids with a first wash as shown in 7903 in FIG. 8B. In certain embodiments, the first wash can include lysis buffer. In certain embodiments, the microparticles bound with nucleic acids can be transferred from a vessel on the sample transport 1200 to a different vessel to perform the first wash. For example, but not by way of limitation, the microparticles can be transferred from a vessel in the sample preparation carousel 1200 to a wash vessel of a wash track 1700 using a sample transfer mechanism 1400. For example, but not by way of limitation, a wash vessel can include more than one (1) well, e.g., four (4) wells. As embodied herein, the wash track 1700 or can be configured to perform wash steps of the disclosed method and can further include a plurality of wash vessels. For purpose of illustration not limitation, wash track 1700 can be in a shape of racetrack. In certain embodiments, the exemplary method can subsequently include washing the microparticles bound with nucleic acids with water two times, e.g., a second wash with water and a third wash with water, as shown in 7904 of FIG. 8B. In certain embodiments, the second and third washes are performed in wells different from the first wash, e.g., by applying a magnetic force to capture the microparticles on an inner surface of a first wall of the first well and translating the captured microparticles along the inner surface of the first wall to the second/third well. For purpose of illustration and not limitation, the particles can be moved within or are transferred across wells in about 24 seconds, as shown in FIG. 8A. In certain embodiments, the nucleic acids bound to the microparticles can be eluted (e.g., by using an elution buffer and/or by heat) to generate an eluate in a fourth well of the wash vessel, as depicted in 7905 of FIG. 8B.

In certain embodiments, the exemplary method further includes performing an amplification step and a detection step. In certain embodiments, the amplification step and detection step are performed simultaneously. In certain embodiments, the amplification and detection steps include preparing the eluate for an isothermal amplification reaction to amplify a target nucleic acid of interest in the eluate and simultaneous detection of the amplified target nucleic acid, as shown in 7906 of FIG. 8B. As embodied herein, following elution, the target nucleic acid can be transferred to an amplification and detection subsystem 1500. For purpose of illustration and not limitation, the amplification and detection subsystem 1500 includes a carousel. In certain embodiments, preparing the eluate for amplification and detection includes contacting the eluate with a reagent mixture, referred to as "RPA master mix" in FIG. 8B, and an activator, e.g., magnesium. In certain embodiments, the RPA master mix includes seven (7) enzymes that facilitate primer binding and extension in the amplification reaction, e.g., (i) a recombinase (e.g., UvsX), (ii) a single strand binding protein (e.g., GP32), (iii) a recombinase loading agent (e.g., UvsY), (iv) a DNA polymerase, (v) an exonuclease (e.g., Exonuclease III), (vi) Creatine Kinase and (vii) a reverse transcriptase (e.g., EIAV-RT). In certain embodiments, the reverse transcriptase is not included in the RPA master mix, e.g., if the target nucleic acid is DNA. In certain embodiments, the RPA master mix can further include one or more primers that bind to the target nucleic acid, one or more probes that bind to the amplicon to facilitate signal generation and one or more non-protein components (e.g., for extending the primers (e.g., dNTPs), for use as an energy source (e.g., ATP and phosphocreatine), for stabilizing the proteins and reaction (e.g., reaction buffer (e.g., Tris and salts)) and for use as a crowding agent (e.g., polyethylene glycol)).

In certain embodiments, nucleic acid analysis can include amplifying the target nucleic acid of interest using an isothermal amplification reaction and simultaneously detecting the resulting amplicons, e.g., by fluorescent detection, as depicted in 7907 of FIG. 8B. Non-limiting examples of isothermal amplification reactions can include transcription-mediated amplification (TMA), Recombinase-Polymerase Amplification (RPA) and Nicking Enzyme Amplification Reaction (NEAR). The use of isothermal amplification obviates the need for time consuming temperature transitions. As embodied herein, the amplification and detection subsystem 1500 can include independent fluorescent detectors, e.g., about 5 independent fluorescent detectors 1510, to detect fluorescent signals at a predetermined interval of about every 24 seconds as shown in FIG. 8A, e.g., during the amplification reaction. In certain embodiments, the exemplary method can further include determining a result from the nucleic acid analysis, e.g., determining the presence of a nucleic acid derived from at least one of a plurality of pathogens or infectious agents in the donor blood sample.

In certain embodiments, the exemplary methods and systems of the present disclosure can be used to perform a nucleic acid analysis on a sample. In certain embodiments, the exemplary methods and systems of the present disclosure can be used to screen individual or pooled blood donors (e.g., whole blood, lysed whole blood, serum, or plasma), e.g., to determine whether the donor samples are acceptable for transfusion, and to screen organ and/or tissue donors. In certain embodiments, the exemplary methods and systems of the present disclosure can be used for qualitative detection of nucleic acids derived from a pathogen in a sample of donor blood. In certain embodiments, the exemplary methods and systems of the present disclosure can be used to detect and/or quantify nucleic acids derived from pathogens including but not limited to HIV-1, HIV-2, HCV, HBV, WNV, Zika Virus, Chikungunya Virus, Dengue Virus, *Babesia, Plasmodium* that causes Malaria, Parvo B19 Virus, HAV and/or HEV. In certain embodiments, the exemplary methods and systems of the present disclosure can be used for qualitative detection of nucleic acids derived from HIV-1, HIV-2, HCV, HBV and WNV in serum or plasma samples. In certain embodiments, the exemplary methods and systems of the present disclosure can be used for multiplex analysis of HIV-1, HIV-2, HCV and HBV in serum or plasma samples. In certain embodiments, the exemplary methods and systems of the present disclosure can be used for qualitative detection of nucleic acids derived from *Babesia* in whole blood samples. In certain embodiments, the exemplary methods and systems of the present disclosure can be used for qualitative detection of nucleic acids derived from HAV in plasma samples. In certain embodiments, the exemplary methods and systems of the present disclosure can be used for quantitative detection of nucleic acids derived from Parvovirus in plasma samples.

For example, but not by way of limitation, the methods of the present disclosure can achieve an efficiency of at least about 15 results per hour per $m^3$. In certain embodiments, the methods of the present disclosure can achieve an efficiency of at least about 20 results per hour per $m^3$. In certain embodiments, the methods and systems of the present disclosure can achieve an efficiency of at least about 25 results per hour per $m^3$. In certain embodiments, the methods of the present disclosure can achieve an efficiency of at least about 30 results per hour per $m^3$. In certain embodiments, the methods of the present disclosure can achieve an efficiency of at least about 35 results per hour per $m^3$. In certain embodiments, the methods of the present disclosure can achieve an efficiency of at least about 40 results per hour per $m^3$. In certain embodiments, the methods of the present disclosure can achieve an efficiency of at least about 45 results per hour per $m^3$. In certain embodiments, the methods of the present disclosure can achieve an efficiency of at least about 50 results per hour per $m^3$. In certain embodiments, the methods of the present disclosure can achieve an efficiency of at least about 55 results per hour per $m^3$. In certain embodiments, the methods of the present disclosure can achieve an efficiency of at least about 60 results per hour per $m^3$. In certain embodiments, the methods of the present disclosure can achieve an efficiency of at least about 65 results per hour per $m^3$. In certain embodiments, the methods of the present disclosure can achieve an efficiency of at least about 70 results per hour per $m^3$. In certain embodiments, the methods of the present disclosure can achieve an efficiency of at least about 75 results per hour per $m^3$. In certain embodiments, the methods of the present disclosure can achieve an efficiency of at least about 80 results per hour per $m^3$. In certain embodiments, the methods of the present disclosure can achieve an efficiency of at least about 85 results per $m^3$. In certain embodiments, the methods of the present disclosure can achieve an efficiency of at least about 90 results per hour per $m^3$. In certain embodiments, the methods of the present disclosure can achieve an efficiency of at least about 95 results per hour per $m^3$. In certain embodiments, the methods of the present disclosure can achieve an efficiency of at least about 100 results per hour per $m^3$. In certain embodiments, the methods of the present disclosure can achieve an efficiency of at least about 105 results per hour per $m^3$. In certain embodiments, the methods of the present disclosure can achieve an efficiency of at least about 110 results per hour per $m^3$. In certain embodiments, the methods of the present disclosure can achieve an efficiency of at least about 115 results per hour per $m^3$. In certain embodiments, the methods of the present disclosure can achieve an efficiency of at least about 120 results per hour per $m^3$. In certain embodiments, the methods and systems of the present disclosure can achieve an efficiency of at least about 125 results per hour per $m^3$. In certain embodiments, the methods of the present disclosure can achieve an efficiency of at least about 130 results per hour per $m^3$. In certain embodiments, the methods of the present disclosure can achieve an efficiency of at least about 135 results per hour per $m^3$. In certain embodiments, the methods of the present disclosure can achieve an efficiency of at least about 140 results per hour per $m^3$. In certain embodiments, the methods of the present disclosure can achieve an efficiency of at least about 145 results per hour per $m^3$. In certain embodiments, the methods of the present disclosure can achieve an efficiency of at least about 150 results per hour per $m^3$. In certain embodiments, the methods of the present disclosure can achieve an efficiency of at least about 155 results per hour per $m^3$. In certain embodiments, the methods of the present disclosure can achieve an efficiency of at least about 160 results per hour per $m^3$. In certain embodiments, the methods of the present disclosure can achieve an efficiency of at least about 165 results per hour per $m^3$. In certain embodiments, the methods of the present disclosure can achieve an efficiency of at least about 170 results per hour per $m^3$. In certain embodiments, the methods of the present disclosure can achieve an efficiency of at least about 175 results per hour per $m^3$. In certain embodiments, the methods of the present disclosure can achieve an efficiency of at least about 180 results per hour per $m^3$. In certain embodiments, the methods of the present disclosure can achieve an efficiency of at least about 185 results per hour per $m^3$. In certain embodiments, the methods of the present disclosure can achieve an efficiency of at least about 190 results per hour per $m^3$. In certain embodiments, the methods of the present disclosure can achieve an efficiency of at least about 195 results per hour per $m^3$. In certain embodiments, the methods of the present disclosure can achieve an efficiency of at least about 200 results per hour per $m^3$. In certain embodiments, the methods of the present disclosure can achieve an efficiency of at least about 205 results per hour per $m^3$. In certain embodiments, the methods of the present disclosure can achieve an efficiency of at least about 210 results per hour per $m^3$. In certain embodiments, the methods of the present disclosure can achieve an efficiency of at least about 215 results per hour per $m^3$. In certain embodiments, the methods of the present disclosure can achieve an efficiency of at least about 220 results per hour per $m^3$. In certain embodiments, the methods and systems of the present disclosure can achieve an efficiency of at least about 225 results per hour per $m^3$. In certain embodiments, the methods of the present disclosure can achieve an efficiency of at least about 230 results per hour per $m^3$. In certain embodiments, the methods of the present disclosure can achieve an efficiency of at least about 235 results per hour per $m^3$. In certain embodiments, the methods of the present disclosure can achieve an efficiency of at least about 240 results per hour per $m^3$. In certain embodiments, the methods of the present disclosure can achieve an efficiency of at least about 245 results per hour per $m^3$. In certain embodiments, the methods of the present disclosure can achieve an efficiency of at least about 250 results per hour per $m^3$. In certain embodiments, the methods of the present disclosure can achieve an efficiency of at least about 255 results per hour per $m^3$. In certain embodiments, the methods of the present disclosure can achieve an efficiency of at least about 260 results per hour per $m^3$. In certain embodiments, the methods of the present disclosure can achieve an efficiency of at least about 265 results per hour per $m^3$. In certain embodiments, the methods of the present disclosure can achieve an efficiency of at least about 270 results per hour per $m^3$. In certain embodiments, the methods of the present disclosure can achieve an efficiency of at least about 275 results per hour per $m^3$. In certain embodiments, the methods of the present disclosure can achieve an efficiency of at least about 280 results per hour per $m^3$. In certain embodiments, the methods of the present disclosure can achieve an efficiency of at least about 285 results per hour per $m^3$. In certain embodiments, the methods of the present disclosure can achieve an efficiency of at least about 290 results per hour per $m^3$. In certain embodiments, the methods of the present disclosure can achieve an efficiency of at least about 295 results per hour per $m^3$. In certain embodiments, the methods of the present disclosure can achieve an efficiency of at least about 300 results per hour per $m^3$.

In certain embodiments, the methods of the present disclosure can achieve an efficiency of at least about 30 results per hour per $m^2$. In certain embodiments, the methods of the present disclosure can achieve an efficiency of at least about 35 results per hour per $m^2$. In certain embodiments, the methods of the present disclosure can achieve an efficiency of at least about 40 results per hour per $m^2$. In certain embodiments, the methods of the present disclosure can achieve an efficiency of at least about 45 results per hour per $m^2$. In certain embodiments, the methods of the present disclosure can achieve an efficiency of at least about 50 results per hour per $m^2$. In certain embodiments, the methods of the present disclosure can achieve an efficiency of at least about 55 results per hour per $m^2$. In certain embodiments, the methods of the present disclosure can achieve an efficiency of at least about 60 results per hour per $m^2$. In certain embodiments, the methods of the present disclosure can achieve an efficiency of at least about 65 results per hour per $m^2$. In certain embodiments, the methods of the present disclosure can achieve an efficiency of at least about 70 results per hour per $m^2$. In certain embodiments, the methods of the present disclosure can achieve an efficiency of at least about 75 results per hour per $m^2$. In certain embodiments, the methods of the present disclosure can achieve an efficiency of at least about 80 results per hour per $m^2$. In certain embodiments, the methods of the present disclosure can achieve an efficiency of at least about 85 results per hour per $m^2$. In certain embodiments, the methods of the present disclosure can achieve an efficiency of at least about 90 results per hour per $m^2$. In certain embodiments, the methods of the present disclosure can achieve an efficiency of at least about 95 results per hour per $m^2$. In certain embodiments, the methods of the present disclosure can achieve an efficiency of at least about 100 results per hour per $m^2$. In certain embodiments, the methods of the present disclosure can achieve an efficiency of at least about 105 results per hour per $m^2$. In certain embodiments, the methods of the present disclosure can achieve an efficiency of at least about 110 results per hour per $m^2$. In certain embodiments, the methods of the present disclosure can achieve an efficiency of at least about 115 results per hour per $m^2$. In certain embodiments, the methods of the present disclosure can achieve an efficiency of at least about 120 results per hour per $m^2$. In certain embodiments, the methods of the present disclosure can achieve an efficiency of at least about 125 results per hour per $m^2$. In certain embodiments, the methods of the present disclosure can achieve an efficiency of at least about 130 results per hour per $m^2$. In certain embodiments, the methods of the present disclosure can achieve an efficiency of at least about 135 results per hour per $m^2$. In certain embodiments, the methods of the present disclosure can achieve an efficiency of at least about 140 results per hour per $m^2$. In certain embodiments, the methods of the present disclosure can achieve an efficiency of at least about 145 results per hour per $m^2$. In certain embodiments, the methods of the present disclosure can achieve an efficiency of at least about 150 results per hour per $m^2$. In certain embodiments, the methods of the present disclosure can achieve an efficiency of at least about 155 results per hour per $m^2$. In certain embodiments, the methods of the present disclosure can achieve an efficiency of at least about 160 results per hour per $m^2$. In certain embodiments, the methods of the present disclosure can achieve an efficiency of at least about 165 results per hour per $m^2$. In certain embodiments, the methods of the present disclosure can achieve an efficiency of at least about 170 results per hour per $m^2$. In certain embodiments, the methods of the present disclosure can achieve an efficiency of at least about 175 results per hour per $m^2$. In certain embodiments, the methods of the present disclosure can achieve an efficiency of at least about 180 results per hour per $m^2$. In certain embodiments, the methods of the present disclosure can achieve an efficiency of at least about 185 results per hour per $m^2$. In certain embodiments, the methods of the present disclosure can achieve an efficiency of at least about 190 results per hour per $m^2$. In certain embodiments, the methods of the present disclosure can achieve an efficiency of at least about 195 results per hour per $m^2$. In certain embodiments, the methods of the present disclosure can achieve an efficiency of at least about 200 results per hour per $m^2$. In certain embodiments, the methods of the present disclosure can achieve an efficiency of at least about 205 results per hour per $m^2$. In certain embodiments, the methods of the present disclosure can achieve an efficiency of at least about 210 results per hour per $m^2$. In certain embodiments, the methods of the present disclosure can achieve an efficiency of at least about 215 results per hour per $m^2$. In certain embodiments, the methods of the present disclosure can achieve an efficiency of at least about 220 results per hour per $m^2$. In certain embodiments, the methods of the present disclosure can achieve an efficiency of at least about 225 results per hour per $m^2$. In certain embodiments, the methods of the present disclosure can achieve an efficiency of at least about 230 results per hour per $m^2$. In certain embodiments, the methods of the present disclosure can achieve an efficiency of at least about 235 results per hour per $m^2$. In certain embodiments, the methods of the present disclosure can achieve an efficiency of at least about 240 results per hour per $m^2$. In certain embodiments, the methods of the present disclosure can achieve an efficiency of at least about 245 results per hour per $m^2$. In certain embodiments, the methods of the present disclosure can achieve an efficiency of at least about 250 results per hour per $m^2$. In certain embodiments, the methods of the present disclosure can achieve an efficiency of at least about 255 results per hour per $m^2$. In certain embodiments, the methods of the present disclosure can achieve an efficiency of at least about 260 results per hour per $m^2$. In certain embodiments, the methods of the present disclosure can achieve an efficiency of at least about 265 results per hour per $m^2$. In certain embodiments, the methods of the present disclosure can achieve an efficiency of at least about 270 results per hour per $m^2$. In certain embodiments, the methods of the present disclosure can achieve an efficiency of at least about 275 results per hour per $m^2$. In certain embodiments, the methods of the present disclosure can achieve an efficiency of at least about 280 results per hour per $m^2$. In certain embodiments, the methods of the present disclosure can achieve an efficiency of at least about 285 results per hour per $m^2$. In certain embodiments, the methods of the present disclosure can achieve an efficiency of at least about 290 results per hour per $m^2$. In certain embodiments, the methods of the present disclosure can achieve an efficiency of at least about 295 results per hour per $m^2$. In certain embodiments, the methods of the present disclosure can achieve an efficiency of at least about 300 results per hour per $m^2$.

For example, but not limitation, the systems described herein are capable of transferring a sample from the sample loading area to the sample transport for sample preparation every 24 second lockstep, leading to 150 sample aspirations per hour. In certain embodiments, each sample aspirated will be prepared using the sample preparation carousel and a single target nucleic acid will be amplified and detected, leading to 150 individual results per hour, after the initial start-up period during with the initial sample aspirated is prepared, amplified and detected. In certain embodiments, each aspirated sample will be prepared and split into two amplifications, where each amplification reaction amplifies a single target nucleic acid for detection, leading to 300 individual results per hour, after the initial start-up period during with the initial sample aspirated is prepared, amplified and detected. In certain embodiments, each aspirated sample will be prepared and split into two amplifications, where each amplification reaction amplifies two or more target nucleic acids for detection (e.g., duplex, triplex, or other higher order multiplex amplifications and detections), leading to 600 or more individual results per hour, after the initial start-up period during with the initial sample aspirated is prepared, amplified and detected. In certain embodiments, that initial start-up time will be 20-45 minutes, regardless of whether the elution is split into two amplifications or the amplifications are multiplexed.

For purpose of example and not limitation and as embodied herein, reference is made to FIGS. 9A and 9B, which depict exemplary throughput for certain sample types and processes for an exemplary HTNAT system such as the exemplary system 1000 depicted in FIGS. 2A-2C. FIG. 9A depicts exemplary throughput for serum, plasma, and/or lysed whole blood samples. For purpose of example and as embodied herein, high-throughput analysis of serum, plasma, and/or lysed whole blood samples can include a lysis process, a wash and elution process, and an amplification and detection process as described herein. For purpose of example and as embodied herein, a throughput of about 150 samples per hour can be achieved when processing individual samples. As embodied herein, with a throughput of about 150 samples per hour, HTNAT systems as embodied herein can achieve 150 individual results per hour and up to 600 or more individual results per hour depending on, for example, whether a split eluate configuration and/or multiplex amplification and detection strategies are used.

With reference to FIG. 9A, onboard pooling in accordance with the disclosed subject matter can increase throughput. For purpose of example and as embodied herein, onboard pooling of two samples can include transferring two samples from the sample loading area to the sample transport for sample preparation every 24 second lockstep, leading to 300 sample aspirations per hour. For purpose of example and as embodied herein, onboard pooling in accordance with the disclosed subject matter can double the number of sample aspirations per hour. As embodied herein, the samples can be serum, plasma, and/or lysed whole blood samples, and high-throughput analysis can include an onboard pooling process, a lysis process, a wash and elution process, and an amplification and detection process as described herein. With reference to FIG. 9A, when processing pools of two serum, plasma, and/or lysed whole blood samples, throughput can be about 150 pools/hr. As embodied herein, with a throughput of about 150 pools per hour, HTNAT systems as embodied herein can achieve 150 pool results per hour and up to 600 or more pool results per hour depending on, for example, whether a split eluate configuration and/or multiplex amplification and detection strategies are used. As embodied herein, each pool result, i.e., each result for a pooled sample, can facilitate a determination of the absence of one or more target nucleic acids in two or more individual samples. For example, if a pool result includes a determination of the absence of a target nucleic acid in the pool, the pool result can include a determination of the absence of target nucleic acid in two individual samples, i.e., using a pool size of 2. For example, using a pool size of 12 each pool result can include a determination of the absence of target nucleic acid in 12 individual samples. As embodied herein, onboard pooling in accordance with the disclosed subject matter can facilitate determinations of the absence of target nucleic acids for more individual samples per hour as compared to high-throughput analysis of individual samples without pooling.

FIG. 9B depicts exemplary throughput for whole blood samples including a pre-treatment process as described herein. For purpose of example and as embodied herein, high-throughput analysis of whole blood samples can include a pre-treatment process, a lysis process, a wash and elution process, and an amplification and detection process as described herein. For purpose of example and as embodied herein, a throughput of about 75 samples per hour can be achieved when processing individual samples. As embodied herein, processing individual whole blood samples can include transferring one samples from the sample loading area to the sample transport for sample preparation every other 24 second lockstep, leading to about 75 sample aspirations per hour. As embodied herein, with a throughput of about 75 samples per hour, HTNAT systems as embodied herein can achieve 75 individual results per hour and up to 300 or more individual results per hour depending on, for example, whether a split eluate configuration and/or multiplex amplification and detection strategies are used.

For purpose of example and without limitation, in accordance with an aspect of the disclosed subject matter between about 240 and about 340 samples can be transferred from the sample loading area to the sample transport per hour.

With reference to FIG. 9B, onboard pooling in accordance with the disclosed subject matter can increase throughput when processing whole blood samples. For purpose of example and as embodied herein, onboard pooling of six whole blood samples can include transferring one sample from the sample loading area to the sample transport for five out of every six 24 second lock steps, leading to about 125 sample aspirations per hour. As embodied herein, high-throughput analysis of the whole blood samples can include a pre-treatment process, an onboard pooling process, a lysis process, a wash and elution process, and an amplification and detection process as described herein. With reference to FIG. 9B, when processing pools of six whole blood samples, throughput can be about 21 pools/hr. As embodied herein, with a throughput of about 21 pools per hour, HTNAT systems as embodied herein can achieve 21 pool results per hour and up to about 84 or more pool results per hour depending on, for example, whether a split eluate configuration and/or multiplex amplification and detection strategies are used. As embodied herein, using a pool of 6 each pool result can facilitate a determination of the absence of one or more target nucleic acids in two or more individual samples. For example, if a pool result includes a determination of the absence of a target nucleic acid in the pool, the pool result can include a determination of the absence of target nucleic acid in 6 individual samples, i.e., using a pool size of 6.

In accordance with another aspect of the disclosed subject matter, systems of the present disclosure can achieve certain performance criteria relating to sample throughput (as defined as the number of nucleic acid analysis results per hour) per unit of area or volume occupied by the system, e.g., the "efficiency" of the system. For example, but not limitation, the systems embodied herein, e.g., in FIGS. 3, 5-8, 15-16, 43, and 45-66, can have a footprint of about 1 $m^2$ to about 3 $m^2$, or about 1 $m^2$ to about 2.5 $m^2$, or about 1 $m^2$ to about 2 $m^2$, 1 $m^2$ to about 1.5 $m^2$ or even about 1 $m^2$ to about 1.2 $m^2$. As embodied herein, such systems will generally have a height of less than 6 feet (about 2 m), and, in certain embodiments, will be configured to have a height not more than that associated with 90% of the population intended to operate the system. In certain embodiments, the systems of the present disclosure can be configured to have a height not more than that associated with 90% of the female population intended to operate the system. Thus, in certain embodiments, the systems embodied herein, e.g., in FIGS. 3, 5-8, 15-16, 43, and 45-66, can have a volume of about 1 $m^3$ to about 3 $m^3$, or about 1 $m^3$ to about 3.5 $m^3$, or about 1 $m^3$ to about 3 $m^3$, or about 1 $m^3$ to about 2.5 $m^3$, or even about 1 $m^3$ to about 2 $m^3$ based on a height of about 1 m to about 2 m.

4.1.1. Sample Preparation Systems

For purpose of example and as embodied herein, the sample transport 1200 can be a sample preparation carousel. As embodied herein, sample preparation processes, including for example, a lysis process, pooling process, and/or pre-treatment process can be performed on the sample transport 1200. As embodied herein, sample preparation can be used to isolate and/or purify nucleic acid present in the sample and can include the steps of sample lysis, nucleic acid capture, nucleic acid wash and nucleic acid elution.

4.1.1.1. Sample Lysis and Nucleic Acid Capture Systems

As described above, sample lysis disrupts the membranes or walls of pathogens, infectious agents, and/or cells present within a sample to release the nucleic acids present within the pathogens, infectious agents, and/or cells present in the sample. Generally, systems are employed to automatically contact a lysis solution with a donor sample and/or a pooled sample to be analyzed.

As embodied herein, the sample preparation carousel 1200 comprises 28 positions (clockwise around the central carousel) capable of holding vessels 1220. For example and as embodied herein, the vessels 1220 can be lysis tubes. In the example system of FIGS. 2A-2C, the carousel 1200 operates on a lock step principle where the carousel moves one position in a clockwise direction after each lockstep. The lockstep, or the time between movements of the carousel, is 24 seconds in this embodiment. Not all positions on the carousel 1200 are used in the sample lysing process in that some position are used to load the lysis tube onto the carousel, dispense lysis buffer or remove the lysis tube. The below table, Table 2, depicts exemplary times and operations with regarding the lysis process. As shown in this exemplary embodiment using a lockstep of 24 seconds, the sample processing time for the lysis process is 384 seconds, or 6.4 minutes.

TABLE 2

| Pos. | Function | Sample Process Time (Seconds) |
|---|---|---|
| L1 | Load Lysis Tube in Carousel | |
| | Load Transfer Tip in Carousel | |
| L2 | Dispense 60 °C Lysis Buffer | |
| | (100-1500 μl +/−5%) | |
| L3 | Aspirate uParticlesSip | |
| | (30 μl +/−5%) | |
| | Aspirate Internal ControlSip | |
| | (50 μl +/−5%) | |
| | Aspirate Proteinase K (only HxV) | |
| | Dispense into LysisTube | |
| | Wash Probe | |
| L4 | Aspirate & Dispense Sample | 24 |
| | Wash Probe | |
| | (100-1000 μl +/−5%) | |
| L5-17 | Incubation (312 sec) (60 °C) | 312 |
| | Mixing | |
| | Indexing | |
| L18 | Pre-collect μParticles | 24 |
| L19 | Pickup Transfer Tip | 24 |
| | Capture μParticles | |
| | Transfer μParticles | |
| L20 | Aspirate Lysis contents | |
| L21 | Transfer Lysis Tube to Waste | |

Figure 3:
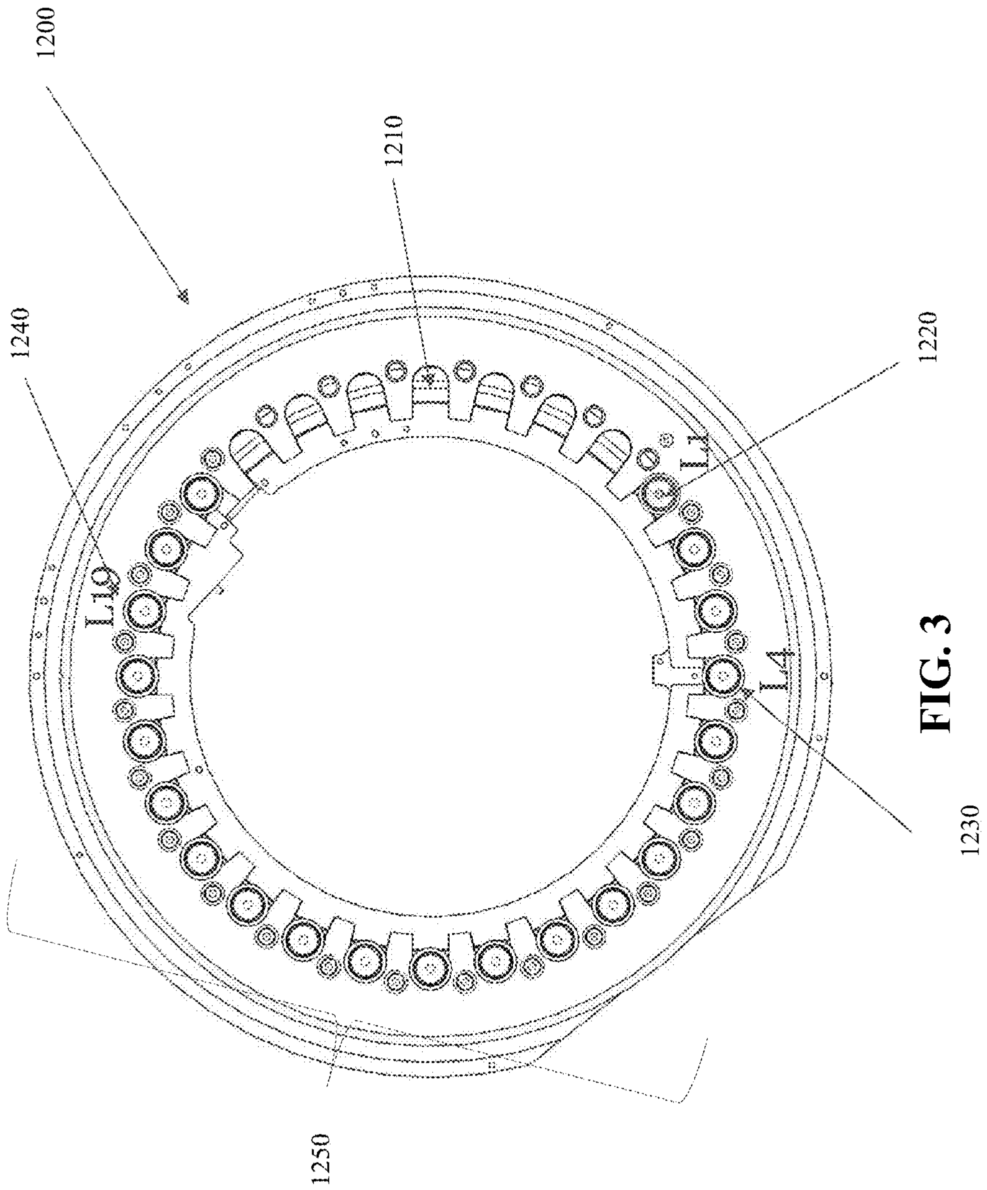
FIG. 3 is a top view of a sample transport from the exemplary system of FIG. 2A.

In the exemplary embodiment illustrated in FIG. 3, position L1 corresponds to the loading of a lysis tube 1220 into the process queue. In certain embodiments, loading is accomplished by known "Pick & Place" strategies from a loadable stack. L2 corresponds to a lysis buffer dispensing position. L3 corresponds to dispensing microparticles in the lysis tube. Reagents dispensed at this position can be dispensed via known "Sip & Spit" strategies from reagent containers. Reagents dispensed at this position include, but are not limited to: internal controls, e.g., dispensed at a volume of 50 μl (+/−5%) although other volumes are contemplated within the scope of the instant disclosure, microparticles, e.g., dispensed at a volume of 30 μl (+/−5%) or 60 μl (+/−5%) although other volumes are contemplated within the scope of the instant disclosure, Proteinase K, e.g., dispensed at a volume of about 20 μl to about 100 μl, at a volume of about 40 μl (+/−5%) or at a volume of about 20 μl (+/−5%) although other volumes are contemplated within the scope of the instant disclosure.

Exemplary position L4 corresponds to a sample dispensing position. Sample dispensed at this position can be dispensed via known "Sip & Spit" strategies from sample tubes. Samples dispensed at this position can be dispensed at a volume of 100-1000 μl (+/−5%) although other volumes are contemplated within the scope of the instant disclosure. Samples can be transferred to the sample dispensing position 1230 (L4) of the sample transport 1200 from the sample loading area 1100. Additionally or alternatively, samples can be transferred the sample dispensing position 1230 (L4) of the sample transport 1200 from intermediate positions on the sample transport 1200, as described further herein. Additionally or alternatively, and as embodied herein, samples can be pooled in a vessel at the sample dispensing position 1230 (L4) of the sample transport 1200.

Exemplary positions L5-L17 correspond to incubation, mixing, and indexing positions. For example, incubation, mixing, and indexing at positions L6-L18 can incorporate the use of resistive heaters, carousel movement, pop-up mixers, lock step transfers, and/or time priority scheduling. In certain embodiments positions L5-L17 can incorporate incubation in one or more sample lysis buffer.

In certain embodiments, the sample lysis buffers used in the methods and systems described herein comprise about 2.5 to about 4.7 M GITC, about 2% to about 10% Tween-20, and a pH of about 5.5 to about 8.0. In certain embodiments, e.g., embodiments relating to plasma or serum samples, the sample lysis buffer comprises about 4.7 M GITC, about 10% Tween-20, and a pH of about 7.8. In certain embodiments, e.g., embodiments relating to whole blood samples, the sample lysis buffer comprises about 3.5 M GITC, about 2.5% Tween-20, and a pH of about 6.0. In certain embodiments, L2-L16 will employ a heater, e.g., a resistive heater, to heat the lysis sample to about 50° C. to about 60° C. In certain embodiments, mixing of the samples is achieved via offline orbital mixing at about 1500 rpm.

Exemplary position L18 corresponds to a microparticle capture wherein a magnet captures the microparticles at the bottom of a lysis tube 120 to collect the microparticles. This serves to collect the microparticles together before transferring to the wash and elute system 1500. As embodied herein, L19 corresponds to a capture and a transfer position 1240. In this position, at least a fractionated portion of the sample (e.g., a pooled sample) can be captured and transferred for high-throughput analysis. For example and as embodied herein, the fractionated portion of the sample can include microparticles, which can be released from the bottom of the lysis tube 1220 and captured by the sample transfer mechanism 1400. For example and as embodied herein, the sample transfer mechanism 1400 can include a transfer tip and the microparticles can be captured via magnetic capture against structural elements of the transfer tip. In certain embodiments, such structural elements can include but are not limited to fins, e.g., for magnetic capture of microparticles between such fins. In certain embodiments, microparticles are transferred from the transfer tip to a subsequent process container (e.g., a well within the wash and elute subsystem) by positioning the transfer tip containing with the trapped microparticles into or over the container, retracting the capture magnet and shaking or vibrating the tip.

4.1.1.2. Mixing Systems

As described above, sample preparation processes for use herein can include, for example, a pre-treatment process, lysis, process, an onboard pooling process, and combinations thereof. For example and as embodied herein, sample preparation processes can be carried out in a sample preparation area, and the sample preparation area can include a sample transport. Sample preparation processes for use herein, can include mixing. For example and not limitation, a lysis process can include mixing to mix a sample and reagents in a lysis tube. Additionally or alternatively, an onboard pooling process can include mixing two or more samples in a vessel, such as for example to distribute the two or more samples more evenly within the pooled sample.

As described above, mixing of the contents of the vessels on the sample transport 1200 can occur at one or more positions on the sample transport 1200. Mixing of the contents of vessels on the sample transport 1200 can be desired, for example, to mix two or more samples in a pooled sample. Mixing can be performed, for example, using mechanical agitation, such as with a mechanical tip, which can be inserted within the vessel. Additionally or alternatively, mixing can be performed using a mechanism, such as a vortexer, which can interface with the vessel to, for example, vibrate and/or rotate the vessel to mix its contents. Additionally or alternatively, mixing can be performed using magnets, which can interact with, for example, magnetic particles within the vessel to agitate the contents of the vessel. For example, permanent magnets can be moved relative to the lysis vessel and can agitate magnetic particles within the vessel. Additionally or alternatively, electromagnets can be positioned adjacent to the vessel and used to agitate magnetic particles within the vessel.

Additionally or alternatively, and as embodied herein, mixing can be performed using successive oscillation of the sample transport. For example and as embodied herein, the sample transport can be configured to transport one or more samples in a vessel along a transport path from a sample dispense position to a sample capture and transfer position, as described further herein. For example and not limitation, the sample transport can include a serpentine path, conveyor, such as a chain conveyor, extrusion, robotic handler, belt, or vehicle system. As embodied herein, the sample transport include a sample preparation carousel, such as a lysis carousel. Successive oscillation of the sample transport can be performed with the vessel to be mixed moving in an arc with each oscillation of the sample transport. Movement in an arc can include at least two axis of movement. For example and as embodied herein, movement in an arc can include successive clockwise and counterclockwise rotation of a carousel. For example and not limitation, mixing of the contents of the vessels on the sample transport 1200 can be performed using rotational movement of sample transport 1200. For example, sample transport 1200 can be rotated clockwise and counterclockwise in quick succession and the rotation of the sample transport 1200 can cause the contents of vessels on the sample transport 1200 to mix. Additionally or alternatively, movement in an arc can include successive movement in one direction followed by movement in another direction, such as for example, successive movement of a belt in a first direction followed by movement in a second direction along a portion of the belt defining an arc, e.g., along a portion comprising movement in at least two axis.

Figure 10A:
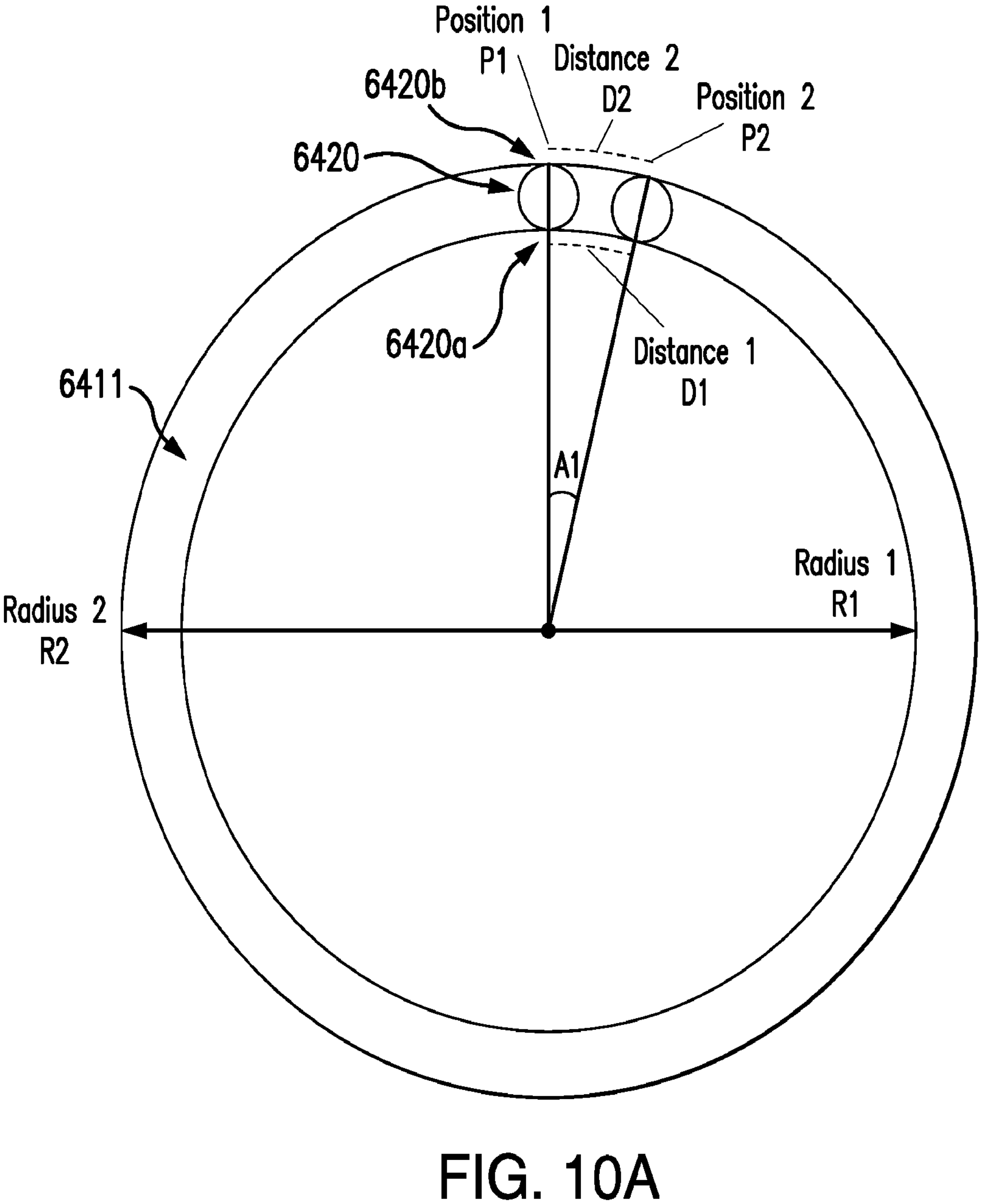
FIG. 10A depicts an exemplary schematic of a sample transport and exemplary rotational movement of the sample transport for performing sample mixing.

Without wishing to be bound by theory, exemplary physics principles of mixing which can be performed using successive oscillations, e.g., successive rotational movement of sample transport 1200 are explained with reference to FIG. 10A. For purpose of illustration and explanation and not limitation, sample transport 1200 is depicted with a single vessel 6420, which can be moved from position P1 to position P2 by rotation of sample transport 1200. As shown, a first radius, R1, can be measured between a center of the sample transport 1200 and a portion of the wall 6420*a* of vessel 6420 closest to the center of the sample transport 1200, and a second radius, R2, can be measured between a center of the sample transport 1200 and a portion of the wall 6420*b* of vessel 6420 farthest from the center of the sample transport 1200. As embodied herein R2 can be greater than R2. The sample transport 1200 can rotate vessel 6420 from position P1 to position P2. As shown, inner wall portion 6420*a* travels a distance D1 during rotation of the vessel from position P1 to position P2 and outer wall portion 6420*b* travels a distance D2 during rotation of the vessel from position P1 to position P2. As embodied herein, during rotation of sample transport 1200 and movement of vessel 6420 from position P1 to position P2, the inner wall portion 6420*a* can travel distance D1 in the same amount of time it takes outer wall portion 6420*b* to travel D2. Accordingly, and as embodied herein, acceleration of outer wall portion 6420*b* during rotation of the sample transport 1200 and movement of vessel 6420 from position P1 to position P2 is greater than the acceleration of the inner wall portion 6420*a* during rotation of the sample transport 1200 and movement of vessel 6420 from position P1 to position P2. In other words, as embodied herein, during rotation of sample transport 1200, the distance traveled on the outside of the carousel is greater than the distance traveled on the inside of the carousel, and since both distances are traveled simultaneously, the acceleration is greater on the outside of the carousel than on the inside of the carousel.

For purpose of example and explanation and not limitation, exemplary calculations are included herein to further illustrate and explain the operation of the exemplary embodiment. For example, the distance traveled on the inside of the carousel during rotation of the carousel from position P1 to position P2 can be represented as an arc having an arc length D1 and the distance traveled on the outside of the carousel can be represented as an arc having an arc length D2. For purpose of explanation and illustration, and as embodied herein, sample transport 1200 can have an inner radius R1 of approximately 117 mm and an outer radius R2 of approximately 133 mm, and position P1 and position P2 can be approximately 1.33 degrees of rotation apart. For purpose of explanation and illustration the arc length D1 can be calculated as 2*R1*π*1.33/360. D2 can be calculated as 2*R2*π*1.33/360. For purpose of explanation and illustration, and as embodied herein, D1 can be approximately 2.72 mm and D2 can be approximately 3.08 mm.

As described above, during rotational movement of the sample transport 1200 from position P1 to position P2, inner wall portion 6420*a* travels distance D1 in the same amount of time outer wall portion 6420*b* travels distance D2. For purpose of explanation and illustration and not limitation, the acceleration of the inner wall portion 6420*a* during rotation from position P1 to position P2 over time "t" can be calculated as acceleration $1=2*D1/t^2$ and the acceleration of outer wall portion 6420*b* can be calculated as acceleration $2=2*D2/t^2$. For purpose of example, and as embodied herein, for a D1 of 2.72 mm and a D2 of 3.08 mm, acceleration 1 of the inner wall portion 6420*a* can be approximately 88% of acceleration 2 of the outer wall portion 6420*b*.

As described above and as embodied herein, acceleration of outer wall portion 6420*b* during rotation of the sample transport 1200 and movement of vessel 6420 from position P1 to position P2 can be greater than the acceleration of the inner wall portion 6420*a* during rotation of the sample transport 1200 and movement of vessel 6420 from position P1 to position P2. As embodied herein, greater acceleration of the outer wall portion 6420*b* can be related to the diameter of the vessel. For example, and with reference to FIG. 10A, the difference between R2 and R1 can be related to the vessel, e.g., lysis tube, diameter, with vessels having larger diameters corresponding to a larger difference between R2 and R1 and a larger difference in acceleration between the outer wall portion 6420*b* and the inner wall portion 6420*a*. For example and not limitation, vessels, e.g., lysis tubes having a lower draft angle at the bottom of the tube can have a larger diameter at the bottom of the lysis tube, which can provide a corresponding larger difference in acceleration between the outer wall portion 6420*b* and the inner wall portion 6420*a*. For purpose of example and not limitation, a lysis tube with a 1° draft angle will have a larger tube diameter towards the bottom of the tube than a lysis tube with a 2.5° draft angle. Further, and as described further herein, a larger lysis tube diameter can result in a lower fluid height within the lysis tube, which can, for example, reduce the risk of liquid splashing out of the lysis tube during mixing.

Figure 10B:
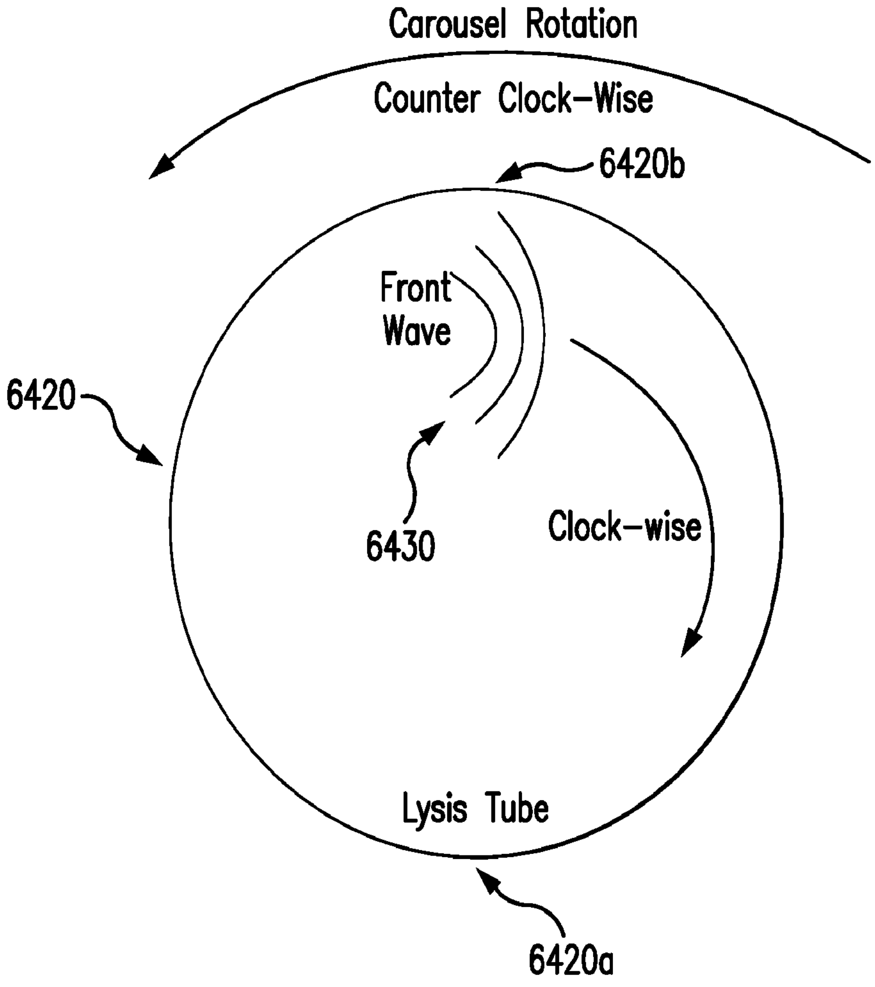
FIGS. 10B and 10C depict an exemplary schematic of a vessel during successive oscillations of the sample transport depicted in FIG. 9A.

FIG. 10B depicts a schematic view of a vessel 6420 during counter-clockwise rotation of sample transport 1200 from a first position to a second position. As described above, during rotation of sample transport 1200 from a first position to a second position, outer wall portion 6420*b* can accelerate faster than inner wall portion 6420*a*. This difference of accelerations between inner wall portion 6420*a* and outer wall portion 6420*b* can cause liquid contained in vessel 6420, such as, for example, a sample and lysis buffer, to rotate and create a wave in the vessel during movement of the sample transport 1200 from a first position to a second position. For purpose of example and not limitation, FIG. 10B depicts a liquid wave front 6430 forming in vessel 6420 along outer wall portion 6420*b* during counter-clockwise rotation of sample transport 1200. As shown, the wave front 6430 can travel along the outer wall of the vessel in a direction opposite to the rotational movement of the sample transport 1200. For example, as depicted in FIG. 10B, a counter-clockwise rotation of the sample transport 1200 can cause wave front 6430 to form and travel in a clockwise direction along the outer wall portion 6420*b* of the vessel.

Figure 10C:
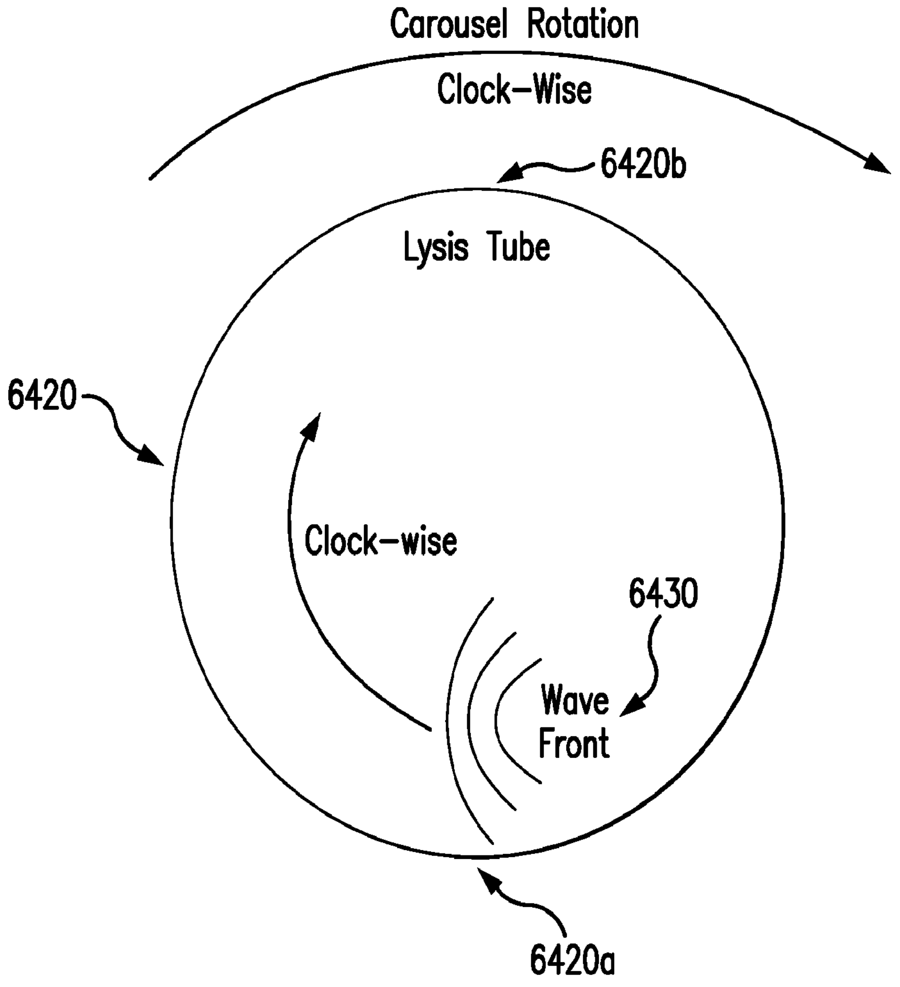

As further embodied herein, for purpose of example and not limitation, reversing the direction of rotation of sample transport 1200 can further contribute to mixing of the contents of the vessels on the sample transport 1200. For example, and with reference to FIG. 10C, vessel 6420 is shown during clockwise rotation of sample transport 1200 from position P2 to position P3. As shown for purpose of illustration and discussion, after counter-clockwise rotation of sample transport 1200 and vessel 6420 from position P1 to position P2, wave front 6430 can travel within the vessel along the outer wall from the outer wall portion 6420*b* to inner wall portion 6420*a*. As embodied herein, reversing the rotational direction of the sample transport 1200 (e.g., from counter-clockwise rotation to clockwise rotation) when the wave front has traveled from the outer wall portion 6420*b* to inner wall portion 6420*a* can impart further rotational forces on the contents of the vessel, e.g., lysis tube. For example, and as embodied herein, reversing the direction of the carousel with the wave front 6430 along the inner wall portion 6420*a* can cause the wave front to continue its clock-wise rotation. For purpose of example and as embodied herein, vessel 6420 can include liquid, such as for example a whole blood sample and lysis fluid, and magnetic particles as described herein. As embodied herein, rotating the carousel successively in one direction and then the opposite direction (e.g., counter-clockwise followed by clockwise rotation, or vice versa) can form a vortex of magnetic particles within the liquid of the vessel. The rotation speed, rotation distance, reversal, and delay timing can be selected based on the desired performance of the system and dimensions of the system, such as, for example, the dimensions of the vessel and dimensions of the sample transport 1200. For purpose of example, and as embodied herein, the rotation speed, rotation distance, reversal, and delay timing can be selected to form a vortex within liquid contents of the vessel, e.g., lysis tube, within approximately 1.3 seconds. As embodied herein, the formation of a vortex within liquid contents of the vessel can provide an indication of mixing.

Mixing the contents of vessels on the sample transport 1200 using successive oscillation of the sample transport, such as for example, rotational movement of sample transport 1200 can provide advantages. For example and not limitation, mixing using rotational movement of sample transport 1200 can reduce or eliminate the hardware required to mix the contents of vessels on the sample transport 1200. For example, and as embodied herein, when rotational movement of the carousel is used for mixing, separate mixing hardware, such as magnets and/or a mechanical agitator or vortexer are no longer required. Additionally or alternatively, mixing using rotational movement of sample transport 1200 can reduce the number of consumables used. For example, mixing using rotational movement of sample transport 1200 can reduce or eliminate the need for a disposable mechanical agitator tip. Additionally or alternatively, mixing using rotational movement of sample transport 1200 can reduce or eliminate the need for a splash or aerosol containment covering for the vessel, e.g., lysis tube, which can further reduce consumable use. Additionally or alternatively, and as further embodied herein, mixing using rotational movement of sample transport 1200 can reduce the time required for mixing and can increase system throughput. For example and not limitation, mixing using rotational movement of sample transport 1200 can reduce or eliminate other mixing steps, such as mechanical agitation, which can require additional processing time. Additionally or alternatively, mixing using successive oscillation of the sample transport, such as for example, rotational movement of sample transport 1200 can be performed using small successive oscillations, such as for example, clockwise and counterclockwise rotation of the rotatable carousel for short distances, such as for example, rotation corresponding to approximately +/−10% of vessel diameter. As embodied herein, a robotic pipettor can access vessels on the rotatable carousel during the mixing operation, which can be advantageous for reducing sample processing times. Additionally or alternatively, and as embodied herein, mixing the contents of the vessel using successive oscillations of sample transport 1200 can be performed at any of the positions on the carousel.

4.1.1.3. Nucleic Acid Wash & Elute Systems

Figure 11A:
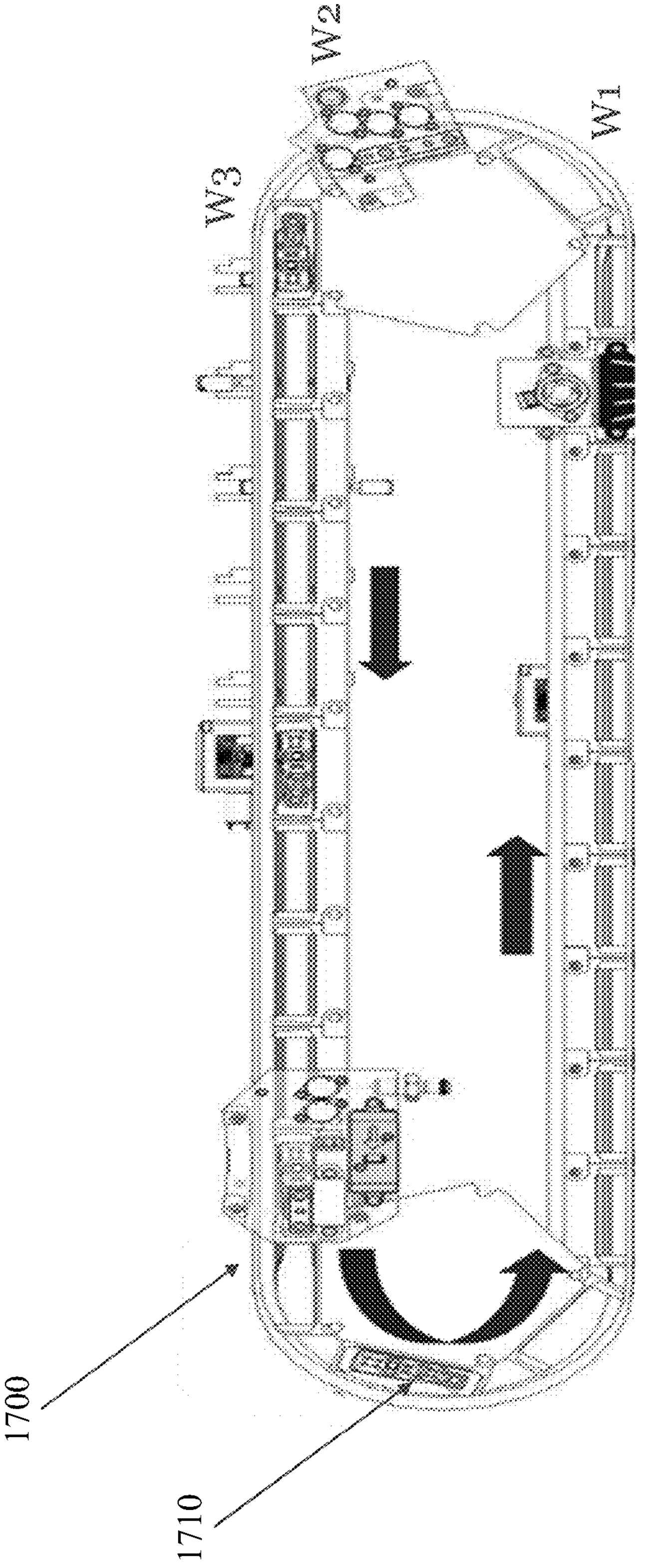
FIG. 11A is a schematic top view of the wash and eluate system from the exemplary system of FIG. 2A.
Figure 11B:
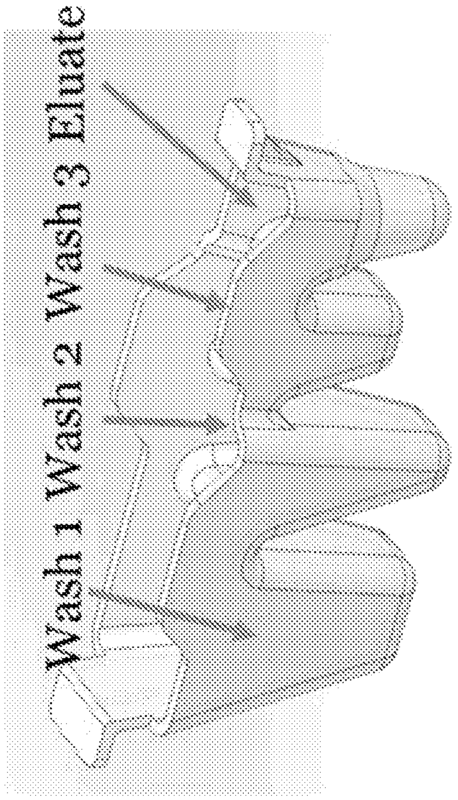
FIG. 11B is a front isometric view of an exemplary wash vessel.

For example and as embodied herein, the wash and elute system can wash the sample to eliminate undesired material from the microparticles and then elute the captured material, e.g., nucleic acids, from the microparticles. In certain embodiments, as shown in FIG. 11A, the wash and elute system 1700 can include a rotatable racetrack-shaped carousel having positions to hold wash vessels 1710. The wash vessels 1710 can hold wash buffer and elution buffer during the wash and elution process. As embodied herein, the wash vessels can each define a plurality of wells, e.g., Wash 1, Wash 2, Wash 3, and Eluate as shown in the exemplary embodiment depicted in FIG. 11B, for the wash and elute process.

As embodied herein, the wash and elute system 1700 can include 24 positions (clockwise around the central carousel), which are identified as wash 1 ("W1") through wash 24 ("W24"). Embodiments of the present disclosure can comprise greater or fewer than 24 positions, depending on alternative system configurations or the desired capacity or throughput of the system, and the individual positions need not be arranged as illustrated, but rather can be arranged in carousel, linear, or essentially any other orientation compatible with the throughput requirements of the instant disclosure. Not all positions on the wash and elute system 1700 are used in the sample washing and elution process in that, for example, some position are used to load the wash vessels onto the carousel, dispense wash buffer or remove the wash vessel.

The below table, Table 3, depicts exemplary times and operations regarding the wash and elution process. As shown in this exemplary embodiment using a lockstep of 24 seconds, the sample processing time for the wash and elute process is 480 seconds, or 8 minutes.

TABLE 3

| Pos. | Function | Sample Process Time (Seconds) |
|---|---|---|
| W1 | Load Wash Vessel in Carousel | |
| W2 | Dispense Wash 1 (Lysis)<br>(500 µl +/−5%)<br>Dispense Wash 2 (Water)<br>(250 µl +/−5%)<br>Dispense Wash 3 (Water)<br>(125 µl +/−5%) | |
| W3 | Pickup Transfer Tip<br>Capture uParticles<br>Transfer uParticles | |
| W4-W7 | Incubation and Mixing (Wash 1) | |
| W8 | Transfer uParticles to Wash 2 | |
| W9 | Mixing (Wash 2)<br>Preheat Elution Well | |
| W10 | Transfer uParticles to Wash 3<br>Preheat Elution Well | |
| W11 | Mixing (Wash 3)<br>Preheat Elution Well<br>Dispense Elution Buffer | |
| W12 | Transfer uParticles to Elution Well<br>Incubate Elution Well | |
| W13-W20 | Incubation and Mix Elution | |
| W21 | Transfer uParticles to Wash 3<br>Cool Elution Well | |
| W22 | Aspirate Eluent<br>Dispense Eluent to Amp Vessel 1<br>Dispense Eluent to Amp Vessel 2 | |
| W23 | Aspirate wash contents to waste | |
| W24 | Transfer Wash Vessel to waste | |

In the exemplary embodiment illustrated in FIG. 11A, W1 corresponds to a transfer position where the wash vessel is transferred to the carousel from, e.g., a commodity loading area. Transfer of wash vessels to this position can be accomplished via known methods in the art, e.g., sideways shuffle strategies and/or "Pick & Place" strategies.

As embodied herein, exemplary position W2 corresponds to a dispensing position to dispense wash solution into wells Wash 1-Wash 3. Dispensing of wash solution can be accomplished, e.g., via direct plumb from a bulk reservoir. In certain embodiments, the wash solution of well Wash 1 is dispensed at a volume of 500 µl (+/−5%) although other volumes are contemplated within the instant disclosure. In certain embodiments, the wash solution of well P1 comprises about 2.5 M to about 4.7 M GITC, about 2% to about 10% Tween-20, and a pH of about 5.5 to about 8.0. In certain embodiments, e.g., with respect to plasma and serum samples, the wash solution of well Wash 1 can include about 4.7 M GITC, about 10% Tween-20, and a pH of about 7.8. In certain embodiments, e.g., with respect to whole blood samples, the wash solution of well Wash 1 can comprise about 3.5 M GITC, about 2.5% Tween-20, and a pH of about 6.0. As embodied herein, was solution can also be dispensed in the wells Wash 2 and Wash 3 at position W2. As embodied herein, the wash solution dispensed into wells Wash 2 and Wash 3 at position W2 can be water.

Exemplary position W3 corresponds to a microparticle transfer position. As embodied herein, the sample transfer mechanism 1400 can transfer at least a fractionated portion of the pooled sample from the sample transport 1200 to the wash and elute system 1700. For purpose of example and not limitation, transfer can be accomplished via retraction of the capture magnet and shaking of the tip to deposit the microparticles into well P1 in W3.

Exemplary positions W4-W7 correspond to incubation and mixing positions. Incubation and mixing at positions W4-W7 can incorporate the use of resistive heaters, mixing via top and/or bottom magnets, e.g., moving permanent magnets, as well as carousel movement, pop-up mixers, and/or electro-magnets. In certain embodiments, positions W4-W7 can employ a heater, e.g., a resistive heater, to heat the lysis sample to about 37° C. In certain embodiments, W4-W7 employ incubation in Wash 1 for about 96 seconds (4 lock steps at 24 seconds each). In certain embodiments, position W8 involves transfer of the microparticles into well Wash 2 for Wash 2 and mixing. In certain embodiments, Wash 2 is water. In certain embodiments the transfer can be accomplished using moveable magnets above the wells to slide the microparticles across the internal surface of the well to collect, transfer and release the microparticles. In some embodiments, transfer can be accomplished using moveable magnets below the wells to slide the microparticles within internal channels at the bottom of wells to collect, transfer and release the microparticles. In certain embodiments stationary electro-magnets, e.g., selectively turning on/off adjacent magnets to achieve magnetic particle movement can be employed. Other methods of transferring microparticles such as in inverse particle processing can also be used. In certain embodiments, position W9 comprises mixing in the wash solution at well Wash 2 for about 24 seconds. In certain embodiments, mixing is accomplished via carousel movement, a pop-up mixer, and/or electro-magnets.

Exemplary position W10 involves transfer of the microparticles into the wash solution at well Wash 3 and mixing. In certain embodiments the wash solution at well Wash 3 is water. In certain embodiments the transfer can be accomplished using moveable magnets above the wells to slide the microparticles across the internal surface of the seal to collect, transfer and release the microparticles. In certain embodiments, position W11 comprises mixing in the wash solution in well Wash 3 for about 24 seconds. In certain embodiments, mixing is accomplished via carousel movement, a pop-up mixer, and/or electro-magnets. In certain embodiments, mixing is accomplished using an offline orbital mixer at 1500 rpm.

In certain embodiments, positions W12-W20 correspond to transfer and incubation positions where the sample is incubated within the elution buffer to remove the target from the microparticles. For example, but not limitation, W12 is a transfer position where the microparticles are transferred, e.g., via movable permanent magnets or stationary electro-magnets, into the elution buffer at well Eluate. Strategies for elution of nucleic acids from solid supports, e.g., microparticles, are known in the art. For example, but not by way of limitation, nucleic acids, e.g., RNA and/or DNA, can be eluted by contacting the solid supports to which the nucleic acids are bound, e.g., microparticles, with an elution buffer with or without concurrent heating. In certain embodiments, the elution buffer comprises phosphate (e.g., inorganic phosphate or organophosphate) at a concentration of 1 to 10 mM (e.g., 1, 2, 3, 4, 5, 6, 7, 8, 9, or 10 mM). In some embodiments, the phosphate concentration is chosen to preferentially bind and/or elute the nucleic acid, e.g., DNA or RNA.

Heating during positions W13-W20 incubation can be accomplished using, e.g., resistive heaters. In certain embodiments, the incubation extends for about 192 seconds. At the completion of the incubation, the microparticles are transferred back into the wash solution of well P3, leaving substantially microparticle-free eluate in the Eluate well. For example, such a transfer can occur at exemplary position W21. At W22, eluent can be aspirated and dispensed into one or more amplification vessels, as described further herein. For purpose of example and as embodied herein, approximately 42 μl (+/−5%) of eluent can be aspirated (e.g., after an about 12 second delay to cool eluent to 40° C.), and about half of the eluent can be dispensed into one or more amplification vessels.

In certain embodiments more than three washes can be employed in the context of the instant disclosure. Moreover, the systems of the present disclosure a capable of processing distinct samples, e.g., serum/plasma samples and whole blood samples, including with respect to the above-described steps or any step described below, such that individual samples can be handled in distinct manners in a single batch. For example, but not by way of limitation, individual samples in a batch can be incubated for longer or shorter periods and/or can be heated or cooled at distinct temperatures.

4.1.1.4. Eluate Transfer Systems

As embodied herein, after nucleic acid has been eluted from the microparticles, the resulting eluate can be separated from the microparticles by, for example, pipetting the eluate from the elution well and aspirating it to another vessel for amplification or removing the microparticles from the elution well. In certain embodiments, some or all of the eluate is transferred to a single reaction vessel which then undergoes an amplification process.

In certain embodiments, the eluate is split into a plurality of amplification vessels. In certain embodiments, a first portion of the eluate can be transferred to a first amplification vessel and a second portion of the eluent can be dispensed into a second amplification vessel. An exemplary embodiment of transferring and splitting eluate into an amplification process according to the exemplary embodiment shown in FIGS. 2A-2C is described below with respect to FIGS. 13A and 13B.

Figure 13A:
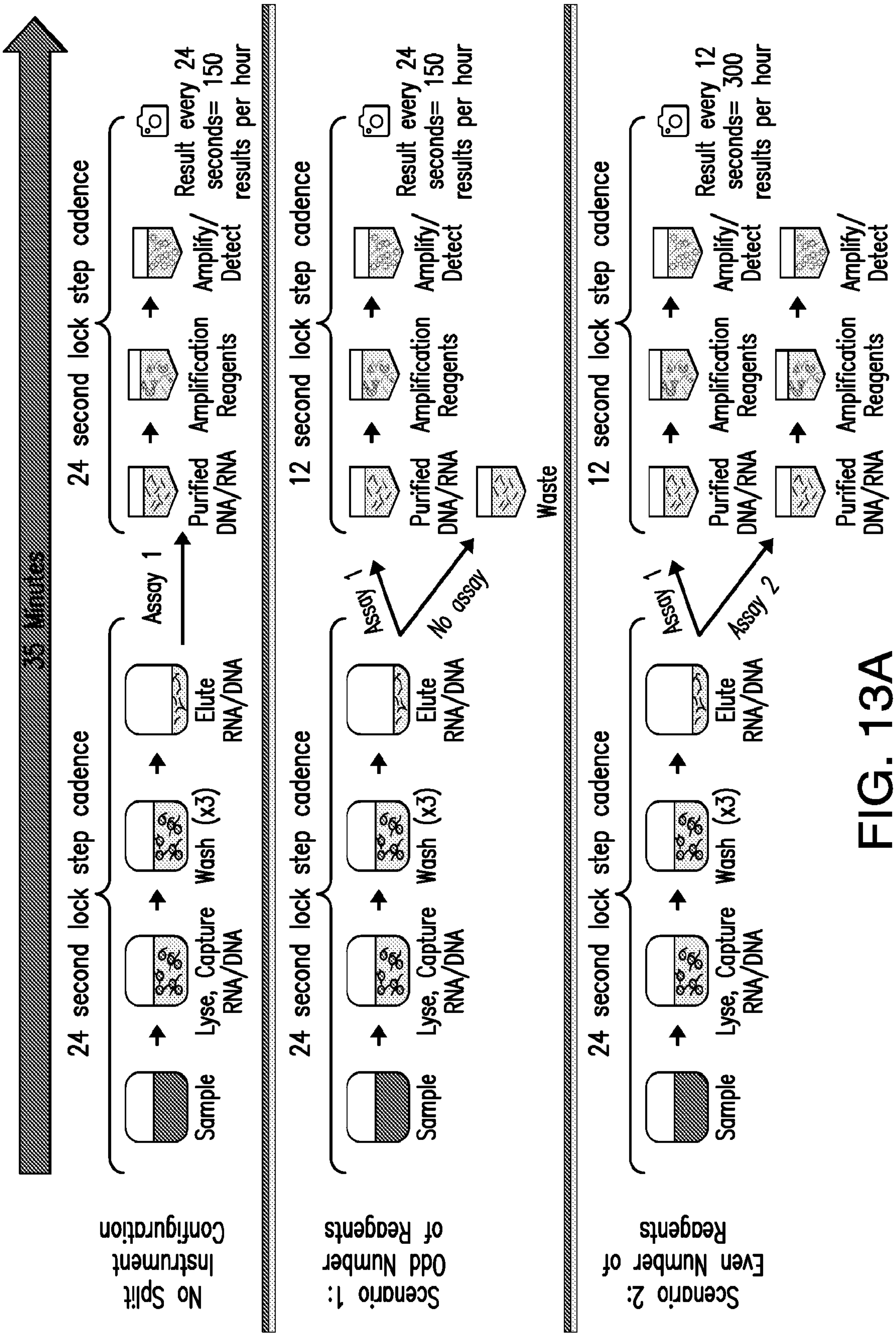
FIGS. 13A-13B depict exemplary embodiments of the split eluate aspect of the present disclosure.
Figure 13B:
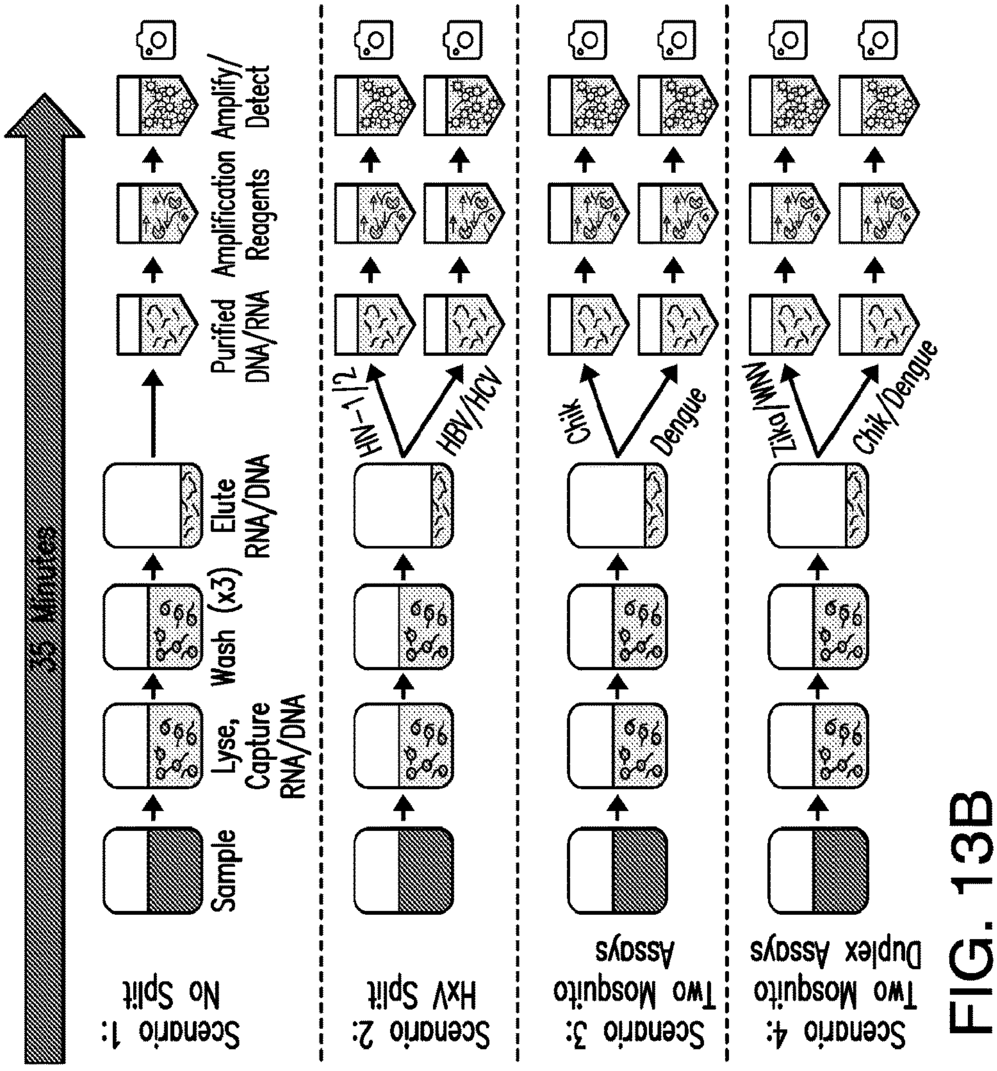

In certain embodiments, a "split eluate" approach is applicable to any elution strategy described herein. For example, and as illustrated in FIG. 13A and FIG. 13B, in addition to reducing the number sample preparations performed (and the associated consumables), splitting of the eluate can be used to increase the number of nucleic acid analyses performed, e.g., by creating additional opportunities for multiplexed amplification reactions from a single sample aspiration.

For example, in certain embodiments, the systems described herein are capable of aspirating a single sample for sample preparation every 24 seconds, which results in 150 sample aspirations per hour. In certain embodiments, and as illustrated in the top process of FIG. 13A, each sample aspirated is prepared and a single target nucleic acid is amplified and detected, leading to 150 results per hour. In certain embodiments, for example as embodied in the bottom process of FIG. 13A, each aspirated sample is prepared and the eluate containing nucleic acids for amplification is split into two amplification vessels, where each amplification reaction amplifies a single target nucleic acid for detection, leading to 300 results per hour. In certain embodiments, e.g., Scenarios 2 and 4 of FIG. 13B, each aspirated sample is prepared, and the eluate split into two amplifications, where each amplification reaction amplifies two target nucleic acids for detection, leading to 600 results per hour. In certain embodiments, each aspirated sample is prepared, and the eluate split into two amplifications, where each amplification reaction amplifies four or more target nucleic acids for detection, leading to 1,200 or more results per hour.

In certain embodiments, splitting an eluate as described herein can reduce assay development complexity and schedule. In addition, splitting an eluate as described herein can double the number of nucleic acid analyses performed for one sample preparation. For example, but not by way of limitation, assays requested contemporaneously can be grouped together to take advantage of eluate splitting; such as a "Mosquito Panel" of Chikungunya and Dengue or West Nile and Zika. Alternatively, or additionally, a single sample aspiration can be prepared by the methods and systems described herein and the nucleic acid eluate so prepared can be split into two amplifications reactions where one amplification reaction includes reagents suitable to amplify HIV-1, HIV-2, HCV, and HBV (e.g., an HxV multiplex amplification) and the second amplification reaction includes reagents suitable to amplify Parvovirus and HAV. In certain embodiments, the ability to detect HIV-1, HIV-2, HCV, HBV, Parvovirus and HAV from a single sample aspiration find particular use in connection with screening of plasma samples. As a result of performing less sample preparations per assay, splitting an eluate as described herein can reduce the solid waste associated with the eliminated sample preparations. Furthermore, as a result of performing less sample preparations per assay, splitting an eluate as described herein reduces the liquid and solid waste associated with the eliminated sample preparations.

4.1.2. Target Nucleic Amplification Systems

As embodied herein, nucleic acid analysis can include an amplification process configured to facilitate the amplification of the target nucleic acid. For example, but not by way of limitation, the amplification system can comprise reaction vessels into which nucleic acid isolated via the sample preparation methods and systems described herein have been transferred. In certain embodiments the reaction vessels will traverse a plurality of positions within the amplification system, e.g., reagent addition positions, heating positions, and/or cooling positions. In other embodiments, the reaction vessels are essentially stationary, and the reagent addition is accomplished via, e.g., robotic pipettors, and the heating and cooling can be accomplished via heating and/or cooling localized to the stationary position of the reaction vessel.

Figure 12:
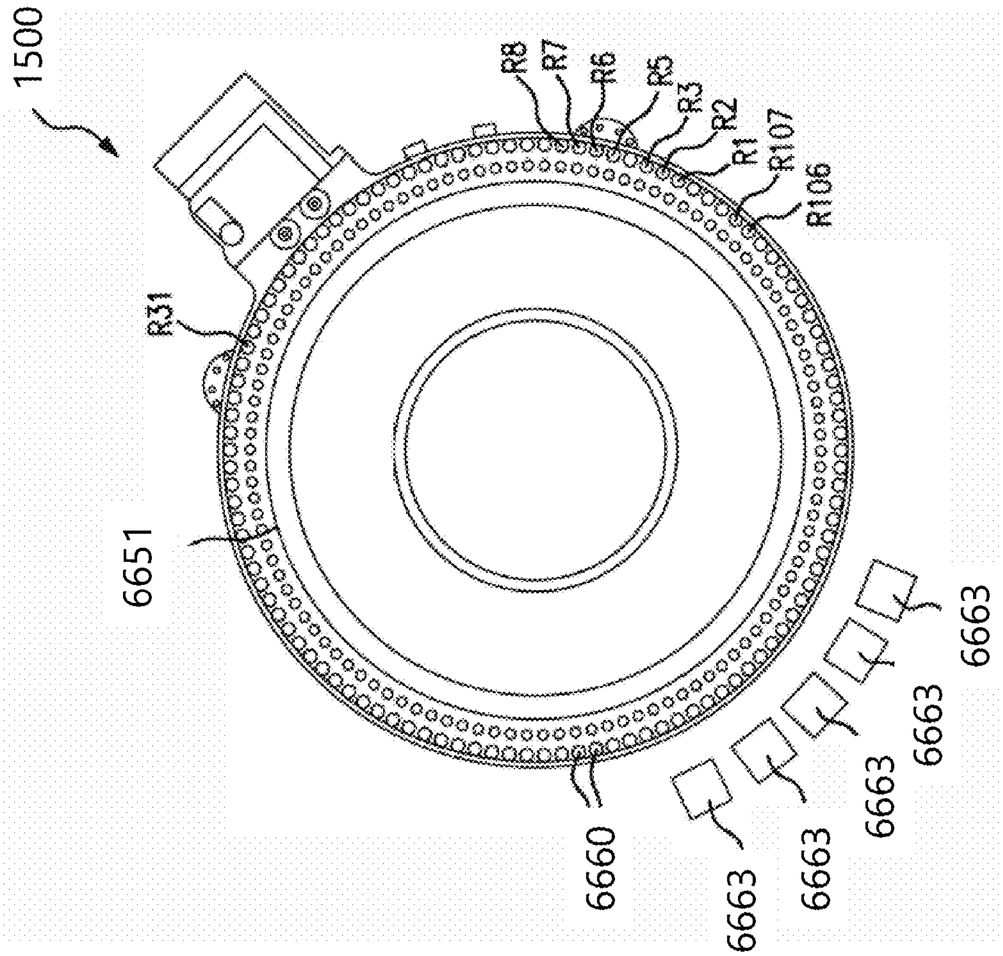
FIG. 12 depicts an exemplary amplification and detection subsystem.

As embodied herein, system 1000 can include a combined amplification and detection system subsystem 1500. For purpose of illustration and not limitation, an exemplary amplification/detection system 1500 is depicted in FIG. 12. Generally, the combined amplification/detection system amplifies the target to obtain a detectable signal and detects the signal. As embodied herein, the amplification operation can be any of a variety of strategies to amplify the target nucleic acid. For example, but not by way of limitation, the amplification operation can employ isothermal amplification. As discussed in detail, above, non-limiting examples of isothermal amplification operations useful in connection with the disclosed subject matter include RPA, NEAR, and Transcription Mediated Amplification ("TMA"), as well as any other suitable isothermal amplification technique.

The below table, Table 4, depicts exemplary times and operations regarding the amplification and detection process. In certain embodiments, as shown in FIG. 12 for illustration and not limitation, the amplification and detection system 1500 is a rotatable carousel 6651 having positions to hold amplification vessel 6660. The amplification vessel 6660 holds the amplification reagents and eluate during the amplification and detection process. In the embodiment of FIG. 12, the carousel has 107 positions (R1-R106). Not all positions on the carousel 6651 are used in the sample amplification process in that some position are used to load the amplification vessel 6660 onto the carousel 6651, dispense amplification reagents or remove the amplification vessel. As shown in this exemplary embodiment using a lockstep of 12 seconds, the sample processing time for the amplification and detection process is 1224 seconds, or 20.4 minutes.

TABLE 4

| Pos. | Function | Sample Process Time (Seconds) |
|---|---|---|
| R1 | Load Amp Vessel Cap | |
| R2 | Load Amp Vessel | |
| R3 | No operation | |
| R4 | Dispense Activator to Amp Vessel (3-8 μl +/−5%; assay specific volume) | |
| R5 | Dispense Eluent to Amp Vessel (3-8 μl +/−5%; assay specific volume) 20 μl +/−5%) Wash Probe Seal Amp Vessel | 12 |
| R6 | Dispense MasterMix to Amp Vessel (10 μl +/−5%; 15 μl +/−5%, 30 μl +/−5%) Wash probe Seal Amp Vessel | 12 |
| R7 | Vigorous Mixing (@12 seconds) | 12 |
| R8-106 | Incubation (40 °C) Continuous Reading of 5 channels every second lockstep Indexing | 1188 |
| [R31] | [Additional Vigorous Mixing Step] | |
| R107 | Transfer Amp Vessel to Waste | |

FIG. 12 includes positions R1-R107, a subset of which are positioned relative to one or more fluorescent readers 6663, but which also function as amplification positions. In certain embodiments, the system and methods can employ, one, two, three, four, five, six, seven, eight, nine, ten, or more readers. In certain embodiments, the system employs five readers. Each of said readers can be calibrated to detect a specific signal, e.g., a specific fluorescence signal. In certain embodiments each reader is calibrated to detect a different signal. In certain embodiments, each signal can be associated with a particular analyte of interest, e.g., an internal control or a target sequence. Embodiments of the present disclosure can comprise greater or fewer than the positions identified in FIG. 12, depending on alternative system configurations. For purpose of illustration not limitation, with reference to FIG. 12, the subsystem 1500 can include five fluorescent readers 6663 at different wavelengths to conduct optical detection of the amplification vessels.

Exemplary position R3 of FIG. 12 corresponds to the position where an activator is dispensed into, e.g., an amplification vessel, e.g., via "Sip & Spit" strategy from a reagent container. In certain embodiments, the activator is a material, e.g., an enzyme or cofactor, that initiates the amplification reaction.

Elute is then transferred to the amplification and detection system of FIG. 12. In one embodiment, about 40 μl of eluate is aspirated from the eluate well of a wash vessel 1710 and of the wash and elution system 1700. As mentioned above, in the embodiment of FIG. 12, the lockstep is 12 seconds, wherein the carousel indexes one position forward at each lockstep. In this embodiment, at position R5, about 20 μL of the eluate is the dispensed into an amplification vessel 6660 located on the amplification and detection carousel 6651. That amplification vessel is indexed to position R6 wherein at R6, the amplification reagents, sometimes referred to as a "MasterMix" are dispensed into the amplification vessel and the amplification vessel is capped. At the same time, the other about 20 μl of eluate is dispensed into another amplification vessel at R5. After the lockstep, the amplification vessel is indexed to R6 wherein amplification reagents are added, and the vessel is capped. As will be described in more detail below, after the second portion of the eluate is capped, the carousel rapidly rotates 360 degrees within the same lockstep so that each amplification vessel on the carousel can be read by one or more detectors every 24 seconds. By rotating the carousel 360 degrees every other 12 second lockstep (i.e., every 24 seconds), only capped amplification vessels are rotating thus reducing the chance of amplicon from contaminating the reaction carousel. Capping of the amplification vessels can be done, e.g., via use of a press on cap, heat stake tape, and/or PSA tape.

Positions R8-R106 are employed, in certain embodiments, to achieve an amplification incubation with, in certain embodiments, continuous mixing. In certain embodiments, the duration of the amplification incubation is about 1188 seconds. In certain embodiments, the R8-R106 incubation occurs at 40° C., where heating is performed via, in certain embodiments, resistive heaters. Continuous mixing at positions R8-R106 can be performed, in certain embodiments, via carousel movement and/or pop-up mixers. In certain embodiments, one or more positions, e.g., positions, including but not limited to, positions R7 and R31, are sites of vigorous mixing, e.g., mixing via pop-up mixer.

Exemplary position W19 of FIG. 10 corresponds to the position where an Activator is dispensed into, e.g., first and second amplification vessels, e.g., via "Sip & Spit" strategy from a reagent container. In certain embodiments, the Activator is a material, e.g., an enzyme or cofactor, that initiates the amplification reaction. Exemplary position W20 also functions to seal the exemplary first and second amplification vessels, e.g., via use of a press on cap, heat stake tape, and/or PSA tape. Position W20 can also allow for transfer of the first and second amplification vessels into the detection/read carousel, e.g., by use of a "press down/break frangible tab" and/or a "Pick & Place" strategy. Alternative strategies for transfer of the sample from position W20 to the detection/read carousel include using a separate vessel and cap resting within locations of the wash vessel, or separate vessels and caps loaded in various racks, which can be Picked & Placed into the proper location as required In certain embodiments, the combined Amplification/Detection system will rotate every amplification vessel past the readers each index period within the lockstep, e.g., achieving a 360 degree+one position movement in each index period. In certain embodiments, the lockstep is every 24 seconds, although different lock steps can be used. In certain embodiments the index period to complete the movement of the carousel is about 0.5 to about 2 seconds. In alternative embodiments the lockstep and/or index period can be reduced or increased, depending on throughput and TTR requirements.

In certain embodiments, the centrifugal force created during rotation of the combined Amplification/Detection system is taken advantage of to enhance sample processing. Depending on the final carousel diameter and gear ratios between the carousel and motor, one can rotate this carousel at about 600 RPM and produce approximately about 50 RCF (G forces) at each amplification vessel. This centrifugation force would, in certain embodiments, cause droplets on the side or top cover of the amplification vessel to return to the bottom (e.g., if the amplification vessels are allowed tilt during rotation). Droplets can be generated by vigorous mixing and/or combined Amplification/Detection system rotation. By returning any droplets to the bottom (read area) of the amplification vessel, the signal from the volume read and its integrity can be maximized.

4.1.3. Target Nucleic Acid Detection Systems

In accordance with another aspect of the disclosed subject matter, systems and methods for onboard pooling of samples for high-throughput analysis of the present disclosure can include a detection system configured to facilitate the detection of the target nucleic acid. For example, but not by way of limitation, the detection system can comprise reaction vessels where washed and eluted nucleic acid have been contacted with the materials necessary to amplify a target nucleic acid. In certain embodiments the reaction vessels will traverse a plurality of positions within the detection system, e.g., one or more readers. In other embodiments, the reaction vessels are essentially stationary, and the detection is accomplished via detectors that can be movably, e.g., robotically, localized to the stationary position of the reaction vessel. Additionally, or alternatively, in systems employing stationary amplification vessels, including but not limited amplification systems comprising partial or fully enclosed heating and/or cooling subsystems, the Detection systems of the present disclosure can incorporate fixed readers, e.g., incorporated into the housing of a partially or fully enclosed heating and/or cooling subsystem.

For purpose of illustration and not limitation, an exemplary combined Amplification/Detection system 1500 is depicted in FIG. 12. Generally, the combined amplification/detection system amplifies the target to obtain a detectable signal and detects the signal. As embodied herein, the amplification operation can be any of a variety of strategies to amplify the target nucleic acid. For example, but not by way of limitation, the amplification operation can employ isothermal amplification. As discussed in detail, above, non-limiting examples of isothermal amplification operations useful in connection with the disclosed subject matter include RPA, NEAR, and Transcription Mediated Amplification ("TMA"), as well as any other suitable isothermal amplification technique.

As described above, in certain embodiments, the combined amplification/detection system 1500 can rotate every amplification vessel past the readers every other lockstep (i.e., every 24 seconds) e.g., achieving a 360 degree in every second lockstep period. In certain embodiments, the lockstep is every 12 seconds, although different lock steps can be used. In alternative embodiments the lockstep and/or index period can be reduced or increased, depending on throughput and TTR requirements. In certain embodiments, the centrifugal force created during rotation of the combined Amplification/Detection system is taken advantage of to enhance sample processing. Depending on the final carousel diameter and gear ratios between the carousel and motor, one can rotate this carousel at about 600 RPM and produce approximately about 50 RCF (G forces) at each amplification vessel. This centrifugation force would, in certain embodiments, cause droplets on the side or top cover of the amplification vessel to return to the bottom (e.g., if the amplification vessels are allowed tilt during rotation). Droplets can be generated by vigorous mixing and/or combined Amplification/Detection system rotation. By returning any droplets to the bottom (read area) of the amplification vessel, the signal from the volume read and its integrity can be maximized.

Although reference has been made herein to nucleic acid analysis, systems and methods in accordance with the disclosed subject matter can incorporate additional or alternative high-throughput analyses as known in the art for analyzing biological samples. For purpose of example and not limitation, the high-throughput analysis can include a qualitative assay on the at least a fractionated portion of the pooled sample to detect one or more pathogen or infectious agent. In accordance with an aspect of the disclosed subject matter, the high-throughput analysis can include immunoassay analysis on the at least a fractionated portion of the pooled sample. For purpose of example and not limitation, the immunoassay analysis can include a digital immunoassay analysis. Additionally or alternatively, the high-throughput analysis can include clinical chemistry. Additionally or alternatively, the high-throughput analysis can include spectrophotometry.

4.2. Auxiliary Systems 4.2.1. Random Access Systems

For purpose of example and illustration, the systems of the present disclosure can provide random access to all samples and analyses, meaning that the system permits the ordering and processing of any sample and/or analysis in any order provided that the system has the necessary reagents/consumables for the requested analysis. For example, but not by way of limitation, because the systems of the present disclosure do not require batch processing, the systems allow for the prioritization of samples, e.g., allowing for "stat" samples to be prioritized over samples already in a queue. This is a significant improvement over current systems, where batch processing renders the prioritization of samples already in a queue or the introduction a sample to be prioritized over those already in the queue impossible. In certain embodiments, the random-access approach of the systems of the present disclosure provides for the rapid deconstruction of pooled samples should a pathogen or infectious agent be detected. For example, rather than waiting for the entire batch that included the positive pooled sample to be processed, the systems of the present disclosure allow for the prioritization of rescreening of sub-pools or individual donor samples to deconstruct the positive pooled sample, thereby substantially increasing overall efficiency of the donor blood screening process.

Additionally, or alternatively, and in accordance with another aspect of the disclosed subject matter, allowing for changes to the prioritization of samples after the samples have been loaded into the system, but before sample preparation has begun, or after sample preparation has completed, but before target amplification has begun, the random-access approach of the systems of the present disclosure can also allow for changes to the nucleic acid analysis applied to a sample or plurality of samples after preparation of the samples. For example, but not by way of limitation, because the systems of the present disclosure do not require batched processing, changes to the specific nucleic acid analysis implemented with respect to any particular sample can be modified prior the initiation of a nucleic acid analysis of the sample.

Additionally, or alternatively, the total number of nucleic acid analyses the systems of the present disclosure can perform can vary based on the system's ability to hold and access the nucleic acid analysis reagents necessary for carrying out sample preparation, amplification, and detection to determine the presence or absence in the sample of a particular pathogen or infectious agent. For example, in certain embodiments, the number of nucleic acid analyses available on a system of the present disclosure is 2 or more, 3 or more, 4 or more, 5 or more, 6 or more, 7 or more, 8 or more, 9 or more, 10 or more, 15 or more, 20 or more, 30 or more, 40 or more (e.g., 48 or more), or 50 or more nucleic acid analyses. In certain embodiments, the nucleic acid analyses can be performed in parallel.

For purpose of illustration not limitation, FIG. 1C depicts an exemplary sample loading bay 1630 configured to allow batch and individual rack sample loading. As embodied herein, the sample loading bay can load up to 360 samples and allow loading of different trays of samples for batch or individual loading.

4.2.2. Continuous Access Systems

Additionally, or alternatively, and in accordance with another aspect of the disclosed subject matter, the systems of the present disclosure, including systems capable of random access processing or batched processing, can include redundant components for sample processing and nucleic acid analysis, redundant loading/storage areas for, e.g., samples, reagents, sample processing cartridges, pipette tips, and/or the like. The redundant components enable the system to run (including presenting sample results/data) continuously and provide continuous operator access during the replenishment or removal of samples, bulk fluids, reagents, commodities (e.g., reaction vessels and reaction vessel caps, sample preparation (SP) cartridges, pipette tips and trays, assay plates, ancillary reagent packs, and/or the like), and waste, without ceasing operation of the system. By "continuous operator access" is meant an operator of the system can replenish and/or remove samples, bulk fluids, reagents, commodities, and waste without ceasing operation of the system, e.g., without interrupting any aspect of the sample preparation and analysis functions of the system. For purpose of illustration not limitation, the systems of the present disclosure can include a biohazard waste drawer, a reagent storage, a bulk solution drawer, a solid waste drawer, a consumable loader bay, a bulk solution reservoir and pump bay, a vacuum pump bay, a pipettor pump bay, and/or a liquid waste reservoir. An exemplary continuous operator access system to allow for continuous access and not requiring stopping the system to add samples and reagents to the system is disclosed in U.S. Pat. No. 9,335,338 and is herein incorporated by reference in its entirety.

4.2.3. Robotic Pipettors

Additionally, or alternatively, and in accordance with another aspect of the disclosed subject matter, the automated analysis systems of the present disclosure can include a robotic pipettor 1300. In certain embodiments, the robotic pipettor can access the system positions required for pipetting to accomplish, for example, sample preparation and processing, including pooling.

Additionally, or alternatively, the robotic pipettor 1300 can interact with, e.g., pipette tips at an internal location of the pipette tip loading area 1111; sample tubes at an internal location of the sample loading area 1100, ancillary reagents present at an ancillary reagent loading area, the sample transport 1200, assay reagents, a pipette tip and/or RV waste location, and the amplification and detection system 1500. In certain embodiments, the pipettor 1300 can perform, e.g., transfer of samples and reagents to pretreatment or lysis tubes; transfer pretreated samples from pretreatment tubes to lysis tubes; access eluate wells, auxiliary wells, and plunger disposal locations; access RV caps; fill RVs with eluate and reagents; access filled RVs; and access RV wells of the analysis station.

Additionally, or alternatively, a robotic pipettor of the present disclosure can be movable in the X, Y and Z axes (e.g., via drive/servo motor assemblies) to interact with one or more of the system areas/stations described herein.

Additionally, or alternatively, the robotic pipettor 1300 can include a camera for capturing images of the of the system for local analysis as well as remote analysis for purpose of maintenance, performance, automated correction, and the like. In some embodiments, the camera can also be used in reading barcodes present on assay plates and ancillary bottles. It can also be used to identify consumable characteristics, such as tip type.

For purpose of example and explanation and not limitation, the use of disposable pipette tips with the robotic pipettor 1300 can provide advantages, such as for system throughput. For example and not limitation and as embodied herein, the use of disposable pipette tips can allow additional time for the moveable robotic pipettor to aspirate and dispense samples during the 24 second period between rotations of the sample preparation carousel. As embodied herein, the ability to perform additional aspiration and/or dispense operations between movement of the carousel can allow for additional sample preparation steps, such as sample pooling, while minimizing the impacts on overall system throughput. For purpose of example and illustration and not limitation, washing reusable pipette tips can take longer than changing disposable pipette tips on the moveable robotic pipettor. Additionally or alternatively, additional hardware, such as pipette tip washing hardware, can be omitted when disposable pipette tips are used.

Additionally, or alternatively, the robotic pipettor 1300 includes features that find use, e.g., in reducing or eliminating cross-contamination. For example, in certain aspects, the robotic pipettor has one or more (e.g., any combination) of the following features: an air-based pipetting mechanism; the ability to detect the level of a liquid in a container (e.g., the liquid level in a sample tube, reagent tube, or well, etc.); the ability to aspirate from an upper level (e.g., the top) of a liquid to prevent liquid drop contamination on the outside of the pipette tips; pipette tip material that discourages or prevents liquid from clinging to the outside of pipette tips; the formation (or "aspiration") of an air gap to move aspirated liquid further up the pipette tip prior to movement, e.g., to prevent drips during movement (e.g., from a sample tube to a container into which the aspirated sample will be dispensed); one or more pressure sensors within the pipettor (e.g., one or more barrels of the pipettor) for sensing, e.g., fluid movement in the pipette tip (e.g., unanticipated fluid movement in the tip); a movement path such that the pipettor (e.g., with sample) never travels above an SP cartridge.

In accordance with an aspect of the disclosed subject matter, the system can include multiple pipettors. For purpose of example and illustration, a first pipettor can be used to samples from the sample loading area 1100 to the sample transport 1200, and a second pipettor can be used to pool the first sample and the second sample on the sample transport 1200.

5. Exemplary Embodiments

A. The present disclosure provides a an automated system for onboard pooling of samples for high-throughput analysis of the samples, comprising: a sample loading area for receiving a plurality of sample tubes, a sample transport configured to continually transport individual vessels along a transport path from a sample dispense position to a sample capture and transfer position, with intermediate positions therebetween; at least one pipettor to transfer a first sample from a first sample tube at the sample loading area and a second sample from a second sample tube at the sample loading area to the sample transport and to pool the first sample and the second sample in a vessel on the sample transport to form a pooled sample; and a sample transfer mechanism to capture at least a fractionated portion of the pooled sample from the vessel at the sample capture and transfer position and to transfer the at least a fractionated portion of the pooled sample for high-throughput analysis.

A1. The system of A, wherein the at least one pipettor is configured to transfer between 2 and 22 additional samples from respective sample tubes at the sample loading area to the sample transport and to pool the additional samples on the sample transport to form the pooled sample.

A2. The system of A-A1, wherein the first sample and the second sample are individual donor samples.

A3. The system of A-A1, wherein the first sample and the second sample are pooled samples.

A4. The system of A, A1 or A3, wherein the first sample and the second sample each include up to 48 pooled samples.

A4.1 The system of A, A1, A3, of A4, wherein the first sample and the second sample each include 48 pooled samples.

A5. The system of A-A3, wherein the sample transport comprises a sample preparation carousel A5.1 The system of A5, wherein the sample preparation carousel has positions to hold vessels around an outer perimeter of the sample preparation carousel.

A6. The system of A5.1, wherein the sample preparation carousel comprises between 5 to 40 positions.

A6.1. The system of A5.1-A6, wherein the sample preparation carousel has between 15 and 30 positions.

A7. The system of A-A6, wherein the system is configured to perform an onboard pooling process, a lysis process, and a pre-treatment process on the sample transport.

A8. The system of A-A7, wherein the sample transport rotates in a lockstep fashion, moving one position with each lockstep.

A9. The system of A8, wherein the duration of each lockstep is between about 15 and about 30 seconds.

A10. The system of A-A9, wherein the at least one pipettor is configured to transfer the first sample and the second sample to a first vessel at the sample dispense position prior to the sample transport transporting the first vessel to a first intermediate position.

A11. The system of A10, wherein the at least one pipettor is further configured to transfer a third sample and a fourth sample to the first vessel at the first intermediate position to add the third and fourth samples to the pooled sample.

A12. The system of A-A11, wherein the sample transport is configured to perform additional sample preparation.

A12.1 The system of A12 wherein the at least one pipettor is configured to transfer the pooled sample from the first vessel to a second vessel at the sample dispense position to initiate an additional sample preparation process for the pooled sample.

A13. The system of A12, wherein the additional sample preparation process is a lysis process.

A14. The system of A-A13, wherein the system is configured to perform a pre-treatment process, and wherein the at least one pipettor is configured to transfer the first sample to a first vessel at the sample dispense position prior to the sample transport transporting the first vessel to a first intermediate position, and wherein the at least one pipettor is configured to transfer the second sample to a second vessel at the sample dispense position A14.1 The system of A14, wherein the first vessel and the second vessel each include a reagent A14.2. The system of A14.1, wherein the sample transport is configured to continually transport the first vessel and the second vessel along the transport path and to mix the first vessel and the second vessel at each intermediate position.

A15. The system of A-A14.2, wherein the sample transport is configured to successively oscillate to mix the first and second samples in the vessel, the vessel moving in an arc with each oscillation.

A16. The system of A15, wherein the first and second samples are whole blood samples and wherein the reagent includes a lysis buffer.

A17. The system of A14-A16, wherein the pre-treatment process includes lysing the first sample and the second sample for between about 3 and about 6 minutes.

A18. The system of A14-A17, wherein the at least one pipettor is further configured to transfer the first and second samples from respective intermediate positions to a third vessel at the sample dispense position to pool the first sample and the second sample.

A19. The system of A-A18, wherein the first and second samples comprise whole blood, plasma, serum, cellular blood components, and/or other blood products.

A20. The system of A-A19, wherein the high-throughput analysis includes a nucleic acid analysis on the pooled sample.

A21. The system of A20, wherein the system is configured to determine a result from the nucleic acid analysis.

A22. The system of A21, wherein at least about 140 results are obtained per hour per $m^3$ of a volume occupied by the automated system.

A23. The system of A21-A22, wherein at least about 280 results are obtained per hour per $m^2$ of a footprint of the automated system.

A24. The system of A-A23, wherein the high-throughput analysis includes detection of one or more of a plurality of pathogens or infectious agents.

A25. The system of A24, wherein upon a determination of the presence of nucleic acids derived from each of the plurality of pathogens or infectious agents as a result of the nucleic acid analysis, the system is indicative of release of donor material associated with the pooled sample for clinical use.

A26. The system of A25, wherein upon a determination of the presence of a nucleic acid derived from at least one of the plurality of pathogens or infectious agents in the pooled sample, the system is configured to perform nucleic acid analysis of individual samples or sub-pools thereof included in the pooled sample and to make a determination whether donor material associated with each individual sample or sub-pool thereof is acceptable for clinical use based at least in part on the nucleic acid analysis of the individual samples or sub-pools thereof.

A27. The system of A26, wherein the pooled sample can include up to 96 individual donor samples, and wherein upon a determination of the presence of a nucleic acid derived from at least one of the plurality of pathogens or infectious agents in the pooled sample, the system is configured to make a determination whether donor material associated with each of the 96 individual donor samples is acceptable for clinical use in less than about 4 hours from initial aspiration of the first sample for nucleic acid analysis.

A28. The system of A27, wherein the system is configured to form a sub-pool on the sample transport and to perform nucleic acid analysis of the sub-pool.

A29. The system of A-A28, wherein the sample loading area is configured to store the first and second samples while the high-throughput analysis is performed on the pooled sample.

A29.1 The system of A29, wherein the pooled sample is a pool of 96 samples and wherein the 96 individual samples comprising the pooled sample are stored in the loading area while high-throughput analysis is performed on the pooled sample.

A29.2 The system of A29.1, wherein the 96 individual samples are stored in the loading area during onboard deconstruction of the pooled sample.

A30. The system of A-A29.2, wherein the high-throughput analysis includes a qualitative assay on the at least a fractionated portion of the pooled sample to detect one or more pathogen or infectious agent.

A31. The system of A30, wherein the plurality of pathogens or infectious agents are selected from the group consisting of: SARS-COV-2 (COVID-19), HIV-1, HIV-2, HBV, HCV, CMV, Parvo B19 Virus, HAV, *Chlamydia*, Gonorrhea, WNV, Zika Virus, Dengue Virus, Chikungunya Virus, Influenza, *Babesia*, Malaria, Usutu, and HEV.

A32. The system of A-A31, wherein the high-throughput analysis includes a digital immunoassay analysis on the pooled sample.

A34. The system of A31, wherein upon detection of a pathogen or infectious agent in the pooled sample, the system is configured to automatically deconstruct the pooled sample onboard.

A35. The system of A34, wherein upon detection of a pathogen or infectious agent in the pooled sample, the pipettor and sample transport are configured to automatically form sub-pools, each sub-pool comprising a subset of the first sample, second sample, and any additional samples in the pooled sample, and wherein the system is configured to perform a qualitative assay on each sub-pool to determine which sub-pool includes the pathogen or infectious agent.

A36. The system of A34, wherein the sample loading area is configured to store the first sample, second sample, and any additional samples used to form the pooled sample while high-throughput analysis is performed on the pooled sample, and wherein upon detection of a pathogen or infectious agent in the pooled sample, the pipettor is configured to automatically transfer the first sample, second sample, and any additional samples used to form the pooled sample from the respective sample tube at the sample loading area to the sample transport for sample preparation and further high-throughput analysis to determine which of the first sample, the second sample, or any additional sample used to form the pooled sample, includes the pathogen or infectious agent.

A37. The system of A-A36, wherein the at least one pipettor comprises a robotic pipettor with at least three degrees of freedom.

A38. The system of A-A37, wherein the at least one pipettor comprises a first robotic pipettor to transfer the first and second samples from the sample loading area to the sample transport, and a second robotic pipettor to pool the first sample and the second sample on the sample transport.

B. A method for onboard pooling of samples for high-throughput analysis of the samples, comprising: receiving a plurality of sample tubes at a sample loading area; transferring a first sample from a first sample tube at the sample loading area and a second sample from a second sample tube at the sample loading area to a sample dispense position on a sample transport; continually transporting individual vessels on the sample transport along a transport path from the sample dispense position to a sample capture and transfer position with intermediate positions therebetween; and pooling the first sample and the second sample in a vessel on the sample transport to form a pooled sample; and capturing at least a fractionated portion of the pooled sample from the vessel at the sample capture and transfer position for high-throughput analysis.

B1. The method of B, wherein the first sample and the second sample are individual donor samples.

B2. The method of B, wherein the first sample and the second sample are pooled samples.

B3. The method of B or B2, wherein the first sample and the second sample each include 48 pooled samples.

B4. The method of B-B3 wherein the sample transport comprises a sample preparation carousel having positions to hold vessels around an outer perimeter thereof, and wherein continually transporting individual vessels along the transport path includes rotating the sample preparation carousel.

B5. The method of B4, wherein the sample transport rotates in a lockstep fashion, moving one position with each lockstep.

B6. The method of B5, wherein the duration of each lockstep is between about 15 and about 30 seconds.

B7. The method of B-B6, wherein pooling the first sample and the second sample includes transferring the first sample and the second sample to a first vessel at the sample dispense position prior to the sample transport transporting the first vessel to a first intermediate position.

B8. The method of B7, further comprising transferring third and fourth samples to the first vessel at the first intermediate position to add the third and fourth samples to the pooled sample.

B9. The method of B7, further comprising transferring the pooled sample from the first vessel to a second vessel at the sample dispense position to initiate an additional sample preparation process for the pooled sample.

B10. The method of B9, wherein the additional sample preparation process is a lysis process.

B11. The method of B-10, further comprising a pre-treatment process, the pre-treatment process including transferring the first sample to a first vessel at the sample dispense position prior to the sample transport transporting the first vessel to a first intermediate position, and transferring the second sample to a second vessel at the sample dispense position; wherein the first vessel and the second vessel each include a reagent.

B11.1 The method of B-B11, further comprising mixing the first vessel and the second vessel at each intermediate position.

B12. The method of B-B11.1, further comprising mixing the first and second samples in the vessel, and wherein mixing the first and second samples in the vessel includes successively oscillating the sample transport, the vessel moving in an arc with each oscillation.

B12.1. The method of B12, wherein the successive oscillations are successive rotations of a sample preparation carousel.

B12.2. The method of B12-B12.1, wherein the successive oscillations comprise successive clockwise and counter-clockwise rotation.

B12.3. The method of B12-B12.2, wherein each clockwise rotation and counterclockwise rotation is about 10 degrees.

B12.4. The method of B12-B12.3, further comprising aspirating the pooled sample from the first sample vessel while the sample transport successively oscillates.

B13. The method of B-B12.4, wherein the first and second samples are whole blood samples and wherein the reagent includes a lysis buffer.

B14. The method of B-B13, wherein the method comprises a pre-treatment process, and the pre-treatment process includes lysing the first sample and the second sample for between about 3 and about 6 minutes.

B15. The method of B-B14, further comprising transferring the first and second samples from respective intermediate positions to a third vessel at the sample dispense position to pool the first sample and the second sample.

B16. The method of B-B15, wherein the first and second samples comprise whole blood, plasma, serum, cellular blood components, and/or other blood products.

B17. The method of B-B16, wherein the high-throughput analysis comprises a nucleic acid analysis on the pooled sample.

B18. The method of B17, further comprising determining a result from the nucleic acid analysis of the pooled sample.

B19. The method of B18, wherein at least about 140 results are obtained per hour per $m^3$ of a volume occupied by the automated system.

B20. The method of B18-B19, wherein at least about 280 results are obtained per hour per $m^2$ of a footprint of the automated system.

B21. The method of B18-B20, wherein the result includes detection of one or more of a plurality of pathogens or infectious agents.

B22. The method of B21, wherein a determination of the presence of nucleic acids derived from each of the plurality of pathogens or infectious agents as a result of the nucleic acid analysis is indicative of release of donor material associated with the pooled sample for clinical use.

B23. The method of B21-B22, wherein upon a determination of the presence of a nucleic acid derived from at least one of the plurality of pathogens or infectious agents in the pooled sample, the method further includes nucleic acid analysis of individual samples or sub-pools thereof included in the pooled sample and making a determination whether donor material associated with each individual sample or sub-pool thereof is acceptable for clinical use based at least in part on the nucleic acid analysis of the individual samples or sub-pools thereof.

B24. The method of B21-B23, wherein the pooled sample can include up to 96 individual donor samples, and wherein upon a determination of the presence of a nucleic acid derived from at least one of the plurality of pathogens or infectious agents in the pooled sample, the method further includes making a determination whether donor material associated with each of the 96 individual donor samples is acceptable for clinical use in less than about 4 hours from initial aspiration of the first sample for nucleic acid analysis.

B25. The method of B-B24, further comprising onboard pooling a subset of a plurality of samples included in the pooled sample on the sample transport to form a sub-pool for nucleic acid analysis of the sub-pool.

B26. The method of B-B25, further comprising storing the first and second samples at the sample loading area while the high-throughput analysis is performed on the pooled sample.

B27. The method of any one of B-B26, wherein the high-throughput analysis comprises a qualitative assay on the at least a fractionated portion of the pooled sample to detect a plurality of pathogens or infectious agents.

B28. The method of B27, wherein the plurality of pathogens or infectious agents are selected from the group consisting of: SARS-COV-2 (COVID-19), HIV-1, HIV-2, HBV, HCV, CMV, Parvo B19 Virus, HAV, *Chlamydia*, Gonorrhea, WNV, Zika Virus, Dengue Virus, Chikungunya Virus, Influenza, *Babesia*, Malaria, and HEV.

B29. The method of B27-B28, further comprising making a determination whether to release donor material associated with the pooled sample for clinical use based on the result of the qualitative assay.

B30. The method of B-B29, wherein the high-throughput analysis comprises a digital immunoassay analysis on the pooled sample.

B31. The method of B-B30, wherein upon detection of a pathogen or infectious agent in the pooled sample, the method further comprises onboard deconstruction of the pooled sample to determine which of the first sample, the second sample, or any additional sample in the pooled sample, includes the pathogen or infectious agent.

B32. The method of B-B31, further comprising:

storing the first sample, second sample, and any additional samples used to form the pooled sample at the sample loading area while high-throughput analysis is performed on the pooled sample; and upon detection of a pathogen or infectious agent in the pooled sample, automatically transferring the first sample, second sample, and any additional samples used to form the pooled sample from the respective sample tube at the sample loading area to the sample transport for sample preparation and further high-throughput analysis to determine which of the first sample, the second sample, or any additional sample used to form the pooled sample, includes the pathogen or infectious agent.

B33. The method of B and B2-B32, wherein the first sample and the second sample each include 48 samples.

B34. The method of B33, further comprising deconstructing the first sample and the second sample to determine which of the respective 48 samples includes the pathogen or infectious agent.

B35. The method of B-B34, further comprising onboard deconstruction of the pooled sample, including:

forming sub-pools, each sub-pool comprising a subset of the first sample, second sample, and any additional samples in the pooled sample; and performing a qualitative assay on each sub-pool to determine which sub-pool includes the pathogen or infectious agent.

B36. The method of B-B35, wherein the method is performed without manual intervention.

B37. The method B-B36, further comprising transferring between 2 and 22 additional samples from respective sample tubes at the sample loading area to the sample transport and pooling the between 2 and 22 additional samples in the tube.

B38. The method of B-B37, wherein between about 240 and about 340 samples are transferred from the sample loading area to the sample transport per hour.

Example 1: Onboard Pooling of 12 Samples for HTNAT

Figure 14B:
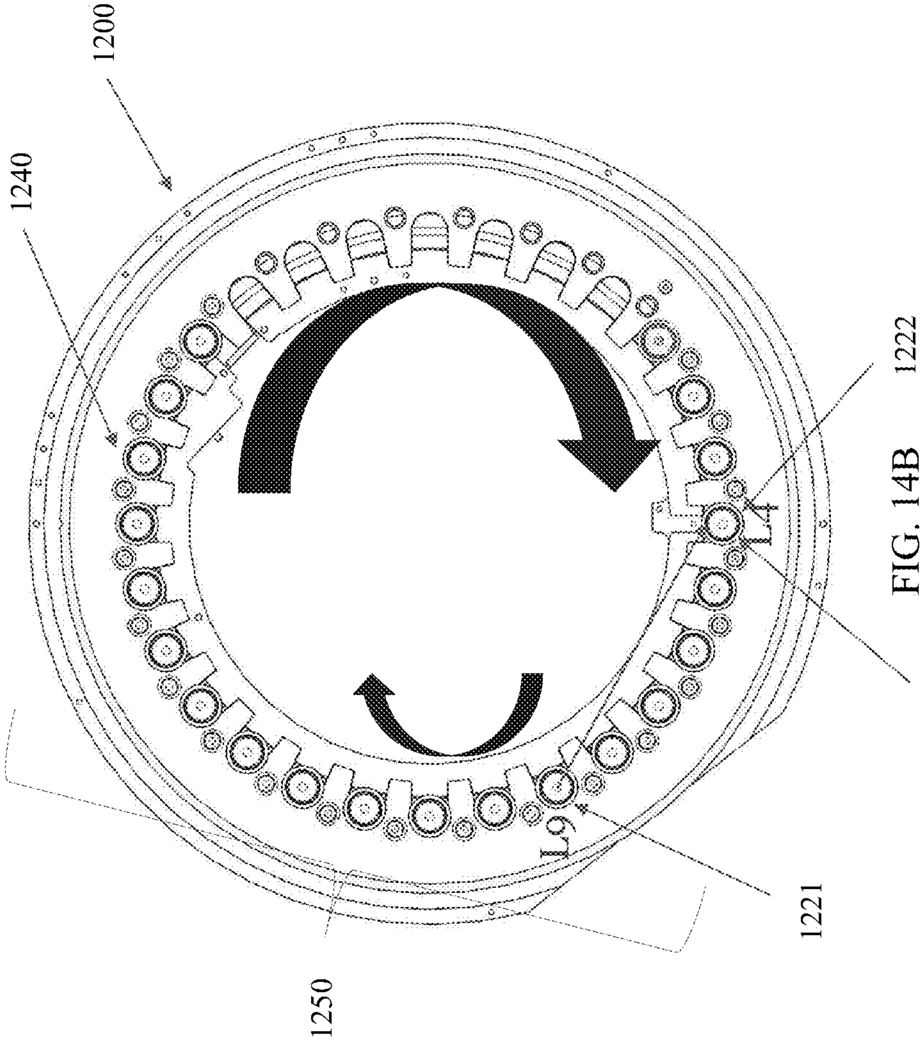
FIGS. 14A and 14B illustrate an exemplary method of onboard pooling of 12 samples in accordance with an aspect of the disclosed subject matter.
Figure 14A:
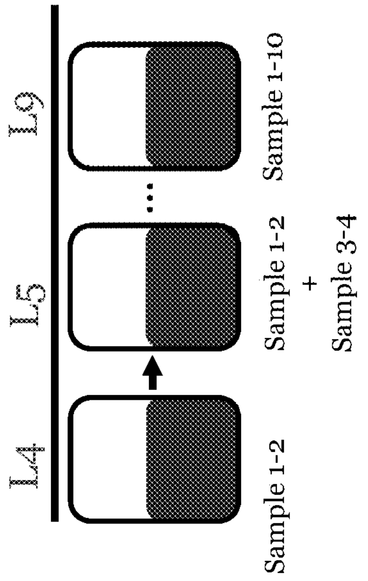
Figure 15B:
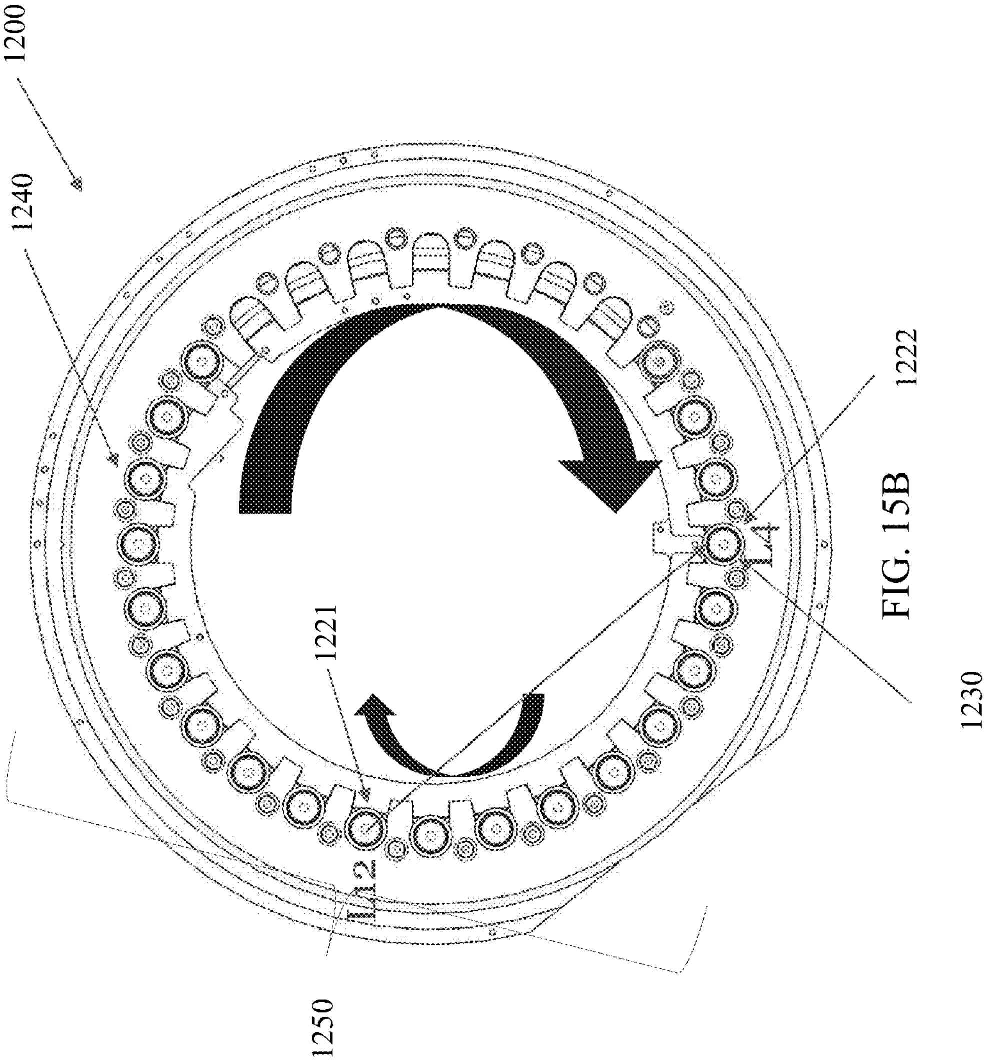
FIGS. 15A and 15B illustrate an exemplary method of onboard pooling of 18 samples in accordance with an aspect of the disclosed subject matter.
Figure 15A:
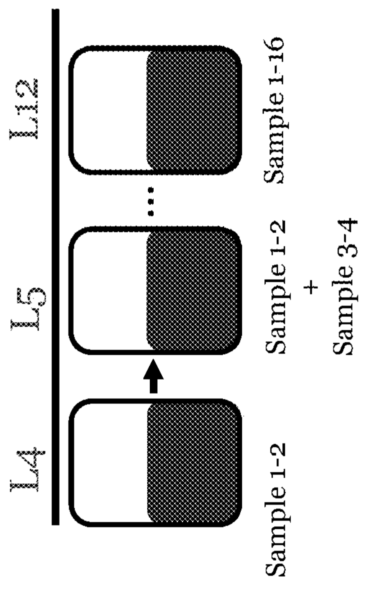
Figure 16B:
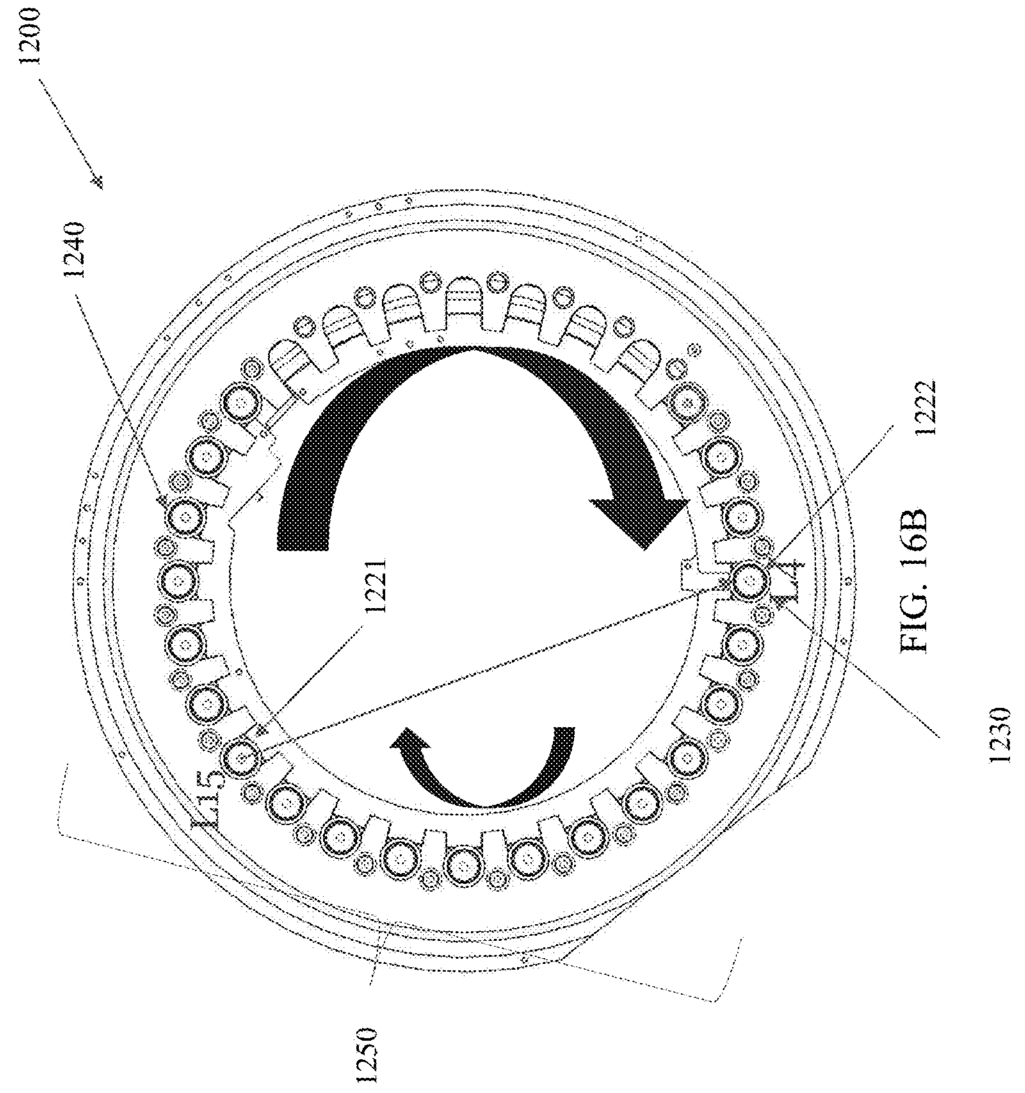
FIGS. 16A and 16B illustrate an exemplary method of onboard pooling of 24 samples in accordance with an aspect of the disclosed subject matter.
Figure 16A:
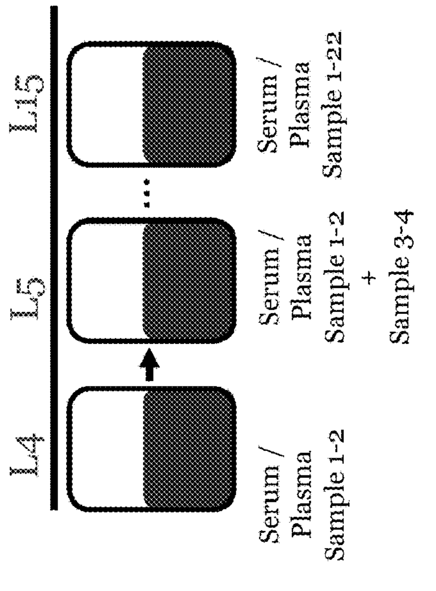

This example demonstrates an exemplary method for onboard pooling of 12 samples, such as serum or plasma samples, on a sample transport using an exemplary high-throughput nucleic acid testing (HTNAT) system such as that depicted in FIGS. 2A-2C. Exemplary HTNAT systems such as depicted in FIGS. 2A-2C can include a sample transport 1200 in the form of a rotatable sample preparation carousel, as described herein. With reference to the exemplary sample transport 1200 depicted in FIG. 14B, the sample transport 1200 can include 28 positions for holding tubes around an outer circumference of the sample transport. As embodied herein, the tubes can be lysis tubes. The notation L1-L21 is used herein with reference to positions on the sample preparation carousel. For purpose of this example, the carousel can be configured to move in a lockstep fashion, having about 24 seconds between movements of the carousel. As further embodied herein, the pipettor 1300 can be a robotic gantry pipettor. As described above, the pipettor 1300 can utilize disposable pipette tips to aspirate and dispense samples and/or pooled samples within the system 1000.

For purpose of example, pooling of 12 samples on the sample transport 1200 can be performed as follows with reference to the exemplary HTNAT system 100 depicted in FIGS. 2A-2C. A plurality of samples can be received at the sample loading area 1100. The plurality of samples can include at least 12 samples. First and second samples can be transferred from respective sample tubes at the sample loading area 1100 to a first vessel 1221 at sample dispense position L4 on the sample transport 1200. As embodied herein, the first vessel 1221 can be a lysis tube. The sample transport 1200 can then transport the first vessel 1221 to a first intermediate position L5, and third and fourth samples can be transferred from respective sample tubes at the sample loading area to the first vessel at the first intermediate position L5. The sample transport 1200 can then transport the first vessel 1221 to a second intermediate position L6 and additional samples can be transferred to the first vessel 1221 to add the additional samples to the pooled sample. This process can continue, and additional samples can be added to the pooled sample at successive intermediate positions.

For purpose of example and not limitation, the below table, Table 5, depicts an exemplary pooling process for pooling 12 samples on the sample transport 1200.

TABLE 5

| Position(s) | Description | Running Time |
|---|---|---|
| L4 (Start) | Aspirate Sample 1<br>Dispense Sample 1 to L4<br>Dispose of Tip<br>Aspirate Sample 2<br>Dispense Sample 2 to L4<br>Dispose of Tip | 24 sec |
| L5 | Aspirate Sample 3<br>Dispense Sample 3 to L5<br>Dispose of Tip<br>Aspirate Sample 4<br>Dispense Sample 4 to L5<br>Dispose of Tip | 48 sec |
| L6 | Aspirate Sample 5<br>Dispense Sample 5 to L6<br>Dispose of Tip<br>Aspirate Sample 6<br>Dispense Sample 6 to L6<br>Dispose of Tip | 72 sec |
| L7 | Aspirate Sample 7<br>Dispense Sample 7 to L7<br>Dispose of Tip<br>Aspirate Sample 8<br>Dispense Sample 8 to L7 | 96 sec |

TABLE 5-continued

| Position(s) | Description | Running Time |
|---|---|---|
| | Dispose of Tip | |
| L8 | Aspirate Sample 9<br>Dispense Sample 9 to L8<br>Dispose of Tip<br>Aspirate Sample 10<br>Dispense Sample 10 to L8<br>Dispose of Tip | 120 sec |
| L9 | Aspirate Sample 11<br>Dispense Sample 11 to L4<br>Dispose of Tip<br>Aspirate Sample 12<br>Aspirate Samples 1-10 from L9<br>Dispense Samples 1-10 and 12 to L4<br>Dispose of Tip | 144 sec |

As shown in the exemplary pooling process depicted in Table 5, two samples can be added to the pooled sample at the sample dispense position L4 and at successive intermediate positions (e.g., positions L5-L8). As further embodied herein, the pooled sample can be mixed at each intermediate position. Mixing the pooled sample can be used to achieve an even distribution of each of the individual donor samples within the pooled sample.

As embodied herein, at intermediate position L9, the pooled sample comprising samples 1-10 can be transferred from the first vessel 1221 at intermediate position L9 to a second vessel 1222 at the sample dispense position L4 of the sample transport 1200, and samples 11 and 12 can be transferred to the second vessel 1222 at the sample dispense position L4 to add samples 11 and 12 to the pooled sample. For example and as embodied herein, pipettor 1300 can aspirate sample 11 from the sample loading area 1100 and dispense sample 11 into the second vessel 1222 at the sample dispense position L4. Pipettor 1300 can further aspirate sample 12 from the sample loading area 1100, and with the same disposable pipette tip, pipettor 1300 can aspirate the pooled sample comprising samples 1-10 from intermediate position L9 and dispense samples 1-10 and 12 to the second vessel 1222 at the sample dispense position L4 to add samples 11 and 12 to the pooled sample.

Adding the last samples of the sample pool (e.g., samples 11 and 12 for a desired pool size of 12) directly to the second vessel 1222 can achieve a more even distribution of each of the individual donor samples within the pooled sample while minimizing the number of lock steps required to achieve the desired pooled size. For example, if samples 11 and 12 are transferred to the first vessel 1221 and the pooled sample is aspirated from the first vessel 1221 within the same lockstep, samples 11 and 12 could not have sufficient time to mix with the pooled sample prior to aspiration of the pooled sample, depending on the chosen lockstep time. For example, since pipettors sometimes do not aspirate the entire contents of a vessel, some of the pooled sample can remain in the first vessel 1221 after aspiration. Accordingly, it can be beneficial to ensure the pooled sample is adequately mixed prior to aspiration by the pipettor so that the volume of liquid aspirated can include an even distribution of the individual samples in the pooled sample.

For purpose of example and not limitation, the volume of each sample aspirated from the sample loading area and can be between about 80 and about 90 μL and the pooled sample can be between about 960 μL and about 1080 μL. As embodied herein, the volume of the pooled sample can be about 1000 μL. As embodied herein, with a desired pool sample volume of 1000 μL, the volume of each of the constituent samples used to form the pooled sample can be 1000 μL divided by the number of samples in the pooled sample (e.g., 1000 μL divided by 12 samples).

As described herein, after pooling samples 1-12, additional sample preparation can be performed on the pooled sample to further prepare the pooled sample for high-throughput analysis. For example and as embodied herein, the additional sample preparation can be a lysis process, and reagents, including lysis buffer, a protease, and CuTi-coated microparticles can be added to the second vessel 1222 and the pooled sample can be lysed in the second vessel 1222 on the sample preparation carousel as the pooled sample is continually transported along the transport path.

Nucleic acid from the pooled sample can be captured at the sample capture and transfer position 1240 of the sample transport 1200 and transferred for nucleic acid analysis. For example and as embodied herein, a sample transfer mechanism 1400 including a magnetic tip can be used to capture CuTi-coated microparticles and nucleic acid bound thereto from the second vessel 1222 and transfer the CuTi-coated microparticles and nucleic acid bound thereto to a wash and elution system 1700 for washing and elution of the nucleic acid from the pooled sample. As further embodied herein, the eluate can then be transferred to an amplification and detection carousel 1500 for detection of one or more of a plurality of pathogens or infectious agents in the pooled sample.

As embodied herein, 12 samples can be pooled on the sample transport in less than about 3 minutes. For purpose of example and as embodied herein, 12 samples, such as samples of plasma or serum, can be pooled on the sample transport in about 144 seconds from aspiration of the first sample from the sample loading area to dispensing of the pooled sample in the second vessel at the sample dispense position.

Exemplary HTNAT systems such as depicted in FIGS. 2A-2C can have a throughput of approximately 150 individual donor samples of serum or plasma per hour. For purpose of example and as embodied herein, processing serum or plasm samples can include a lysis process and an amplification and detection process, as described herein. Additionally, or alternatively, exemplary HTNAT systems as depicted in FIGS. 2A-2C can provide a time to result of about 20 to about 45 minutes for a determination of the presence or absence of nucleic acids derived from each of the plurality of pathogens or infectious agents based on the nucleic acid analysis. For purpose of example and as embodied herein, exemplary HTNAT systems as depicted in FIGS. 2A-2C can provide a time to result of about 35 minutes when processing individual donor samples of serum or plasma.

As embodied herein, onboard sample pooling can improve sample throughput with minimal impact on time-to-result performance. For purpose of example and as embodied herein, using a pool size of 12 as described above, exemplary systems such as depicted in FIGS. 2A-2C can have a throughput of approximately 25 pools of 12 serum or plasma sample per hours, which represents a throughput of approximately 300 individual donor samples of serum or plasma per hour and/or approximately 300 sample aspirations per hour. For purpose of example and as embodied herein, using a pool size of 12 as described above, exemplary systems such as depicted in FIGS. 2A-2C can perform about 25 amplifications per hour. Additionally or alternatively, using a pool size of 12 as described above, exemplary systems such as depicted in FIGS. 2A-2C can perform about 50 amplifications per hour such as by splitting the eluate containing nucleic acids from the pooled sample into two amplification vessels, as described further herein.

Additionally, or alternatively, exemplary HTNAT systems as depicted in FIGS. 2A-2C can provide a time to result of about 20 to about 45 minutes for a determination of the presence of nucleic acids derived from each of the plurality of pathogens or infectious agents based on the nucleic acid analysis of the pooled sample. For purpose of example and as embodied herein, exemplary HTNAT systems as depicted in FIGS. 2A-2C can provide a time to result of about 38 minutes when processing pools of 12 serum or plasma samples. For example and as embodied herein, onboard pooling as described herein can approximately double throughput with a minimal impact on time-to-result performance.

Example 2: Onboard Pooling of 18 Samples for HTNAT

This example demonstrates an exemplary method for onboard pooling of 18 samples, such as serum or plasma samples, on a sample transport using an exemplary HTNAT system such as that depicted in FIGS. 2A-2C. Exemplary HTNAT systems such as depicted in FIGS. 2A-2C can include a sample transport in the form of a rotatable sample preparation carousel, as described herein. With reference to the exemplary sample transport 1200 depicted in FIG. 15B, the sample transport 1200 can include 28 positions for holding vessels around an outer circumference of the sample transport. As embodied herein, the vessels can be lysis tubes. The notation L1-L21 is used herein with reference to positions on the sample preparation carousel. For purpose of this example, the carousel can be configured to move in a lockstep fashion, having about 24 seconds between movements of the carousel. As further embodied herein, the pipettor 1300 can be a robotic gantry pipettor. As described above, the pipettor 1300 can utilize disposable pipette tips to aspirate and transfer samples and/or pooled samples within the system 1000.

For purpose of example, pooling of 18 samples on the sample transport 1200 can be performed as follows with reference to the exemplary HTNAT system 100 depicted in FIGS. 2A-2C. A plurality of samples can be received at the sample loading area 1100. The plurality of samples can include at least 18 samples. First and second samples can be transferred from respective sample tubes at the sample loading area 1100 to a first vessel 1221 at sample dispense position L4 on the sample transport 1200. The sample transport 1200 can then transport the first vessel 1221 to a first intermediate position L5, and third and fourth samples can be transferred from respective sample tubes at the sample loading area to the first vessel at the first intermediate position L5. The sample transport 1200 can then transport the first vessel 1221 to a second intermediate position L6 and additional samples can be transferred to the first vessel 1221 to add the additional samples to the pooled sample. This process can continue, and additional samples can be added to the pooled sample at successive intermediate positions.

For purpose of example and not limitation, the below table, Table 6, depicts an exemplary pooling process for pooling 18 samples on the sample transport 1200.

TABLE 6

| Position(s) | Description | Running Time |
|---|---|---|
| L4 (Start) | Aspirate Sample 1<br>Dispense Sample 1 to L4<br>Dispose of Tip<br>Aspirate Sample 2<br>Dispense Sample 2 to L4<br>Dispose of Tip | 24 sec |
| L5 | Aspirate Sample 3<br>Dispense Sample 3 to L5<br>Dispose of Tip<br>Aspirate Sample 4<br>Dispense Sample 4 to L5<br>Dispose of Tip | 48 sec |
| L6 | Aspirate Sample 5<br>Dispense Sample 5 to L6<br>Dispose of Tip<br>Aspirate Sample 6<br>Dispense Sample 6 to L6<br>Dispose of Tip | 72 sec |
| L7 | Aspirate Sample 7<br>Dispense Sample 7 to L7<br>Dispose of Tip<br>Aspirate Sample 8<br>Dispense Sample 8 to L7<br>Dispose of Tip | 96 sec |
| L8 | Aspirate Sample 9<br>Dispense Sample 9 to L8<br>Dispose of Tip<br>Aspirate Sample 10<br>Dispense Sample 10 to L8<br>Dispose of Tip | 120 sec |
| L9 | Aspirate Sample 11<br>Dispense Sample 11 to L9<br>Dispose of Tip<br>Aspirate Sample 12<br>Dispense Sample 12 to L9<br>Dispose of Tip | 144 sec |
| L10 | Aspirate Sample 13<br>Dispense Sample 13 to L10<br>Dispose of Tip<br>Aspirate Sample 14<br>Dispense Sample 14 to L10<br>Dispose of Tip | 168 sec |
| L11 | Aspirate Sample 15<br>Dispense Sample 15 to L11<br>Dispose of Tip<br>Aspirate Sample 16<br>Dispense Sample 16 to L11<br>Dispose of Tip | 192 sec |
| L12 | Aspirate Sample 17<br>Dispense Sample 17 to L4<br>Dispose of Tip<br>Aspirate Sample 18<br>Aspirate Samples 1-16 from L12<br>Dispense Samples 1-16 and 18 to L4<br>Dispose of Tip | 216 sec |

As shown in the exemplary pooling process depicted in Table 6, two samples can be added to the pooled sample at the sample dispense position L4 and at successive intermediate positions (e.g., positions L5-L11). As further embodied herein, the pooled sample can be mixed at each intermediate position. Mixing the pooled sample can be used to achieve an even distribution of each of the individual donor samples within the pooled sample.

As embodied herein, at intermediate position L12, the pooled sample comprising samples 1-16 can be transferred from the first vessel 1221 at intermediate position L12 to a second vessel 1222 at the sample dispense position L4 of the sample transport 1200, and samples 17 and 18 can be transferred to the second vessel 1222 at the sample dispense position L4 to add samples 17 and 18 to the pooled sample.

For example and as embodied herein, pipettor 1300 can aspirate sample 17 from the sample loading area 1100 and dispense sample 17 into the second vessel 1222 at the sample dispense position L4. Pipettor 1300 can further aspirate sample 18 from the sample loading area 1100, and with the same disposable pipette tip, pipettor 1300 can aspirate the pooled sample comprising samples 1-16 from intermediate position L12 and dispense samples 1-16 and 18 to the second vessel 1222 at the sample dispense position L4 to add samples 17 and 18 to the pooled sample. Adding the last samples of the sample pool (e.g., samples 17 and 18 for a desired pool size of 18) directly to the second vessel 1222 can achieve a more even distribution of each of the individual donor samples within the pooled sample while minimizing the number of lock steps required to achieve the desired pooled size, as described above.

For purpose of example and not limitation, the volume of each sample aspirated from the sample loading area and can be between about 50 and about 60 μL and the pooled sample can be between about 900 μL and about 1080 μL. As embodied herein, the volume of the pooled sample can be about 1000 μL. As embodied herein, with a desired pool sample volume of 1000 μL, the volume of each of the constituent samples used to form the pooled sample can be 1000 μL divided by the number of samples in the pooled sample (e.g., 1000 μL divided by 18 samples).

As described herein, after pooling samples 1-18, additional sample preparation can be performed on the pooled sample to further prepare the pooled sample for high-throughput analysis. For example and as embodied herein, the additional sample preparation can be a lysis process, and reagents, including lysis buffer, a protease, and CuTi-coated microparticles can be added to the second vessel 1222 and the pooled sample can be lysed in the second vessel 1222 on the sample preparation carousel as the pooled sample is continually transported along the transport path.

Nucleic acid from the pooled sample can be captured at the sample capture and transfer position 1240 of the sample transport 1200 and transferred for nucleic acid analysis. For example and as embodied herein, a sample transfer mechanism 1400 including a magnetic tip can be used to capture CuTi-coated microparticles and nucleic acid bound thereto from the second vessel 1222 and transfer the CuTi-coated microparticles and nucleic acid bound thereto to a wash and elution system 1700 for washing and elution of the nucleic acid from the pooled sample. As further embodied herein, the eluate can then be transferred to an amplification and detection carousel 1500 for detection of one or more of a plurality of pathogens or infectious agents in the pooled sample.

As embodied herein, 18 samples can be pooled on the sample transport in less than about 4 minutes. For purpose of example and as embodied herein, 18 samples, such as samples of plasma or serum, can be pooled on the sample transport in about 216 seconds from aspiration of the first sample from the sample loading area to dispensing of the pooled sample in the second vessel at the sample dispense position.

Exemplary HTNAT systems such as depicted in FIGS. 2A-2C can have a throughput of approximately 150 individual donor samples of serum or plasma per hour. For purpose of example and as embodied herein, processing serum or plasm samples can include a lysis process and an amplification and detection process, as described herein. Additionally, or alternatively, exemplary HTNAT systems as depicted in FIGS. 2A-2C can provide a time to result of about 20 to about 45 minutes for a determination of the presence or absence of nucleic acids derived from each of the plurality of pathogens or infectious agents based on the nucleic acid analysis. For purpose of example and as embodied herein, exemplary HTNAT systems as depicted in FIGS. 2A-2C can provide a time to result of about 35 minutes when processing individual donor samples of serum or plasma.

As embodied herein, onboard sample pooling can improve sample throughput with minimal impact on time-to-result performance. For purpose of example and as embodied herein, using a pool size of 18 as described above, exemplary systems such as depicted in FIGS. 2A-2C can have a throughput of approximately 16-17 pools of 18 serum or plasma samples per hour, which represents a throughput of approximately 288-306 individual donor samples of serum or plasma per hour. For purpose of example and as embodied herein, exemplary systems such as depicted in FIGS. 2A-2C can have a throughput of approximately 16.7 pools of 18 serum or plasma samples per hour, which represents a throughput of approximately 300 individual donor samples of serum or plasma per hour and/or approximately 300 sample aspirations per hour. For purpose of example and as embodied herein, using a pool size of 12 as described above, exemplary systems such as depicted in FIGS. 2A-2C can perform about 25 amplifications per hour. Additionally or alternatively, using a pool size of 12 as described above, exemplary systems such as depicted in FIGS. 2A-2C can perform about 50 amplifications per hour such as by splitting the eluate containing nucleic acids from the pooled sample into two amplification vessels, as described further herein.

Additionally, or alternatively, exemplary HTNAT systems as depicted in FIGS. 2A-2C can provide a time to result of about 20 to about 45 minutes for a determination of the presence or absence of nucleic acids derived from each of the plurality of pathogens or infectious agents based on the nucleic acid analysis of the pooled sample. For purpose of example and as embodied herein, exemplary HTNAT systems as depicted in FIGS. 2A-2C can provide a time to result of about 39 minutes when processing pools of 18 serum or plasma samples. For example and as embodied herein, onboard pooling as described herein can approximately double sample throughput with a minimal impact on time-to-result performance.

Example 3: Onboard Pooling of 24 Samples

This example demonstrates an exemplary method for onboard pooling of 24 samples, such as serum or plasma samples, on a sample transport using an exemplary HTNAT system such as that depicted in FIGS. 2A-2C. Exemplary HTNAT systems such as depicted in FIGS. 2A-2C can include a sample transport in the form of a rotatable sample preparation carousel, as described herein. With reference to the exemplary sample transport 1200 depicted in FIG. 16B, the sample transport 1200 can include 28 positions for holding vessels around an outer circumference of the sample transport. As embodied herein, the vessels can be lysis tubes. The notation L1-L21 is used herein with reference to positions on the sample preparation carousel. For purpose of this example, the carousel can be configured to move in a lockstep fashion, having about 24 seconds between movements of the carousel. As further embodied herein, the pipettor 1300 can be a robotic gantry pipettor. As described above, the pipettor 1300 can utilize disposable pipette tips to aspirate and transfer samples and/or pooled samples within the system 1000.

For purpose of example, pooling of 24 samples on the sample transport 1200 can be performed as follows with reference to the exemplary HTNAT system 100 depicted in FIGS. 2A-2C. A plurality of samples can be received at the sample loading area 1100. The plurality of samples can include at least 24 samples. First and second samples can be transferred from respective sample tubes at the sample loading area 1100 to a first vessel 1221 at sample dispense position L4 on the sample transport 1200. The sample transport 1200 can then transport the first vessel 1221 to a first intermediate position L5, and third and fourth samples can be transferred from respective sample tubes at the sample loading area to the first vessel at the first intermediate position L5. The sample transport 1200 can then transport the first vessel 1221 to a second intermediate position L6 and additional samples can be transferred to the first vessel 1221 to add the additional samples to the pooled sample. This process can continue, and additional samples can be added to the pooled sample at successive intermediate positions.

For purpose of example and not limitation, the below table, Table 7, depicts an exemplary pooling process for pooling 24 samples on the sample transport 1200.

TABLE 7

| Position(s) | Description | Running Time |
|---|---|---|
| L4 (Start) | Aspirate Sample 1<br>Dispense Sample 1 to L4<br>Dispose of Tip<br>Aspirate Sample 2<br>Dispense Sample 2 to L4<br>Dispose of Tip | 24 sec |
| L5 | Aspirate Sample 3<br>Dispense Sample 3 to L5<br>Dispose of Tip<br>Aspirate Sample 4<br>Dispense Sample 4 to L5<br>Dispose of Tip | 48 sec |
| L6 | Aspirate Sample 5<br>Dispense Sample 5 to L6<br>Dispose of Tip<br>Aspirate Sample 6<br>Dispense Sample 6 to L6<br>Dispose of Tip | 72 sec |
| L7 | Aspirate Sample 7<br>Dispense Sample 7 to L7<br>Dispose of Tip<br>Aspirate Sample 8<br>Dispense Sample 8 to L7<br>Dispose of Tip | 96 sec |
| L8 | Aspirate Sample 9<br>Dispense Sample 9 to L8<br>Dispose of Tip<br>Aspirate Sample 10<br>Dispense Sample 10 to L8<br>Dispose of Tip | 120 sec |
| L9 | Aspirate Sample 11<br>Dispense Sample 11 to L9<br>Dispose of Tip<br>Aspirate Sample 12<br>Dispense Sample 12 to L9<br>Dispose of Tip | 144 sec |
| L10 | Aspirate Sample 13<br>Dispense Sample 13 to L10<br>Dispose of Tip<br>Aspirate Sample 14<br>Dispense Sample 14 to L10<br>Dispose of Tip | 168 sec |
| L11 | Aspirate Sample 15<br>Dispense Sample 15 to L11<br>Dispose of Tip<br>Aspirate Sample 16<br>Dispense Sample 16 to L11<br>Dispose of Tip | 192 sec |

TABLE 7-continued

| Position(s) | Description | Running Time |
|---|---|---|
| L12 | Aspirate Sample 17<br>Dispense Sample 17 to L12<br>Dispose of Tip<br>Aspirate Sample 18<br>Dispense Sample 18 to L12<br>Dispose of Tip | 216 sec |
| L13 | Aspirate Sample 19<br>Dispense Sample 19 to L13<br>Dispose of Tip<br>Aspirate Sample 20<br>Dispense Sample 20 to L13<br>Dispose of Tip | 240 sec |
| L14 | Aspirate Sample 21<br>Dispense Sample 21 to L14<br>Dispose of Tip<br>Aspirate Sample 22<br>Dispense Sample 22 to L14<br>Dispose of Tip | 264 sec |
| L15 | Aspirate Sample 23<br>Dispense Sample 23 to L4<br>Dispose of Tip<br>Aspirate Sample 24<br>Aspirate Samples 1-22 from L15<br>Dispense Samples 1-22 and 24 to L4<br>Dispose of Tip | 288 sec |

As shown in the exemplary pooling process depicted in Table 7, two samples can be added to the pooled sample at the sample dispense position L4 and at successive intermediate positions (e.g., positions L5-L14). As further embodied herein, the pooled sample can be mixed at each intermediate position. Mixing the pooled sample can be used to achieve an even distribution of each of the individual donor samples within the pooled sample.

As embodied herein, at intermediate position L15, the pooled sample comprising samples 1-22 can be transferred from the first vessel 1221 at intermediate position L12 to a second vessel 1222 at the sample dispense position L4 of the sample transport 1200, and samples 23 and 24 can be transferred to the second vessel 1222 at the sample dispense position L4 to add samples 23 and 24 to the pooled sample. For example and as embodied herein, pipettor 1300 can aspirate sample 23 from the sample loading area 1100 and dispense sample 23 into the second vessel 1222 at the sample dispense position L4. Pipettor 1300 can further aspirate sample 24 from the sample loading area 1100, and with the same disposable pipette tip, pipettor 1300 can aspirate the pooled sample comprising samples 1-22 from intermediate position L15 and dispense samples 1-22 and 24 to the second vessel 1222 at the sample dispense position L4 to add samples 23 and 24 to the pooled sample. Adding the last samples of the sample pool (e.g., samples 23 and 24 for a desired pool size of 24) directly to the second vessel 1222 can achieve a more even distribution of each of the individual donor samples within the pooled sample while minimizing the number of lock steps required to achieve the desired pooled size, as described above.

For purpose of example and not limitation, the volume of each sample aspirated from the sample loading area and can be between about 35 and about 45 μL and the pooled sample can be between about 840 μL and about 1080 μL. As embodied herein, the volume of the pooled sample can be about 1000 μL. As embodied herein, with a desired pool sample volume of 1000 μL, the volume of each of the constituent samples used to form the pooled sample can be 1000 μL divided by the number of samples in the pooled sample (e.g., 1000 μL divided by 24 samples).

As described herein, after pooling samples 1-24, additional sample preparation can be performed on the pooled sample to further prepare the pooled sample for high-throughput analysis. For example and as embodied herein, the additional sample preparation can be a lysis process, and reagents, including lysis buffer, a protease, and CuTi-coated microparticles can be added to the second vessel 1222 and the pooled sample can be lysed in the second vessel 1222 on the sample preparation carousel as the pooled sample is continually transported along the transport path.

Nucleic acid from the pooled sample can be captured at the sample capture and transfer position 1240 of the sample transport 1200 and transferred for nucleic acid analysis. For example and as embodied herein, a sample transfer mechanism 1400 including a magnetic tip can be used to capture CuTi-coated microparticles and nucleic acid bound thereto from the second vessel 1222 and transfer the CuTi-coated microparticles and nucleic acid bound thereto to a wash and elution system 1700 for washing and elution of the nucleic acid from the pooled sample. As further embodied herein, the eluate can then be transferred to an amplification and detection carousel 1500 for detection of one or more of a plurality of pathogens or infectious agents in the pooled sample.

As embodied herein, 24 samples can be pooled on the sample transport in less than about 5 minutes. For purpose of example and as embodied herein, 24 samples, such as samples of plasma or serum, can be pooled on the sample transport in about 288 seconds from aspiration of the first sample from the sample loading area to dispensing of the pooled sample in the second vessel at the sample dispense position.

Exemplary HTNAT systems such as depicted in FIGS. 2A-2C can have a throughput of approximately 150 individual donor samples of serum or plasma per hour. For purpose of example and as embodied herein, processing serum or plasm samples can include a lysis process and an amplification and detection process, as described herein. Additionally, or alternatively, exemplary HTNAT systems as depicted in FIGS. 2A-2C can provide a time to result of about 20 to about 45 minutes for a determination of the presence or absence of nucleic acids derived from each of the plurality of pathogens or infectious agents based on the nucleic acid analysis. For purpose of example and as embodied herein, exemplary HTNAT systems as depicted in FIGS. 2A-2C can provide a time to result of about 35 minutes when processing individual donor samples of serum or plasma.

As embodied herein, onboard sample pooling can improve sample throughput with minimal impact on time-to-result performance. For purpose of example and as embodied herein, using a pool size of 24 as described above, exemplary systems such as depicted in FIGS. 2A-2C can have a throughput of approximately 12-13 pools of 24 serum or plasma samples per hour, which represents a throughput of approximately 288-312 individual donor samples of serum or plasma per hour. For purpose of example and as embodied herein, exemplary systems such as depicted in FIGS. 2A-2C can have a throughput of approximately 12.5 pools of 24 serum or plasma samples per hour, which represents a throughput of approximately 300 individual donor samples of serum or plasma per hour and/or approximately 300 sample aspirations per hour. For purpose of example and as embodied herein, using a pool size of 24 as described above, exemplary systems such as depicted in FIGS. 2A-2C can perform about 12.5 amplifications per hour. Additionally or alternatively, using a pool size of 24 as described above, exemplary systems such as depicted in FIGS. 2A-2C can perform between about 25 amplifications per hour such as by splitting the eluate containing nucleic acids from the pooled sample into two amplification vessels, as described further herein.

Additionally, or alternatively, exemplary HTNAT systems as depicted in FIGS. 2A-2C can provide a time to result of about 20 to about 45 minutes for a determination of the presence or absence of nucleic acids derived from each of the plurality of pathogens or infectious agents based on the nucleic acid analysis of the pooled sample. For purpose of example and as embodied herein, exemplary HTNAT systems as depicted in FIGS. 2A-2C can provide a time to result of about 39 minutes when processing pools of 24 serum or plasma samples. For example and as embodied herein, onboard pooling as described herein can approximately double throughput with a minimal impact on time-to-result performance.

Example 4: Onboard Lysis Pre-Treatment and Pooling of 6 Sample Lysates

This example demonstrates an exemplary method for onboard lysis pre-treatment and pooling of 6 sample lysates on a sample transport using an exemplary HTNAT system such as that depicted in FIGS. 2A-2C. For example and as embodied herein, whole blood samples can be pre-treated and the whole blood lysate can be pooled.

Exemplary HTNAT systems such as depicted in FIGS. 2A-2C can include a sample transport in the form of a rotatable sample preparation carousel, as described herein. With reference to the exemplary sample transport 1200 depicted in FIG. 17, the sample transport 1200 can include 28 positions for holding vessels around an outer circumference of the sample transport. As embodied herein, the vessels can be lysis tubes. The notation L1-L21 is used herein with reference to positions on the sample preparation carousel. For purpose of this example, the carousel can be configured to move in a lockstep fashion, having about 24 seconds between movements of the carousel. As further embodied herein, the pipettor 1300 can be a robotic gantry pipettor. As described above, the pipettor 1300 can utilize disposable pipette tips to aspirate and transfer samples and/or pooled samples within the system 1000.

For purpose of example, lysis pre-treatment and pooling of 6 sample lysates on the sample transport 1200 can be performed as follows with reference to the exemplary HTNAT system 100 depicted in FIGS. 2A-2C. A plurality of samples can be received at the sample loading area 1100. The plurality of samples can include at least 6 samples. A first sample can be transferred from a first sample tube at the sample loading area 1100 to a first vessel 1221 at sample dispense position L4 on the sample transport 1200. The sample transport 1200 can then transport the first vessel 1221 to a first intermediate position L5. A second sample can be transferred from a second sample tube at the sample loading area 1100 to a second vessel 1222 at the sample dispense position L4 on the sample transport 1200. The sample transport 1200 can then transport the second vessel 1222 to the first intermediate position L5 and the first vessel 1221 to a second intermediate position L6. This process can continue, and additional samples can be added to additional vessels at the sample dispense position L4 as the sample transport 1200 continually transports individual vessels along the transport path.

For purpose of example and as embodied herein, lysis buffer can be added to the first vessel 1221, second vessel 1222 and additional vessels for samples 3-6, and samples 1-6 can lyse within their respective vessel as the sample transport 1200 continually transports the vessels along the transport path. As further embodied herein, samples 1-6 can be mixed at each intermediate position. Mixing the samples as they are transported along the transport path can be beneficial, for example, to mix the sample and lysis buffer, which can facilitate lysis of the samples.

For purpose of example and not limitation, the below table, Table 8, depicts an exemplary process for pre-treatment and pooling of sample lysates on the sample transport 1200.

TABLE 8

| Position(s) | Description | Time |
|---|---|---|
| L4 (Start) | Dispense Sample<br>Dispose of Tip | 24 sec |
| L5-L16 | Incubation and Mixing | 312 sec |
| L17 | Aspirate Sample 1 from L17<br>Aspirate Sample 2 from L16<br>Aspirate Sample 3 from L15<br>Aspirate Sample 4 from L14<br>Aspirate Sample 5 from L13<br>Aspirate Sample 6 from L12<br>Dispense Samples 1-6 to L4<br>Dispose of Tip | 336 |

Figure 17:
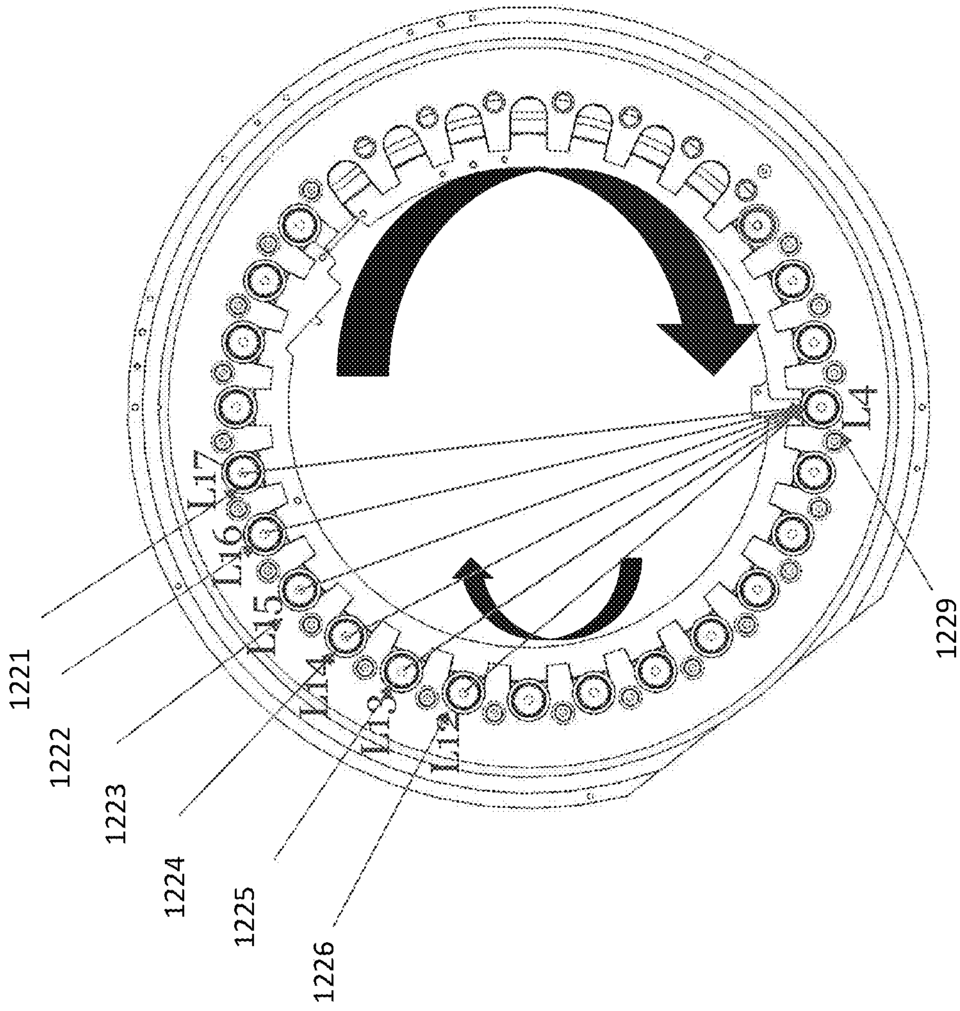
FIG. 17 illustrates an exemplary pre-treatment process and onboard pooling of pre-treated samples in accordance with an aspect of the disclosed subject matter.

As shown in the exemplary pre-treatment and pooling process depicted in Table 8 and FIG. 17, when the first sample in the first vessel 1221 reaches intermediate position L17, the first sample can be transferred from the from the first vessel 1221 at intermediate position L17 to a new vessel 1229 at the sample dispense position L4 and the second sample in the second vessel 1222 can be transferred from the second vessel 1222 at intermediate position L16 to the new vessel 1229 to pool the first and second sample lysates. Additionally, samples 3-6 can be transferred from their respective vessels and respective intermediate positions to the new vessel at the sample dispense position to add the sample 3-6 lysates to the pooled sample. For purpose of example and as embodied herein, samples 1-6 can be aspirated from their respective vessels and intermediate positions using one disposable tip and samples 1-6 can be dispensed into the new vessel at the sample dispense position in one dispense operation. Additionally or alternatively, samples 1-6 can be aspirated from their respective vessels and intermediate positions using separate tips and/or separate aspirations and dispenses.

For purpose of example and as embodied herein, during the pre-treatment, samples 1-6 can be allowed to lyse on the sample transport for between about 3 and about 6 minutes as the sample transport continually transports the vessels along the transport path. For purpose of example and as embodied herein, the first sample can be lysed for between about 5 and about 6 minutes, and the sixth sample can be lysed for between about 3 and about 4 minutes.

For purpose of example and not limitation, the volume of each of the pre-treated samples aspirated from the respective intermediate position and can be between about 45 and about 55 μL and the pooled sample can include between about 270 μL and about 330 μL of the pooled pre-treated samples. As embodied herein, the volume of the pooled pre-treated sample can be about 300 μL. As embodied herein, with a desired pooled pre-treated sample volume of 300 μL, the volume of each of the constituent pre-treated samples used to form the pooled sample can be 300 μL divided by the number of pre-treated samples in the pooled sample (e.g., 300 μL divided by 6 samples).

As described herein, after pooling samples 1-6, additional sample preparation can be performed on the pooled sample to further prepare the pooled sample for high-throughput analysis. For example and as embodied herein, the additional sample preparation can be a lysis process, and reagents, including lysis buffer, a protease, and CuTi-coated microparticles can be added to the second vessel 1222 and the pooled sample can be lysed in the second vessel 1222 on the sample preparation carousel as the pooled sample is continually transported along the transport path.

Nucleic acid from the pooled sample can be captured at the sample capture and transfer position 1240 of the sample transport 1200 and transferred for nucleic acid analysis. For example and as embodied herein, a sample transfer mechanism 1400 including a magnetic tip can be used to capture CuTi-coated microparticles and nucleic acid bound thereto from the second vessel 1222 and transfer the CuTi-coated microparticles and nucleic acid bound thereto to a wash track 1700 for washing and elution of the nucleic acid from the pooled sample. As further embodied herein, the eluate can then be transferred to an amplification and detection carousel 1500 for detection of one or more of a plurality of pathogens or infectious agents in the pooled sample.

As embodied herein, 6 samples can be pre-treated and pooled on the sample transport in less than about 6 minutes. For purpose of example and as embodied herein, 6 samples, such as whole blood samples, can be lysed on the sample transport and the lysates from the 6 samples can be pooled in about 336 seconds from aspiration of the first sample from the sample loading area to dispensing of the lysates the new vessel at the sample dispense position.

Exemplary HTNAT systems such as depicted in FIGS. 2A-2C can have a throughput of approximately 75 individual donor samples of whole blood per hour when the whole blood samples are pre-treated onboard but not pooled onboard. For purpose of example and as embodied herein, processing whole blood samples can include a pretreatment process, a lysis process, and an amplification and detection process, as described herein. Additionally, or alternatively, exemplary HTNAT systems as depicted in FIGS. 2A-2C can provide a time to result of about 20 to about 45 minutes for a determination of the presence or absence of nucleic acids derived from each of the plurality of pathogens or infectious agents based on the nucleic acid analysis. For purpose of example and as embodied herein, exemplary HTNAT systems as depicted in FIGS. 2A-2C can provide a time to result of about 42 minutes when processing individual donor samples of whole blood, including onboard pre-treatment.

As embodied herein, onboard pre-treatment and sample pooling can improve sample throughput with minimal impact on time-to-result performance. For purpose of example and as embodied herein, using a pool size of 6 as described above, exemplary systems such as depicted in FIGS. 2A-2C can have a throughput of approximately 19-23 pools of 6 whole blood samples per hour, which represents a throughput of approximately 114-138 individual donor samples of whole blood per hour. For purpose of example and as embodied herein, exemplary systems such as depicted in FIGS. 2A-2C can have a throughput of approximately 21 pools of 6 whole blood samples per hour, which represents a throughput of approximately 126 individual donor samples of serum or plasma per hour and/or approximately 126 sample aspirations per hour. For purpose of example and as embodied herein, using a pool size of 6 as described above, exemplary systems such as depicted in FIGS. 2A-2C can perform about 21 amplifications per hour. Additionally or alternatively, using a pool size of 6 as described above, exemplary systems such as depicted in FIGS. 2A-2C can perform between about 42 amplifications per hour such as by splitting the eluate containing nucleic acids from the pooled sample into two amplification vessels, as described further herein.

Additionally, or alternatively, exemplary HTNAT systems as depicted in FIGS. 2A-2C can provide a time to result of about 20 to about 45 minutes for a determination of the presence of nucleic acids derived from each of the plurality of pathogens or infectious agents based on the nucleic acid analysis of the pooled sample. For purpose of example and as embodied herein, exemplary HTNAT systems as depicted in FIGS. 2A-2C can provide a time to result of about 42 minutes when processing pools of 6 whole blood samples. For example and as embodied herein, onboard pooling as described herein can increase throughput with a minimal impact on time-to-result performance.

Example 5: Pooling with Liquid Handler and Onboard Pooling

This example demonstrates an exemplary method for pooling samples using both conventional pooling, such as on a dedicated liquid handler or pooler, and onboard pooling. For purpose of example and as described herein, using conventional pooling with a separate liquid handler and onboard pooling in combination can improve laboratory efficiency and throughput.

As embodied herein, a pooled sample of 96 samples can be formed using onboard pooling of first and second samples on an exemplary HTNAT system such as that depicted in FIGS. 2A-2C. For purpose of this example, the first and second samples can each be pools of 48 samples. As embodied herein, the first and second samples can be prepared on a dedicated liquid handler.

Onboard pooling of the first and second samples includes receiving the first and second samples at a sample loading area 1100 of the system 1000 and transferring the first and second samples from the sample loading area 1100 to a sample dispense position 1230 on a sample transport 1200. Onboard pooling of the first and second samples further includes continually transporting individual vessels 1220 on the sample transport 1200 along a transport path from the sample dispense position 1230 to a sample capture and transfer position 1240 with intermediate positions 1250 therebetween and pooling the first sample and the second sample in a vessel on the sample transport 1200 to form a pooled sample. As embodied herein, pooling the first and second sample can include transferring the first sample and the second sample to a first vessel 1221 at the sample dispense position 1230 prior to the sample transport transporting the first vessel 1221 to a first intermediate position 1251. The pooled sample can then be transported along the transport path to the sample capture and transfer position, where at least a fractionated portion of the pooled sample is captured for high-throughput analysis of the pooled sample of 96.

For purpose of background and illustration, in a plasma laboratory, liquid handler pooling throughput, not instrument throughput, can be the limiting factor. For example, plasma labs often use pool sizes of 96 samples, which can be prepared on 8-channel liquid handlers. The ratio of liquid handlers to testing instruments, such as NAT instruments, can be as high as 8 liquid handlers to 1 testing instrument. For purpose of example and illustration, conventional NAT platforms used in plasma labs can process up to 4,032 tests per day on pooled samples of 96 prepared on a traditional liquid handler, and plasma labs can run 2 tests per pooled sample, so a single conventional NAT instrument can process approximately 193,536 samples per day (e.g., [(4,032 tests)/(2 tests per pooled sample)]*96 samples per pool=193,536 samples per day).

For purpose of background and illustration, conventional liquid handlers often use an 8-channel pipettor, and during pooling, 768 samples are placed on the liquid handler and pipetted, 8 at a time, into 8 master pool tubes. After 96 cycles, 8 pools of 96 can be prepared and can be moved to an instrument for analysis. This can be the most efficient method to create pools of 96 on a conventional liquid handler. For example, when pooling on a liquid handler, the number of pools created can be a whole number multiple of the number of pipetting channels of the liquid handler to minimize the number of pipetting cycles need to form each pool and to maximize the use of the available pipette channels.

Although 8-channel pipettors are common on conventional liquid handlers, liquid handlers are available in configurations up to 16-channels. However, 16-channel liquid handlers are often not used when forming pools of 96 due to liquid handler size restrictions. For example, many liquid handlers cannot hold the 1,536 samples needed to create 16 pools of 96 using a 16-channel pipettor. As a result, 16-channel liquid handlers can be limited to creating 16 pools of 48 with 768 samples due to restrictions on the number of samples that the liquid handler can hold. The pooling throughput of 16-channel liquid handlers can be close to double the throughput of the conventional 8-channel configuration. For example, 768 samples can be transferred into 16 pools of 48 with 48 moves of a 16-channel pipettor, whereas 768 samples can be transferred into 8 pools of 96 with 96 moves of an 8-channel pipettor. However, plasma labs generally prefer to use larger pool sizes as the cost of testing can be reduced with larger pool sizes. For example, plasma laboratories often prefer pools of 96 as compared to pools of 48.

As embodied herein, using a combination of pooling with a 16-channel liquid handler and onboard pooling, can increase overall laboratory pooling throughput and can reduce the number of liquid handlers required to support each testing instrument. For example, by using onboard pooling to form a pool of 96 by pooling first and second samples comprising pools of 48 prepared on a liquid handler, 16-channel liquid-handler configurations can be used, which can double laboratory pooling throughput and can half the ratio of liquid handlers to instruments to 4:1, while maintaining a pool size of 96.

Although this example has been described in the context of onboard pooling of 2 pools of 48 prepared on a liquid handler to form a pool of 96, it is to be understood that additional or alternative configurations can be used. For example and not limitation, two or more pools of 48 prepared on a liquid handler can be pooled onboard to create larger pools, such as pools of 144 or pools of 192 or pools of 240.

Example 6: Pooling with Liquid Handler and Onboard Pooling and Onboard Deconstruction This example demonstrates an exemplary method for onboard deconstruction of a pooled sample. For example, when a pooled sample is determined to be positive, or reactive, the pooled sample can be deconstructed to identify which sample or samples used to form the pooled sample are positive or reactive. For purpose of example and as embodied herein, high-throughput nucleic acid analysis can be performed on the pooled sample, and a positive pooled sample can be identified based upon a determination of the presence of a nucleic acid derived from at least one of a plurality of pathogens or infectious agents in the pooled sample. As embodied herein, when it is determined that a pooled sample is positive, further nucleic acid analysis can be performed on the individual samples or sub-pools thereof that were used to form the positive pooled sample.

This example demonstrates an exemplary method for onboard deconstruction of pooled sample of 96 plasma samples using an exemplary HTNAT system such as that depicted in FIGS. 2A-2C. As described above, a pool of 96 samples can be formed, for example, using both offboard pooling, such as on a dedicated liquid handler or pooler, and onboard pooling. For example, and as embodied herein, a first sample comprising a pool of 48 and a second sample comprising a pool of 48 can be prepared on a dedicated liquid handler and the first and second samples can then be transferred to the sample loading area 1100 of a system for onboard pooling and high-throughput analysis, such as the exemplary HTNAT system 1000 depicted in FIGS. 2A-2C. As embodied herein, the first sample and the second sample used to form the pooled sample can be stored at the sample loading 1100 area while high-throughput analysis is performed on the pooled sample. Onboard pooling and HTNAT analysis of the pooled sample can be performed using the exemplary HTNAT system depicted in FIGS. 2A-2C and methods as described herein.

As embodied herein, upon a determination of the presence of a nucleic acid derived from at least one of a plurality of pathogens or infectious agents in the pooled sample of 96, the first sample and the second sample, each comprising a pool of 48 samples, can automatically be transferred from the sample loading area 1100 to the sample transport 1200 for further high-throughput analysis. For example and as embodied herein, the first and second samples can be transferred to the sample transport 1200 for a lysis process and for HTNAT analysis to determine the presence of a nucleic acid derived from at least one of a plurality of pathogens or infectious agents in the first sample or the second sample. Based on the results of the high-throughput analysis of the first sample and the second sample, it can be determined whether the first sample, the second sample, or both the first and second sample include nucleic acid derived from at least one of a plurality of pathogens or infectious agents.

The positive first and/or second sample can then be further deconstructed. For example and as embodied herein, the 48 individual samples used to form the positive first or second sample can then be transferred to the system 1000 for high-throughput analysis. Transferring the 48 individual samples to the system can be performed by an operator, or can be performed automatically such as by a laboratory automation system. Onboard pooling and high-throughput analysis of the 48 individual samples can then be performed as described herein. For example and as embodied herein, deconstructing the positive first or second sample can include onboard pooling to form three sub-pools of 16 individual samples and performing high-throughput analysis on each of the three sub-pools to determine which sub-pool is positive. As embodied herein, each of the three sub-pools can contain 16 individual samples representing a subset of the individual samples that had been used to form the positive first or second sample. Onboard pooling and HTNAT analysis of the sub-pools can be performed using the exemplary HTNAT system depicted in FIGS. 2A-2C and methods as described herein. Based on the results of the high-throughput analysis of the three sub-pools, it can be determined which sub-pool includes nucleic acid derived from at least one of a plurality of pathogens or infectious agents.

As embodied herein, the positive sub-pool(s) can then be further deconstructed. As embodied herein, deconstructing the positive sub-pool can include onboard pooling to form four sub-pools of 4 individual samples and performing high-throughput analysis on each of the four sub-pools of 4 individual samples to determine which of the sub-pools is positive. As embodied herein, each of the four sub-pools can contain 4 individual samples, representing a subset of the individual samples that had been used to form the positive sub pool of 16 individual samples. Onboard pooling and HTNAT analysis of the sub-pools can be performed using the exemplary HTNAT system depicted in FIGS. 2A-2C and methods as described herein. Based on the results of the high-throughput analysis of the four sub-pools, it can be determined which of the four sub-pools includes nucleic acid derived from at least one of a plurality of pathogens or infectious agents.

As embodied herein, the positive sub-pool of four individual samples can then be further deconstructed. As embodied herein, deconstructing the positive sub-pool of four individual samples can include performing high-throughput analysis of the four individual samples that had been used to form the positive sub-pool. HTNAT analysis of the individual samples can be performed using the exemplary HTNAT system depicted in FIGS. 2A-2C and methods as described herein. Based on the results of the high-throughput analysis of the four individual samples, it can be determined which of the four individual samples includes nucleic acid derived from at least one of a plurality of pathogens or infectious agents.

The systems and methods described herein can reduce the number of manual steps and the amount of time needed to deconstruct a pooled sample. For example, deconstructing a positive pool of 96 samples using conventional methods can take 12 hours or longer and can require multiple manual steps. For example, in conventional methods, when a positive pool of 96 is identified, a user can manually retrieve the 96 constituent samples and place them back on a liquid handler to be pooled into 16 sub-pools of 6. These 16 sub-pools can then manually be transported from the liquid handler to an instrument for analysis. Analysis of the 16 sub-pools can take up to 3.5-4 hours, after which the reactive sub-pool(s) can then be deconstructed. In conventional methods, the 6 samples in each reactive sub-pool are not stored on the instrument during testing, and must be retrieved and placed back on the instrument for individual testing (IDT). IDT of the 6 samples in each reactive sub-pool can take an additional ~3.5-4 hours to determine which of the individual sample(s) from the pooled sample are reactive. Using conventional methods, deconstructing a pool of 96 samples can take over 12 hours.

Systems and methods in accordance with the disclosed subject matter can reduce the amount of time and the number of manual steps for pool deconstruction. For example, and as embodied herein, based on the results of the high-throughput analysis, a determination can be made in less than about 4 hours as to which of the 96 individual samples used to form the pooled sample includes nucleic acid derived from at least one of a plurality of pathogens or infectious agents. As further embodied herein, a determination as to whether donor material associated with each of the 96 individual donor samples used to form the pooled sample is acceptable for clinical use can be made in less than about 4 hours from initial aspiration of the first sample for nucleic acid analysis.

Systems and methods for onboard pooling and high-throughput analysis in accordance with the disclosed subject matter can provide numerous advantages. For purpose of example and not limitations, systems and methods for onboard pooling in accordance with the disclosed subject matter can increase testing throughput and can reduce the number of tests required. For example, as compared with high-throughput analysis of individual samples, pooling as described herein can increase the number of individual samples tested per hour. Additionally or alternatively, using onboard pooling and high-throughput analysis to screen for pathogens or infectious agents can provide increased efficiency for the release of donor material associated with the pooled sample for clinical use and can reduce the total number of tests required to assess a given number samples, particularly when screening for pathogens or infectious agents with low prevalence in the sample population. Additionally or alternatively, systems and methods for onboard pooling in accordance with the disclosed subject matter can increase laboratory throughput by reducing laboratory bottlenecks associated with conventional pooling on separate liquid handlers or poolers.

Additional benefits of systems and methods for onboard pooling and high-throughput analysis in accordance with the disclosed subject matter can include, for example and not limitation, reducing time and equipment required for moving, storing, and retrieving samples for pool deconstruction. For example, with traditional testing methods results can take over 3 hours from aspiration of a sample for testing, and as such, samples undergoing analysis on conventional analyzers, such as analysis for pool deconstruction, can be removed from the analyzer while the analysis proceeds so other samples can be loaded. The samples undergoing analysis must then be placed somewhere else, often in a refrigerator to preserve the sample integrity. If further testing is needed the samples must then be retrieved. By contrast, with automated deconstruction of on-board pooled samples and high-throughput analysis as described herein, completed samples can begin deconstruction testing long before they need to be removed from the instrument to be replaced with other samples to meet the instrument throughput.

Additional benefits of systems and methods for onboard pooling and high-throughput analysis in accordance with the disclosed subject matter can include, for example and not limitation, reducing the number of liquid handlers or poolers needed in a laboratory to support high-throughput testing. For purpose of example and not limitation, by pooling samples onboard, the number of liquid handlers or poolers in a laboratory can be reduced, which can reduce costs (e.g., fewer pieces of equipment needed) and can free up laboratory floor space for alternative uses.

Additional benefits of systems and methods for onboard pooling and high-throughput analysis in accordance with the disclosed subject matter can include, for example and not limitation, pool size flexibility. For example, when pooling on conventional liquid handlers or poolers pool sizes are generally selected according to the number of pipette channels on the liquid handler or pooler. In accordance with an aspect of the disclosed subject matter, pool size can be selected as desired with minimal impacts on efficiency and throughput. For purpose of example and not limitation, pool size can be selected based on the prevalence of pathogens or infectious agents in the sample population. For example, with conventional pooling on a liquid handler, pool sizes are largely determined by liquid handler configuration, and many liquid handlers use 8-channel pipettors. With conventional pooling on a liquid handler, the cost of liquid handler and reduced liquid handler throughput when using smaller pool sizes can make using smaller pool sizes less desirable. As a result, when analyzing samples in medium-high prevalence regions, individual donor testing is frequently used, which can be a costly method of testing. Systems and methods for onboard pooling and high-throughput analysis in accordance with the disclosed subject matter can provide increased pool size flexibility, which can, for example, provide better lab performance and more flexibility when analyzing samples in medium-high prevalence regions (e.g., pools of 2-4 can be selected based on the prevalence of pathogens or infectious agents in the sample population).

Additional benefits of systems and methods for onboard pooling and high-throughput analysis in accordance with the disclosed subject matter can include, for example and not limitation, efficient use of laboratory floor space. For example, and as embodied herein, systems and methods for onboard pooling and high-throughput analysis can use system resources for multiple processes. For example and as embodied herein, the sample transport can be used for pooling, pre-treatment, and lysis processes. By using system components for multiple processes, the floor space required for high-throughput analysis can be reduced as compared to systems and methods which may require separate systems and floor space for each process. Additionally or alternatively, and as described above, additional equipment, such as poolers, can be reduced.

Additional benefits of systems and methods for onboard pooling and high-throughput analysis in accordance with the disclosed subject matter can include, for example and not limitation, reduced testing error. For purpose of example and not limitation, automated onboard deconstruction as described herein can reduce the manual steps and opportunities for error which can be associated with conventional deconstruction methods. For example and not limitation, using conventional pooling on a liquid handler, a minimum of 4 manual steps can be needed (e.g., load on pooler, unload from pooler, load on instrument, unload from instrument). For example and not limitation, systems and methods for onboard pooling and high-throughput analysis in accordance with the disclosed subject matter can reduce the minimum number of manual steps to 2 (e.g., load on instrument, unload from instrument).

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. An automated system for onboard pooling of samples for high-throughput analysis of the samples, comprising:

a sample loading area for receiving a plurality of sample tubes, a sample transport configured to continually transport individual vessels along a transport path from a sample dispense position to a sample capture and transfer position, with intermediate positions therebetween;

at least one robotic pipettor configured to transfer a first sample from a first sample tube at the sample loading area and a second sample from a second sample tube at the sample loading area to the sample transport and to pool the first sample and the second sample in a vessel on the sample transport to form a pooled sample; and a robotic sample transfer mechanism configured to capture at least a fractionated portion of the pooled sample from the vessel at the sample capture and transfer position and to transfer the at least a fractionated portion of the pooled sample to a subsequent process container for high-throughput analysis.

2. The system of claim 1, wherein the at least one robotic pipettor is configured to transfer between 2 and 22 additional samples from respective sample tubes at the sample loading area to the sample transport and to pool the additional samples on the sample transport to form the pooled sample.

3. The system of claim 1, wherein the first sample and the second sample are individual donor samples.

4. The system of claim 1, wherein the first sample and the second sample are pooled samples.

5. The system of claim 4, wherein the first sample and the second sample each include up to 48 pooled samples.

6. The system of claim 1, wherein the sample transport comprises a sample preparation carousel having positions to hold vessels around an outer perimeter of the sample preparation carousel.

7. The system of claim 6, wherein the sample preparation carousel comprises between 5 to 40 positions.

8. The system of claim 1, wherein the sample transport is configured for a lysis process and a pre-treatment process to be performed there along.

9. The system of claim 1, wherein the sample transport rotates in a lockstep fashion, moving one position with each lockstep.

10. The system of claim 9, wherein a duration of each lockstep is between about 15 and about 30 seconds.

11. The system of claim 1, wherein the at least one robotic pipettor is configured to transfer the first sample and the second sample to a first vessel at the sample dispense position prior to the sample transport transporting the first vessel to a first intermediate position.

12. The system of claim 11, wherein the at least one robotic pipettor is further configured to transfer a third sample and a fourth sample to the first vessel at the first intermediate position to add the third and fourth samples to the pooled sample.

13. The system of claim 12, wherein the sample transport is configured to perform additional sample preparation, and wherein the at least one robotic pipettor is further configured to transfer the pooled sample from the first vessel to a second vessel at the sample dispense position to initiate an additional sample preparation process for the pooled sample.

14. The system of claim 13, wherein a lysis buffer is disposed in the second vessel, and the additional sample preparation process is a lysis process.

15. The system of claim 1, wherein the system is configured to perform a pre-treatment process wherein the at least one robotic pipettor is configured to transfer the first sample to a first vessel at the sample dispense position prior to the sample transport transporting the first vessel to a first intermediate position, and wherein the at least one robotic pipettor is configured to transfer the second sample to a second vessel at the sample dispense position;

wherein the first vessel and the second vessel each include a reagent; and wherein the sample transport is configured to continually transport the first vessel and the second vessel along the transport path and to mix the first vessel and the second vessel, respectively, at each intermediate position.

16. The system of claim 1, wherein the sample transport is configured to successively oscillate to mix the first and second samples in the vessel, the vessel moving in an arc with each oscillation.

17. The system of claim 15, wherein the first and second samples are whole blood samples and wherein the reagent includes a lysis buffer.

18. The system of claim 17, wherein the pre-treatment process includes lysing the first sample and the second sample for between about 3 and about 6 minutes.

19. The system of claim 15, wherein the at least one robotic pipettor is further configured to transfer the first and second samples from respective intermediate positions to a third vessel at the sample dispense position to pool the first sample and the second sample.

20. The system of claim 1, wherein the first and second samples comprise whole blood, plasma, serum, cellular blood components, and/or other blood products.

21. The system of claim 1, further comprising a detection system configured to detect a presence of one or more nucleic acids in the pooled sample, and wherein the high-throughput analysis includes a nucleic acid analysis on the pooled sample.

22. The system of claim 21, wherein the system is configured to determine a result from the nucleic acid analysis.

23. The system of claim 22, wherein at least about 140 results are obtained per hour per $m^3$ of a volume occupied by the automated system.

24. The system of claim 22, wherein at least about 280 results are obtained per hour per $m^2$ of a footprint of the automated system.

25. The system of claim 1, further comprising a detection system configured to detect a presence of one or more of a plurality of pathogens or infectious agents, and wherein the high-throughput analysis includes detection of the one or more of a plurality of pathogens or infectious agents.

26. The system of claim 25, wherein upon a determination of the presence of nucleic acids derived from each of the plurality of pathogens or infectious agents as a result of a nucleic acid analysis, the system is indicative of release of donor material associated with the pooled sample for clinical use.

27. The system of claim 25, wherein upon a determination of the presence of a nucleic acid derived from at least one of the plurality of pathogens or infectious agents in the pooled sample, the system is configured to perform onboard deconstruction of the pooled sample to perform nucleic acid analysis of individual samples or sub-pools thereof included in the pooled sample and to make a determination whether donor material associated with each individual sample or sub-pool thereof is acceptable for clinical use based at least in part on the nucleic acid analysis of the individual samples or sub-pools thereof.

28. The system of claim 25, wherein the pooled sample can include up to 96 individual donor samples, and wherein upon a determination of the presence of a nucleic acid derived from at least one of the plurality of pathogens or infectious agents in the pooled sample, the system is configured to perform onboard deconstruction of the pooled sample to make a determination whether donor material associated with each of the 96 individual donor samples is acceptable for clinical use in less than about 4 hours from initial aspiration of the first sample for nucleic acid analysis.

29. The system of claim 27, wherein the system is configured to form a sub-pool on the sample transport and to perform nucleic acid analysis of the sub-pool.

30. The system of claim 1, wherein the sample loading area is configured to store the first and second samples while the high-throughput analysis is performed on the pooled sample.

31. The system of claim 1, further comprising a detection system configured to detect a presence of one or more of a plurality of pathogens or infectious agents, and wherein the high-throughput analysis includes a qualitative assay on the at least a fractionated portion of the pooled sample to detect one or more of the plurality of pathogen or infectious agent.

32. The system of claim 31, wherein the plurality of pathogens or infectious agents are selected from the group consisting of: SARS-COV-2 (COVID-19), HIV-1, HIV-2, HBV, HCV, CMV, Parvo B19 Virus, HAV, *Chlamydia*, Gonorrhea, WNV, Zika Virus, Dengue Virus, Chikungunya Virus, Influenza, *Babesia*, Malaria, Usutu, and HEV.

33. The system of claim 1, further comprising a detection system configured to detect a presence of one or more of a plurality of pathogens or infectious agents, and wherein the high-throughput analysis includes a digital immunoassay analysis on the pooled sample.

34. The system of claim 31, wherein upon detection of a pathogen or infectious agent in the pooled sample, the system is configured to automatically deconstruct the pooled sample onboard.

35. The system of claim 34, wherein upon detection of a pathogen or infectious agent in the pooled sample, the at least one robotic pipettor and sample transport are configured to automatically form sub-pools, each sub-pool comprising a subset of the first sample, second sample, and any additional samples in the pooled sample, and wherein the system is configured to perform a qualitative assay on each sub-pool to determine which sub-pool includes the pathogen or infectious agent.

36. The system of claim 34, wherein the sample loading area is configured to store the first sample, second sample, and any additional samples used to form the pooled sample while high-throughput analysis is performed on the pooled sample, and wherein upon detection of a pathogen or infectious agent in the pooled sample, the at least one robotic pipettor is configured to automatically transfer the first sample, second sample, and any additional samples used to form the pooled sample from the respective sample tube at the sample loading area to the sample transport for sample preparation and further high-throughput analysis to determine which of the first sample, the second sample, or any additional sample used to form the pooled sample, includes the pathogen or infectious agent.

37. The system of claim 1, wherein the at least one robotic pipettor comprises at least three degrees of freedom.

38. The system of claim 1, wherein the at least one robotic pipettor comprises a first robotic pipettor to transfer the first and second samples from the sample loading area to the sample transport, and a second robotic pipettor to pool the first sample and the second sample on the sample transport.

* * * * *